United States Patent
Hwang et al.

(10) Patent No.: US 9,705,093 B2
(45) Date of Patent: *Jul. 11, 2017

(54) HETEROCYCLIC COMPOUND AND ORGANIC LIGHT-EMITTING DEVICE INCLUDING THE SAME

(71) Applicant: Samsung Display Co., Ltd., Yongin, Gyeonggi-do (KR)

(72) Inventors: Seok-Hwan Hwang, Yongin (KR); Young-Kook Kim, Yongin (KR); Jun-Ha Park, Yongin (KR); Hye-Jin Jung, Yongin (KR); Jin-O Lim, Yongin (KR); Eun-Young Lee, Yongin (KR); Sang-Hyun Han, Yongin (KR); Eun-Jae Jeong, Yongin (KR); Soo-Yon Kim, Yongin (KR); Jong-Hyuk Lee, Yongin (KR)

(73) Assignee: Samsung Display Co., Ltd., Yongin, Gyeonggi-do (KR)

( * ) Notice: Subject to any disclaimer, the term of this patent is extended or adjusted under 35 U.S.C. 154(b) by 367 days.

This patent is subject to a terminal disclaimer.

(21) Appl. No.: 14/258,786

(22) Filed: Apr. 22, 2014

(65) Prior Publication Data
US 2014/0361268 A1    Dec. 11, 2014

(30) Foreign Application Priority Data
Jun. 7, 2013   (KR) .................. 10-2013-0065463

(51) Int. Cl.
*H01L 51/00* (2006.01)
*H01L 27/32* (2006.01)
(Continued)

(52) U.S. Cl.
CPC ........ *H01L 51/0072* (2013.01); *C07D 401/14* (2013.01); *H01L 51/0067* (2013.01);
(Continued)

(58) Field of Classification Search
None
See application file for complete search history.

(56) References Cited

U.S. PATENT DOCUMENTS

| | | |
|---|---|---|
| 5,645,948 A | 7/1997 | Shi et al. |
| 6,465,115 B2 | 10/2002 | Shi et al. |
| (Continued) | | |

FOREIGN PATENT DOCUMENTS

| | | |
|---|---|---|
| JP | 10-017860 A | 1/1998 |
| JP | 11-087067 A | 3/1999 |
| KR | 10-1074193 B1 | 10/2011 |

OTHER PUBLICATIONS

Sigma-aldrich.com Product Catalog; 4H-benzo[def]carbazole.
(Continued)

*Primary Examiner* — J. L. Yang
(74) *Attorney, Agent, or Firm* — Lee & Morse, P.C.

(57) ABSTRACT

A heterocyclic compound represented by Formula 1 below and an organic light-emitting device including the heterocyclic compound are provided:

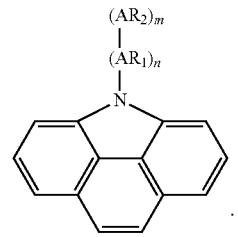

<Formula 1>

20 Claims, 1 Drawing Sheet

(51) Int. Cl.
*H01L 51/50* (2006.01)
*C07D 401/14* (2006.01)

(52) U.S. Cl.
CPC ...... *H01L 51/0052* (2013.01); *H01L 51/0058* (2013.01); *H01L 51/0079* (2013.01); *H01L 51/0081* (2013.01); *H01L 51/5072* (2013.01)

(56) References Cited

U.S. PATENT DOCUMENTS

| | | | |
|---|---|---|---|
| 6,596,415 B2 | 7/2003 | Shi et al. | |
| 7,429,372 B2 | 9/2008 | Pez et al. | |
| 9,419,228 B2* | 8/2016 | Hwang | C09K 11/06 |
| 2011/0084259 A1* | 4/2011 | Lee | H01L 51/5048 257/40 |
| 2011/0210318 A1 | 9/2011 | Bae et al. | |
| 2014/0124748 A1* | 5/2014 | Kim | C07D 403/12 257/40 |
| 2015/0171353 A1* | 6/2015 | Jeong | H01L 51/0094 257/40 |

OTHER PUBLICATIONS

2009 Fall Assembly and Symposium vol. 34, No. 2, 2009.
Y.T. Tao, et al.; "Sharp green electroluminescence from 1H-pyrazolo[3,4-b]quinolone-based light-emitting diodes"; Appl. Phys. Lett. 77,1575, 2000.
C.W. Tang, et al., "Organic electroluminescent diodes", Appl. Phys. Lett. 51, 913, 1987.
Chihaya Adachi, et al. "Confinement of charge carriers and molecular excitons within 5nmthick emitter layer in organic electroluminescent devices with a double heterostructure", Appl Phys. Lett. 57, 521 1990.
Youichi Sakamoto, et al., "Synthesis, Characterization, and Electron-Transport Property of Perfluorinated Phenylene Dendrimers", J. Am. Chem. Soc. 2000, 122, 1832-1833.
Shigehiro Yamaguchi, et al., "Diphenylamino-Substituted 2,5-Diarylsiloles for Single-Layer Organic Electroluminescent Devices",Chemistry Letters 2001, p. 98-99.
Nicholas Johansson, et al., "Solid-State Amplified Spontaneous Emission in Some Spiro-Type Molecules: A New Concept for the Design of Solid-State Lasing Moleculdes", Advanced Materials, Communications, Mar. 6, 1998.

* cited by examiner

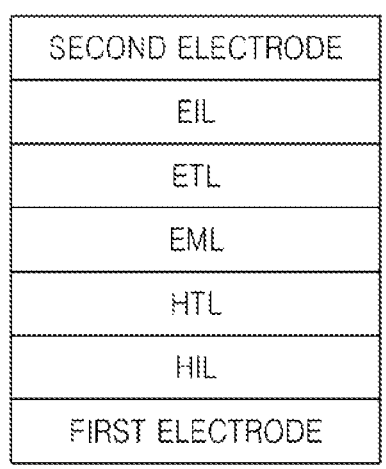

HETEROCYCLIC COMPOUND AND ORGANIC LIGHT-EMITTING DEVICE INCLUDING THE SAME

CROSS-REFERENCE TO RELATED APPLICATION

Korean Patent Application No. 10-2013-0065463, filed on Jun. 7, 2013, in the Korean Intellectual Property Office, and entitled: "Heterocyclic Compound and Organic Light-Emitting Device Comprising the Same," is incorporated by reference herein in its entirety.

BACKGROUND

1. Field

Embodiments relate to a heterocyclic compound and an organic light-emitting device including the heterocyclic compound.

2. Description of the Related Art

Organic light-emitting devices (OLEDs), which are self-emitting devices, have advantages such as wide viewing angles, excellent contrast, quick response, high brightness, excellent driving voltage characteristics, and can provide multicolored images.

A typical OLED has a structure including a substrate, and an anode, a hole transport layer (HTL), an emission layer (EML), an electron transport layer (ETL), and a cathode which are sequentially stacked on the substrate. In this regard, the HTL, the EML, and the ETL are organic thin films formed of organic compounds.

An operating principle of an OLED having the above-described structure is as follows.

When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

SUMMARY

Embodiments are directed to a heterocyclic compound represented by Formula 1 below:

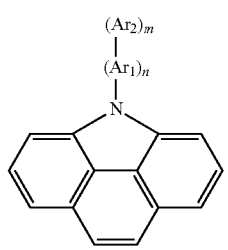

<Formula 1>

In Formula 1, $Ar_1$ may be a substituted or unsubstituted C6-60 arylene group;

$Ar_2$ may be a substituted or unsubstituted C6-60 aryl group, a substituted or unsubstituted C2-60 heteroaryl group, or a substituted or unsubstituted C6-60 condensed polycyclic group;

n may be an integer from 0 to 3; and m may be an integer from 1 to 3.

n may be an integer from 1 to 3, and $Ar_1$ in Formula 1 may be one of the groups represented by Formulae 2a and 2b below:

In Formulae 2a and 2b, * indicates a binding site.

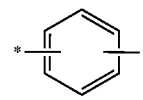

2a

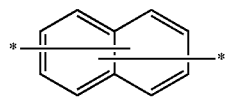

2b $Ar_2$ in Formula 1 may be one of the groups represented by Formulae 3a to 3f below:

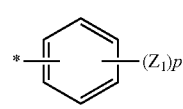

3a

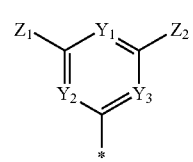

3b

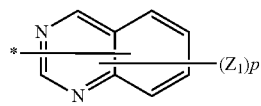

3c

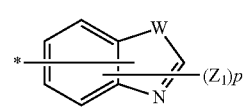

3d

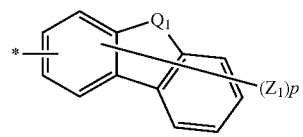

3e

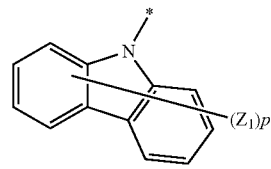

3f

In Formulae 3a to 3f, $Q_1$ may be $-CR_{21}R_{22}-$, $-S-$, or $-O-$;

W may be $-O-$, $-S-$, or $-NR_{23}-$;

$Y_1$ to $Y_1$ may each independently be CH or N; and $Z_1$, $Z_2$, $R_{21}$, $R_{22}$, and $R_{23}$ may each independently be a hydrogen atom, a deuterium atom, a substituted or unsubstituted C1-C20 alkyl group, a C1-C20 alkylsilyl group, a C1-C20 arylsilyl group, a substituted or unsubstituted C6-C20 aryl group, a substituted or unsubstituted C2-C20 heteroaryl group, a substituted or unsubstituted C6-C20 condensed polycyclic group, an amino group substituted with a C6-C20 aryl group or a C2-C20 heteroaryl group, a halogen group, a cyano group, a nitro group, a hydroxyl group, or a carboxy group, and p may be an integer from 1 to 8, and

* indicates a binding site.

$Ar_1$ in Formula 1 may be one of the groups represented by Formulae 4a to 4c below:

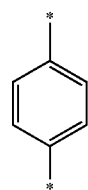

4a

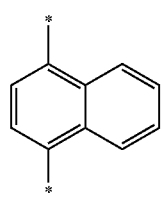

4b

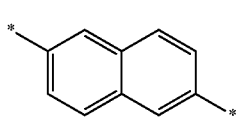

4c

In Formulae 4a to 4c, * indicates a binding site.

The heterocyclic compound of Formula 1 may be one of the compounds below:

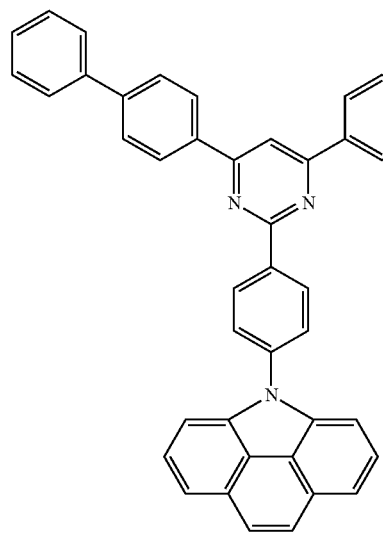

7

-continued

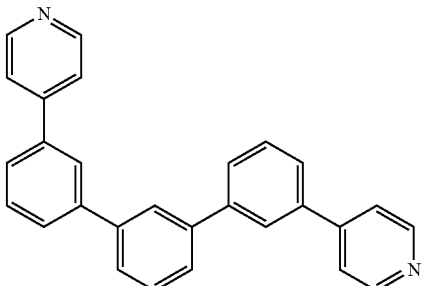

11

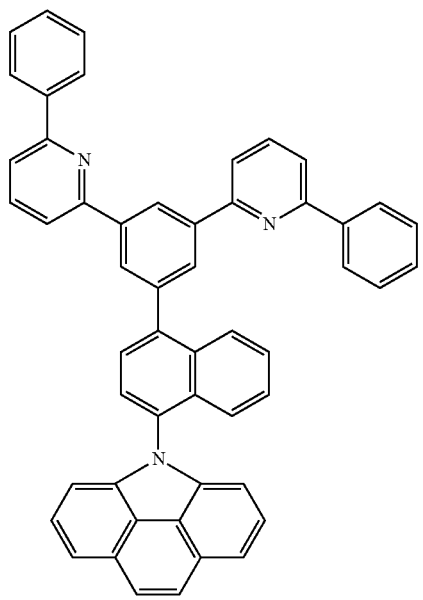

18

23

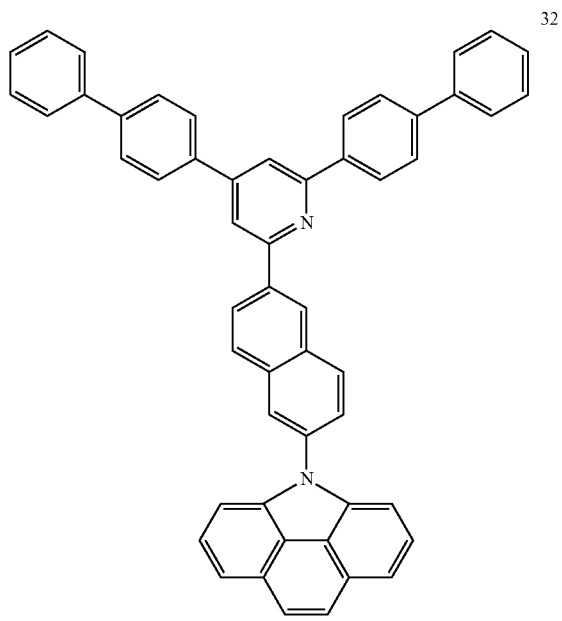
32
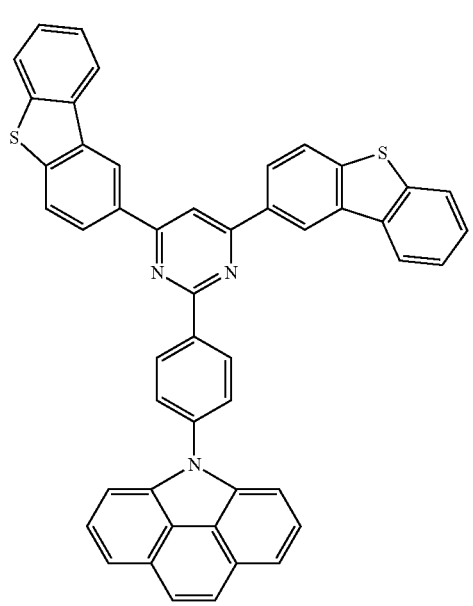
51
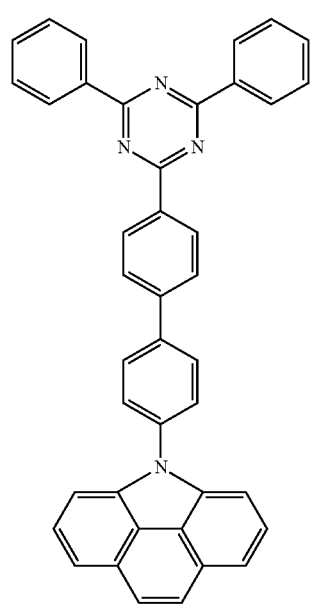
44
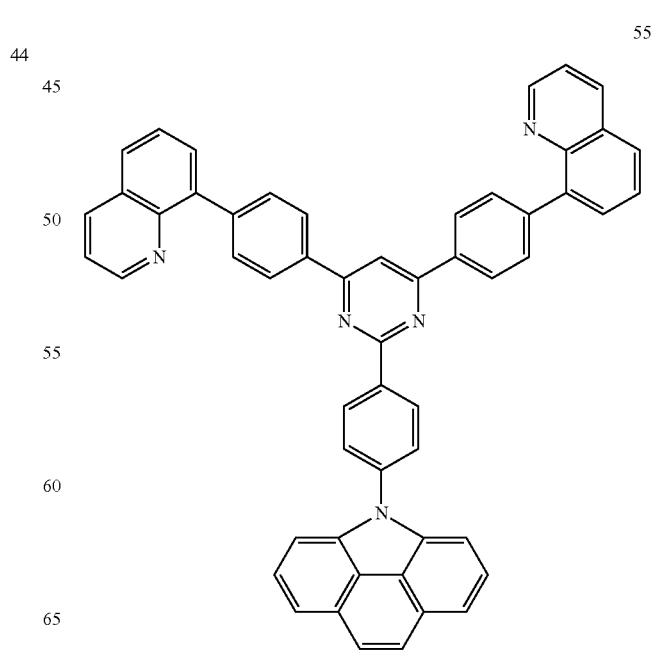
55

-continued

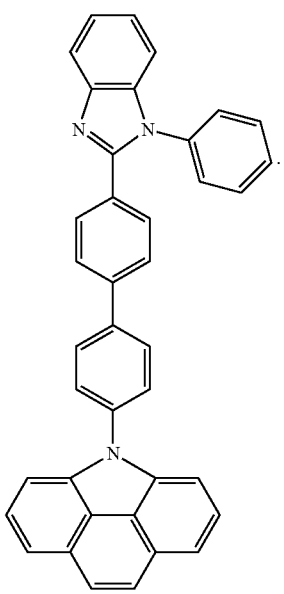

Embodiments are also directed to an organic light-emitting device, including a first electrode, a second electrode, and an organic layer disposed between the first electrode and the second electrode. The organic layer may include the heterocyclic compound as claimed in claim 1.

The organic layer may be an electron transport layer.

The organic layer may include an emission layer and may further include an electron injection layer, an electron transport layer, a functional layer having both electron injection and transport capabilities, a hole injection layer, a hole transport layer, or a functional layer having both hole injection and transport capabilities, and the emission layer may include an anthracene-based compound, an arylamine-based compound, or a styryl-based compound.

The organic layer may include an emission layer and may further include an electron injection layer, an electron transport layer, a functional layer having both electron injection and transport capabilities, a hole injection layer, a hole transport layer, or a functional layer having both hole injection and transport capabilities, and the emission layer may include red, green, blue, or white emission layers one of which includes a phosphorescent compound.

At least one of the hole injection layer, the hole transport layer, and the functional layer having both hole injection and hole transport capabilities may include a charge-generating material.

The charge-generating material may be a p-type dopant.

The p-type dopant may be a quinone dopant.

The p-type dopant may be a metal oxide.

The p-type dopant may be a cyano group-containing compound.

The organic layer may include an electron transport layer, and the electron transport layer may further include a metal complex.

The metal complex may be a lithium (Li) complex.

The metal complex may be lithium quinolate (LiQ).

The metal complex may be Compound 203 below.

<Compound 203>

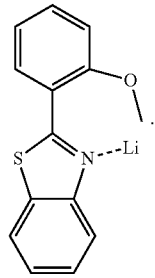

The organic layer may be formed from the heterocyclic compound using a wet process.

Embodiments are also directed to a flat panel display device including an organic light-emitting device according to an embodiment. The first electrode of the organic light-emitting device may be electrically connected to a source electrode or a drain electrode of a thin-film transistor.

BRIEF DESCRIPTION OF THE DRAWING

Features will become apparent to those of skill in the art by describing in detail exemplary embodiments with reference to the attached drawing in which:

FIG. 1 illustrates a schematic view of a structure of an organic light-emitting device according to an example embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art. In the drawing figures, the dimensions of layers and regions may be exaggerated for clarity of illustration. Like reference numerals refer to like elements throughout.

As used herein, the term "and/or" includes any and all combinations of one or more of the associated listed items. Expressions such as "at least one of," when preceding a list of elements, modify the entire list of elements and do not modify the individual elements of the list.

According to an example embodiment, there is provided a heterocyclic compound represented by Formula 1 below.

<Formula 1>

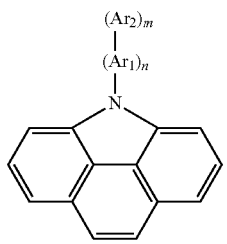

According to the present example embodiment, in Formula 1 above, $Ar_1$ is a substituted or unsubstituted C6-60 arylene group;

$Ar_2$ is a substituted or unsubstituted C6-60 aryl group, a substituted or unsubstituted C2-60 heteroaryl group, or a substituted or unsubstituted C6-60 condensed polycyclic group;

n is an integer from 0 to 3; and m is an integer from 1 to 3.

When $Ar_1$ or $Ar_2$ is plural, $(Ar_1)_n$ or $(Ar_2)_m$ may be a linkage of $Ar_1$s or $Ar_2$s that are the same or different.

Suitable electron transport materials for organic light-emitting devices include organic unimolecular materials, for example, organic metal complexes with relatively high electron stability and electron mobility. In particular, Alq3 may provide higher stability and higher electron affinity than other organic metal complexes. However, when used in a blue light-emitting device, Alq3 may deteriorate color purity due to the light emission caused by exciton diffusion.

Examples of electron transport materials are a Flavon derivative or a germanium derivative, and a silicon chloropentadiene derivative.

A 2-biphenyl-4-yl-5-(4-t-butylphenyl)-1,3,4-oxadiazole (PBD) derivative bound with a spiro compound, and 2,2′,2″-(benzene-1,3,5-triyl)-tris(I-phenyl-1H-benzimidazole (TPBI) with hole blocking and electron transporting capabilities are organic unimolecular materials. For example, benzoimidazole derivatives may afford good durability. However, an organic light-emitting device using such an organic unimolecular material in an electron transport layer may have a short emission lifetime, a poor storage durability, and a low reliability, which, without being bound by theory, are believed to be the result of physical, chemical, photochemical, or electrochemical changes of such organic materials, oxidation and exfoliation of anodes, and poor durability of anodes.

The heterocyclic compound of Formula 1 above may be used as an electron transporting material in organic light-emission devices. The heterocyclic compound of Formula 1 includes a heterocyclic group, and has a high glass transition temperature (Tg) or melting point. Thus, the heterocyclic compound may provide high heat resistance against Joule heating generated in an organic layer, between organic layers, or between an organic layer and a metal electrode when light emission occurs, and may provide high durability in high-temperature environments. An organic light-emitting device manufactured using the heterocyclic compound of Formula 1 may have high durability when stored or operated.

Substituents in the heterocyclic compound of Formula 1 will now be described in detail.

In some example embodiments, $Ar_2$ in Formula 1 may be one of the groups represented by Formulae 2a and 2b below.

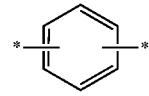

2a

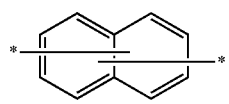

2b

In Formulae 2a and 2b, * indicates a binding site.

In some example embodiments, $Ar_2$ in Formula 1 may be one of the groups represented by Formulae 3a to 3f below:

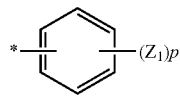

3a

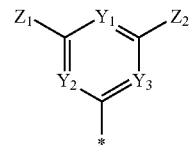

3b

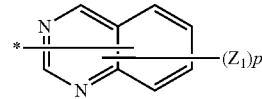

3c

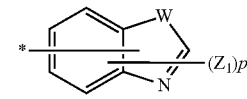

3d

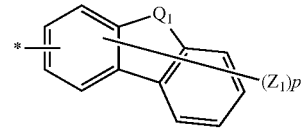

3e

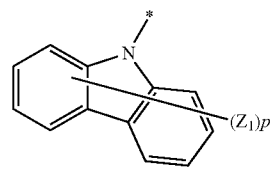

3f

In Formulae 3a to 3f, $Q_1$ may be —$CR_{21}R_{22}$—, —S—, or —O—;

W may be —O—, —S—, or —$NR_{23}$—;

$Y_1$ to $Y_3$ may each independently be CH or N;

$Z_1$, $Z_2$, $R_{21}$, $R_{22}$, and $R_{23}$ may each independently be a hydrogen atom, a deuterium atom, a substituted or unsubstituted C1-C20 alkyl group, a C1-C20 alkylsilyl group, a C1-C20 arylsilyl group, a substituted or unsubstituted C6-C20 aryl group, a substituted or unsubstituted C2-C20 heteroaryl group, a substituted or unsubstituted C6-C20 condensed polycyclic group, an amino group substituted with a C6-C20 aryl group or a C2-C20 heteroaryl group, a halogen group, a cyano group, a nitro group, a hydroxyl group, or a carboxy group; and p may be an integer from 1 to 8; and * indicates a binding site.

The binding site may be a binding site of a single $Ar_1$ or multiple $Ar_2$s that may be the same or different. This may be understood with reference to example compounds described below.

In some example embodiments, $Ar_1$ in Formula 1 may be one of the groups represented by Formulae 4a to 4c below:

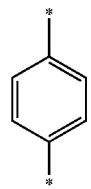

4a

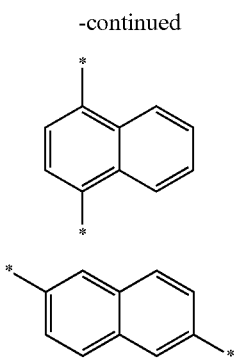

4b

4c

In Formulae 4a to 4c, * indicates a binding site.

Hereinafter, substituents described with reference to the formulae will now be described in detail. In this regard, the numbers of carbons in substituents are presented only for illustrative purposes and do not limit the characteristics of the substituents. The substituents not defined herein are construed as the same meanings understood by one of ordinary skill in the art.

The unsubstituted C1-C60 alkyl group used herein may be linear or branched. Examples of the alkyl group may include, but are not limited to, a methyl group, an ethyl group, a propyl group, an isobutyl group, a sec-butyl group, a pentyl group, an iso-amyl group, a hexyl group, a heptyl group, an octyl group, a nonanyl group, and a dodecyl group. At least one hydrogen atom of the alkyl group may be substituted with a deuterium atom, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid group or a salt thereof, a C1-C10 alkyl group, a C1-C10 alkoxy group, a C2-C10 alkenyl group, a C2-C10 alkynyl group, a C6-C16 aryl group substituted with a C6-C16 aryl group or a C4-C16 heteroaryl group, an unsubstituted C6-C16 aryl group, a C4-C16 heteroaryl group substituted with a C6-C16 aryl group or a C4-C16 heteroaryl group, or an unsubstituted C4-C16 heteroaryl group.

The unsubstituted C2-C60 alkenyl group indicates an unsaturated alkyl groups having at least one carbon-carbon double bond in the center or at a terminal of the alkyl group. Examples of the alkenyl group are an ethenyl group, a propenyl group, a butenyl group, and the like. At least one hydrogen atom in the unsubstituted alkenyl group may be substituted with a substituent described above in conjunction with the alkyl group.

The unsubstituted C2-C60 alkynyl group indicates an alkyl group having at least one carbon-carbon triple bond in the center or at a terminal of the alkyl group. Some examples of the unsubstituted C2-C20 alkynyl group are acetylene, propylene, phenylacetylene, naphthylacetylene, isopropylacetylene, t-butylacetylene, and diphenylacetylene. At least one hydrogen atom in the alkynyl group may be substituted with a substituent described above in conjunction with the alkyl group.

The unsubstituted C3-C60 cycloalkyl group indicates a C3-C60 cyclic alkyl group wherein at least one hydrogen atom in the cycloalkyl group may be substituted with a substituent described above in conduction with the C1-C60 alkyl group.

The unsubstituted C1-C60 alkoxy group indicates a group having a structure of —OA wherein A is an unsubstituted C1-C60 alkyl group as described above. Some examples of the unsubstituted C1-C60 alkoxy group are a methoxy group, an ethoxy group, a propoxy group, an isopropyloxy group, a butoxy group, and a pentoxy group. At least one hydrogen atom of the alkoxy group may be substituted with a substituent such as those described above in conjunction with the alkyl group.

The unsubstituted C6-C60 aryl group indicates a carbocyclic aromatic system containing at least one ring. At least two rings may be fused to each other or linked to each other by a single bond. The term 'aryl' refers to an aromatic system, such as phenyl, naphthyl, or anthracenyl. At least one hydrogen atom in the aryl group may be substituted with a substituent described above in conjunction with the unsubstituted C1-C60 alkyl group.

Some examples of the substituted or unsubstituted C6-C60 aryl group are a phenyl group, a C1-C10 alkylphenyl group (for example, an ethylphenyl group), a biphenyl group, a C1-C10 alkyl biphenyl group, a C1-C10 alkoxybiphenyl group, a o-, m-, and p-toryl group, an o-, m-, and p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a C1-C10 alkylnaphthyl group (for example, a methylnaphthyl group), a C1-C10 alkoxynaphthyl group (for example, a methoxynaphthyl group), an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrycenyl group, an ethyl-chrysenyl group, a picenyl group, a perylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptacenyl group, a pyranthrenyl group, and an ovalenyl group.

The unsubstituted C2-C60 heteroaryl group used herein includes one, two, three, or four heteroatoms selected from N, O, P, and S. At least two rings may be fused to each other or linked to each other by a single bond. Some examples of the unsubstituted C2-C60 heteroaryl group are a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indol group, a quinolyl group, an isoquinolyl group, and a dibenzothiophene group. In addition, at least one hydrogen atom in the heteroaryl group may be substituted with a substituent described above in conjunction with the unsubstituted C1-C60 alkyl group.

The unsubstituted C6-C60 aryloxy group is a group represented by —OA₁, wherein A₁ may be a C6-C60 aryl group. An example of the aryloxy group is a phenoxy group. At least one hydrogen atom in the aryloxy group may be substituted with a substituent described above in conjunction with the unsubstituted C1-C60 alkyl group.

The unsubstituted C6-C60 arylthio group is a group represented by —SA₁, wherein A₁ may be a C6-C60 aryl group. Some examples of the arylthio group are a benzenethio group and a naphthylthio group. At least one hydrogen atom in the arylthio group may be substituted with a substituent described above in conjunction with the unsubstituted C1-C60 alkyl group.

The unsubstituted C6-C60 condensed polycyclic group used herein refers to a substituent including at least two rings wherein at least one aromatic ring and/or at least one non-aromatic ring are fused to each other, or refers to a substituent having an unsaturated group in a ring that may not form a conjugate structure. The unsubstituted C6-C60 condensed polycyclic group are distinct from an aryl group or a heteroaryl group in terms of being non-aromatic.
Some examples of the compound represented by Formula 1 are Compounds 1 to 65 represented by the following formulae.
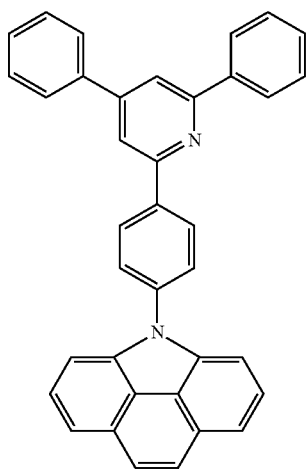
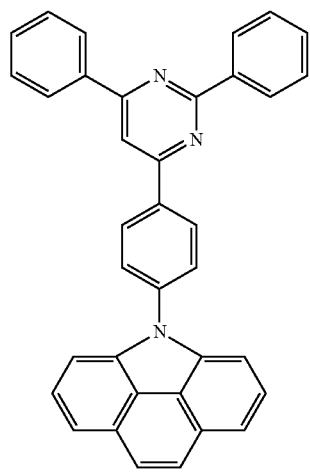
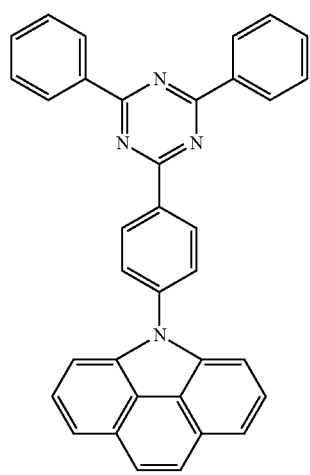
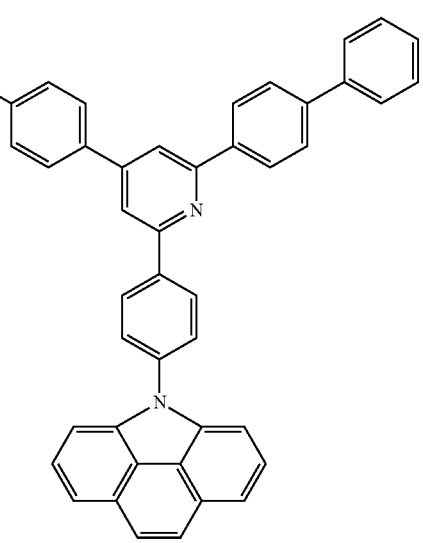

7
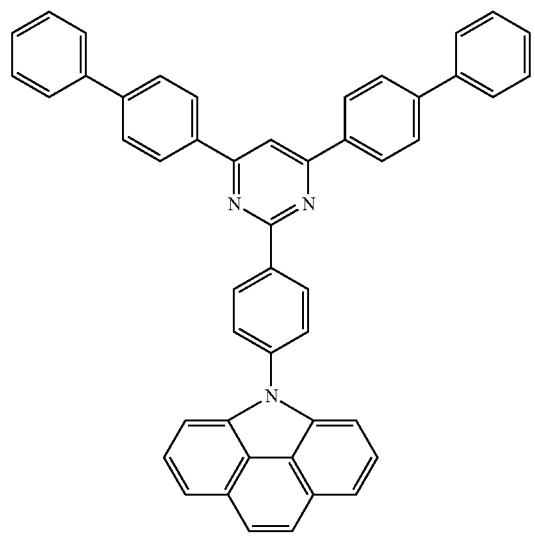
8
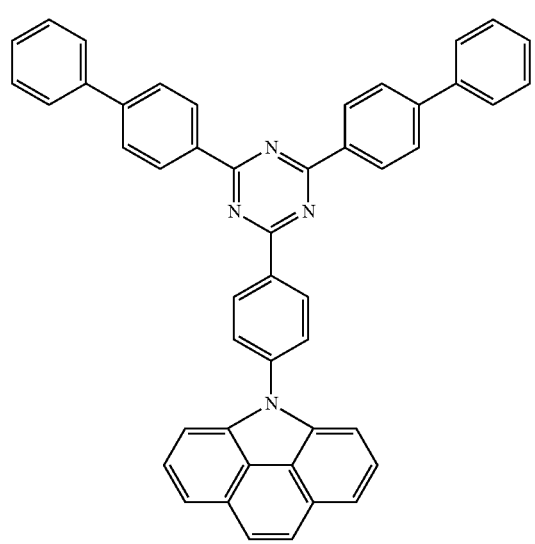
9
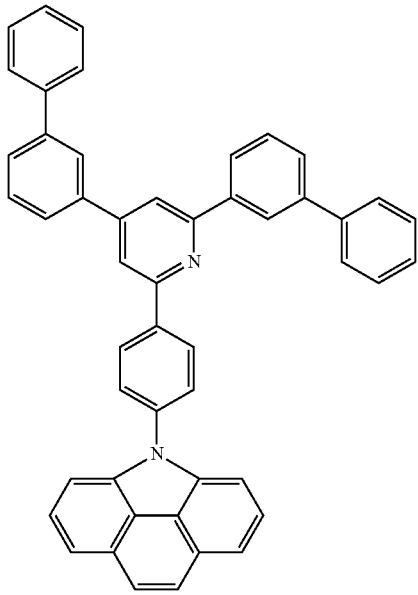
10
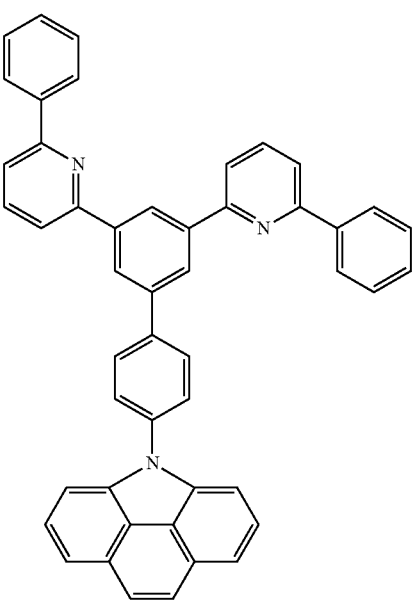

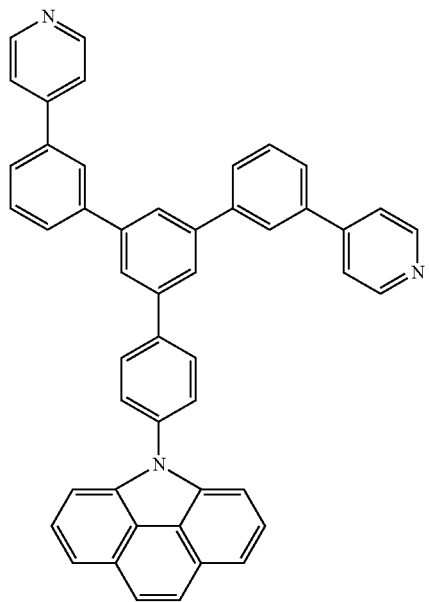
11
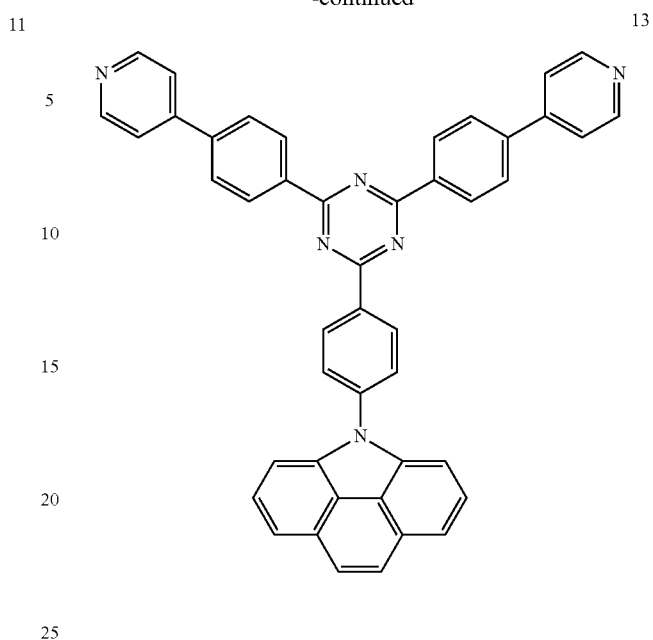
13
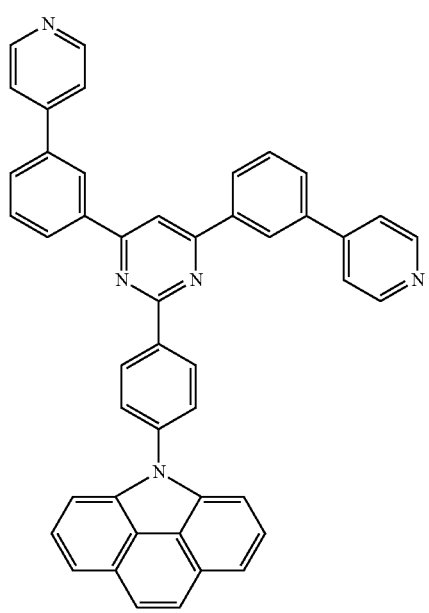
12
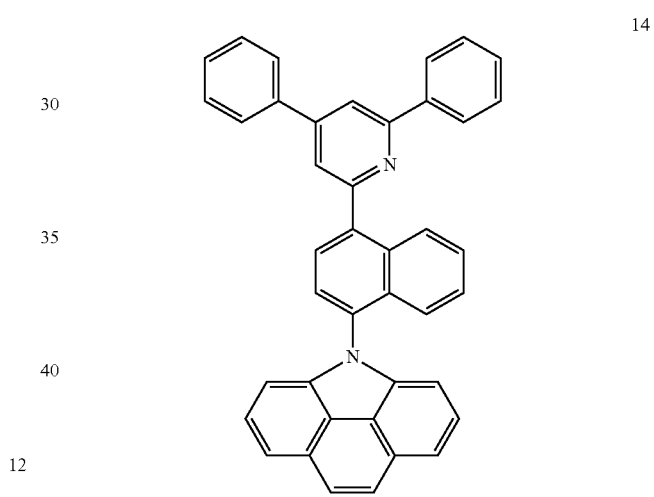
14
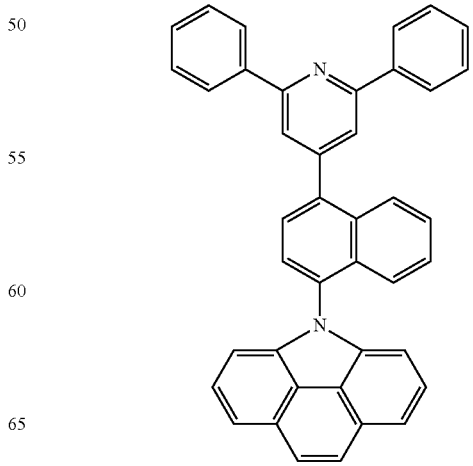
15

16
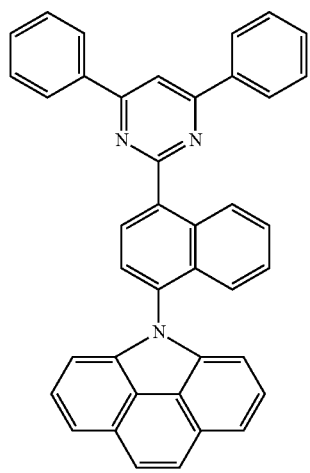
17
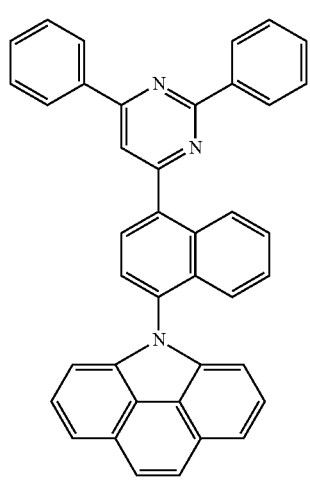
18
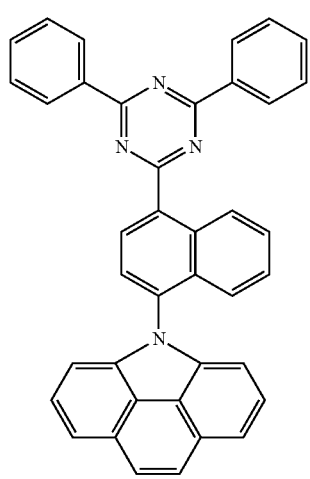
19
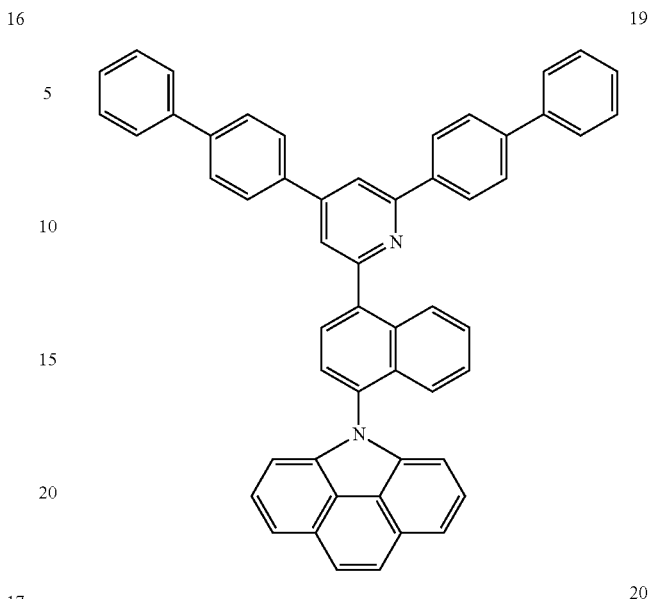
20
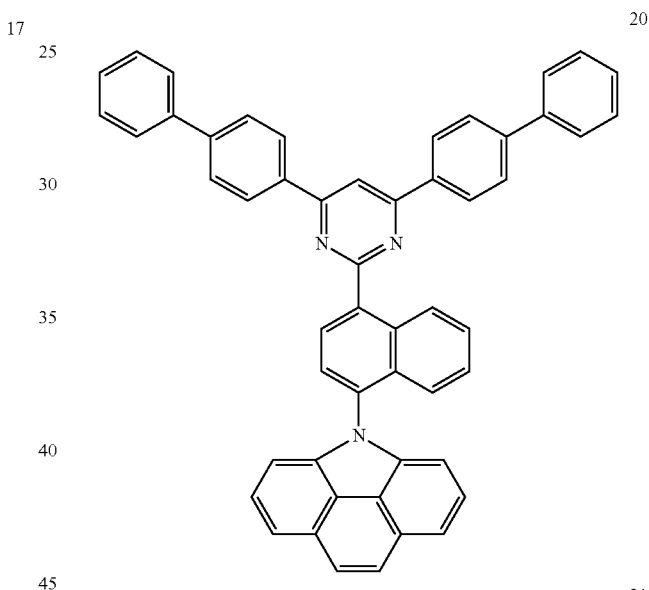
21
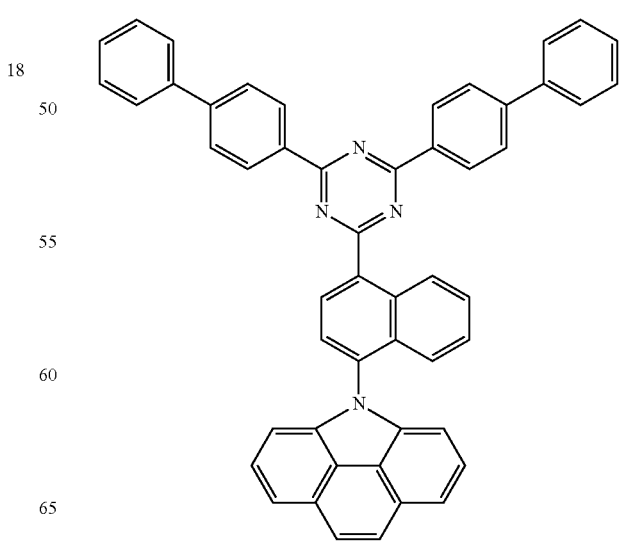

22
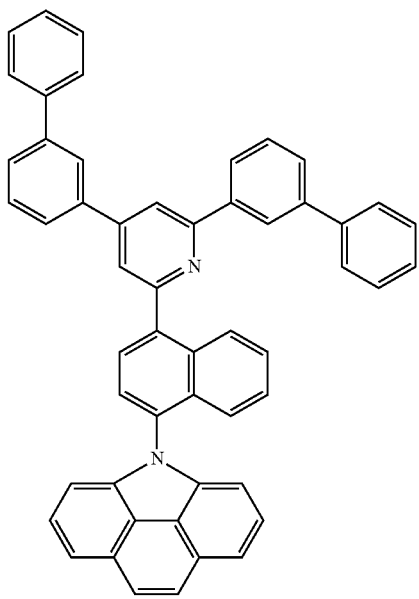
24
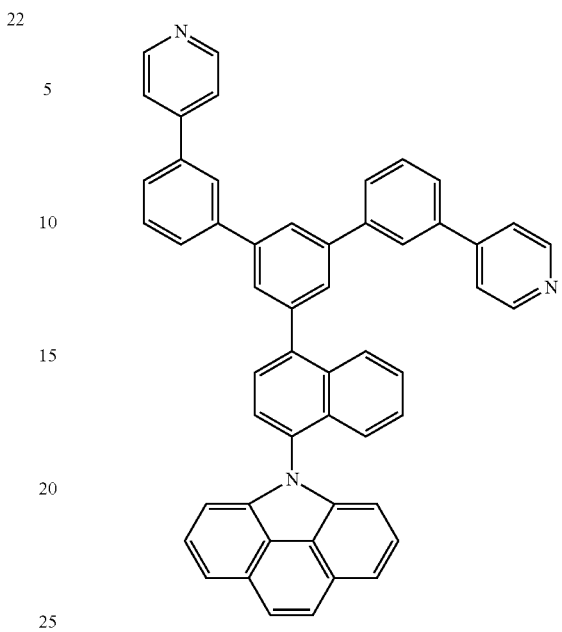
23
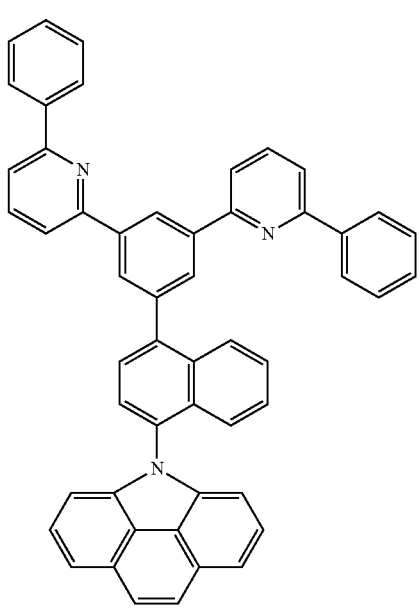
25
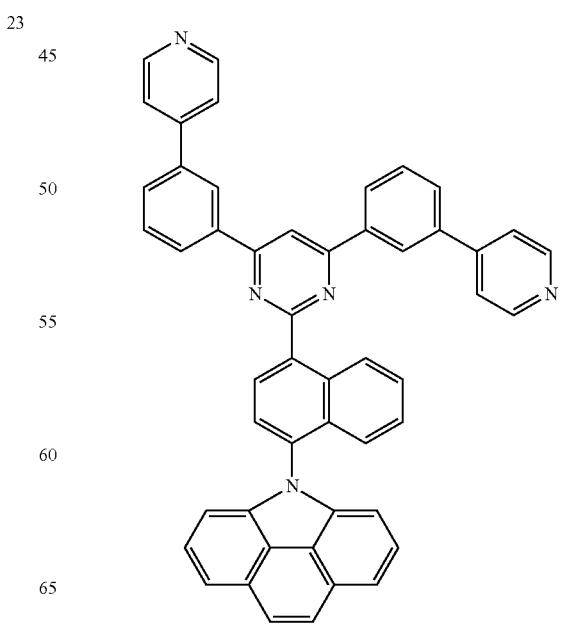

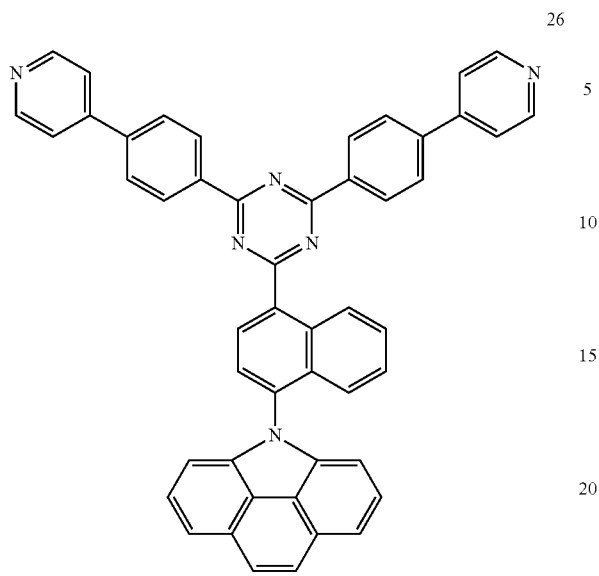
26
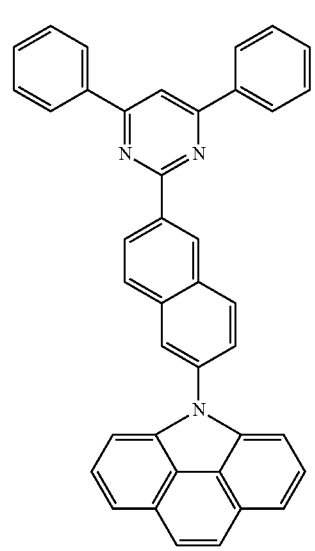
29
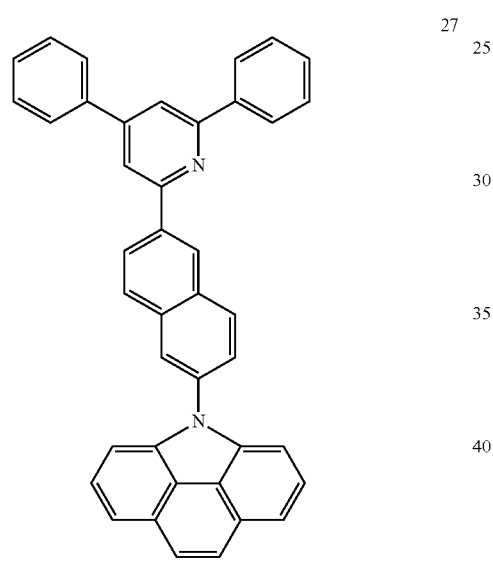
27
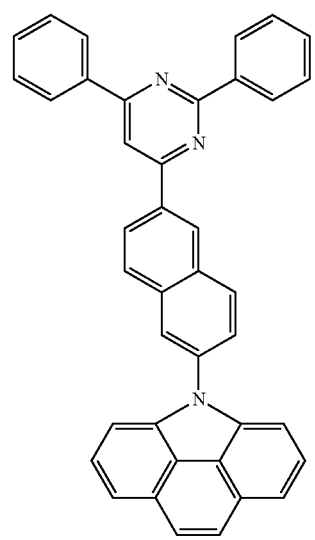
30
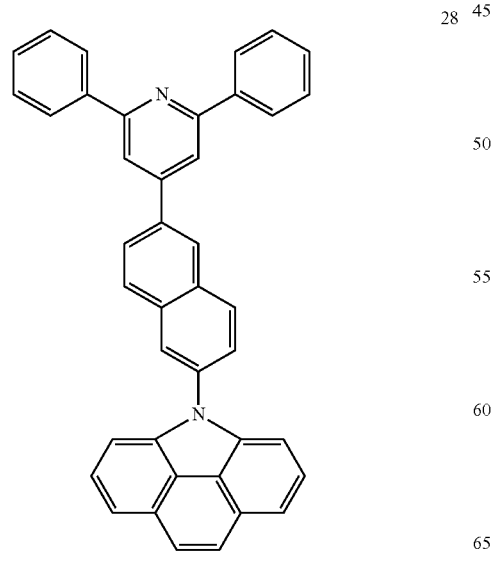
28
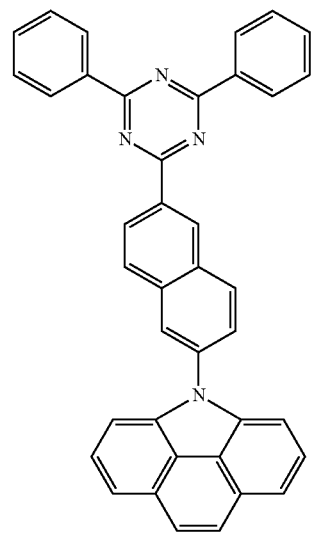
31

32
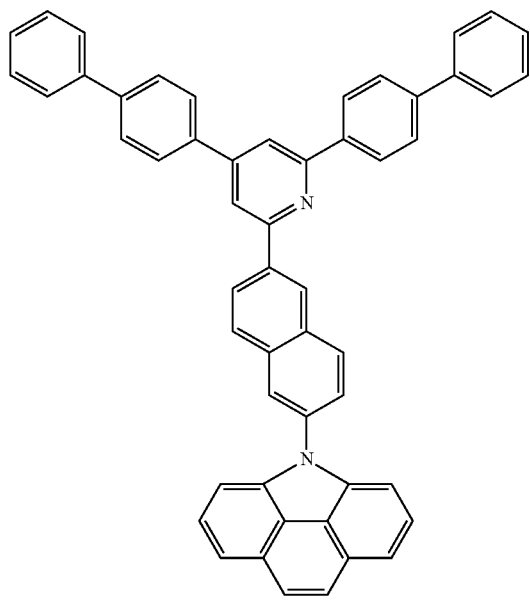
33
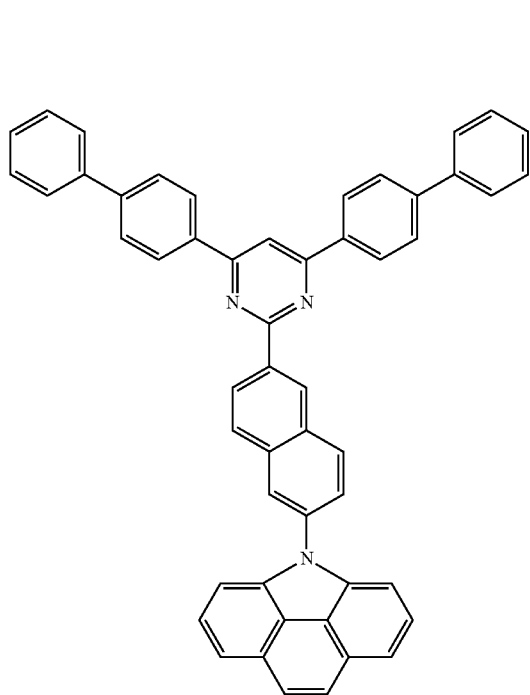
34
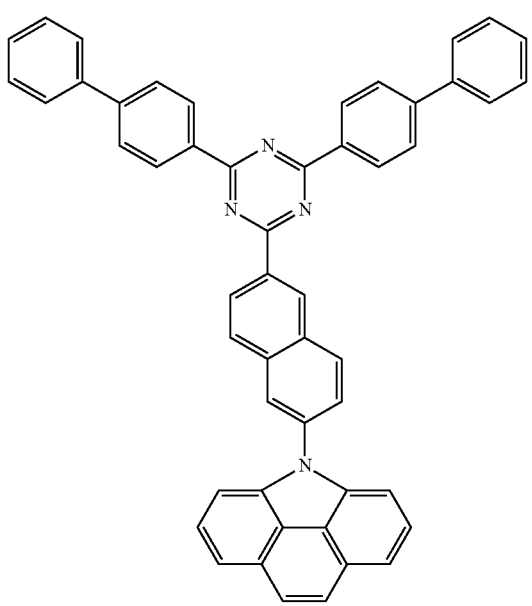
35
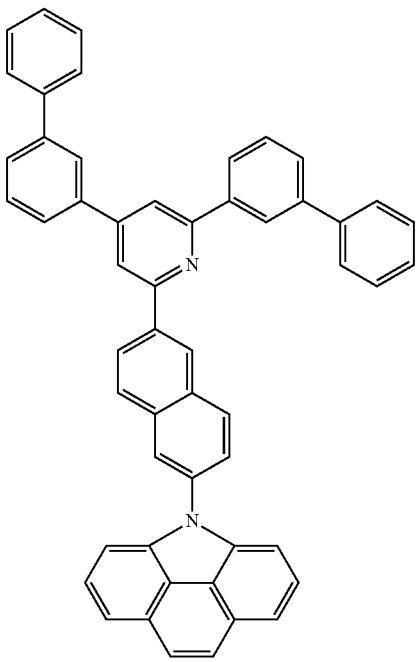

36
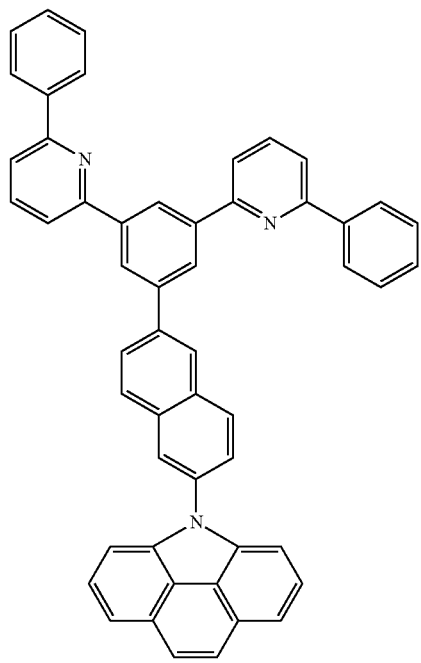
37
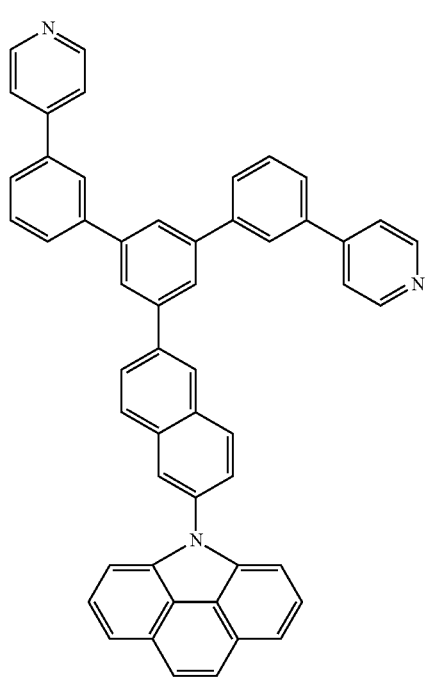
38
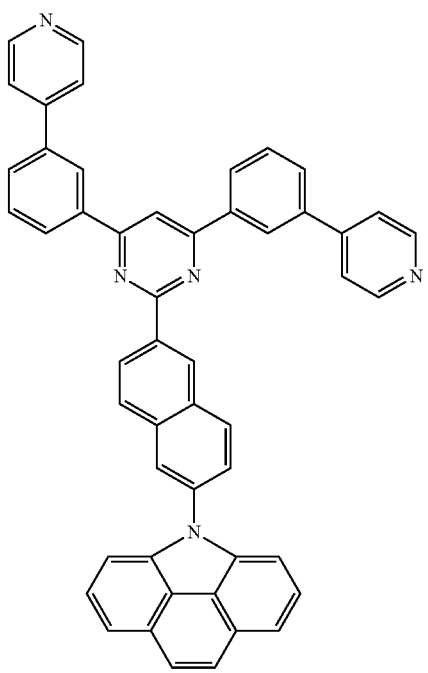
39
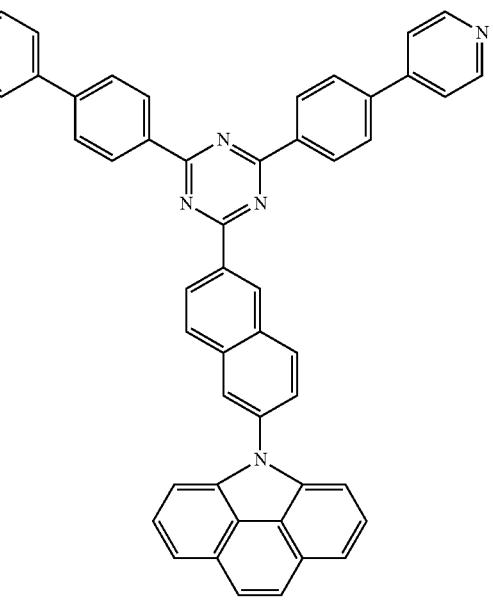

40
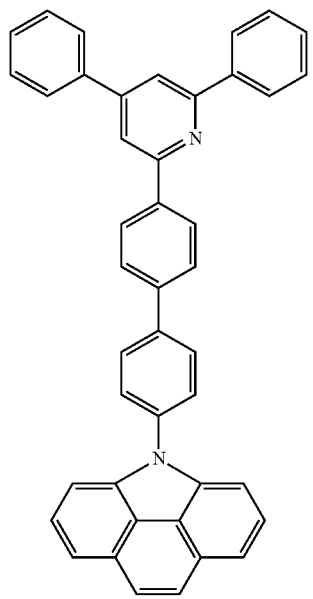
42
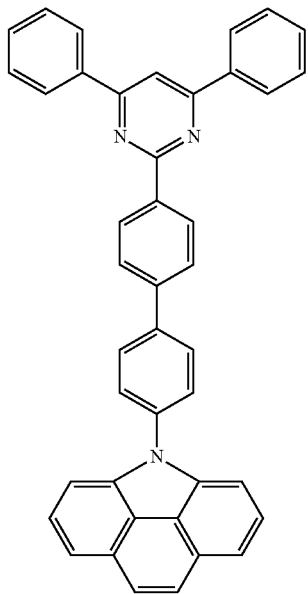
41
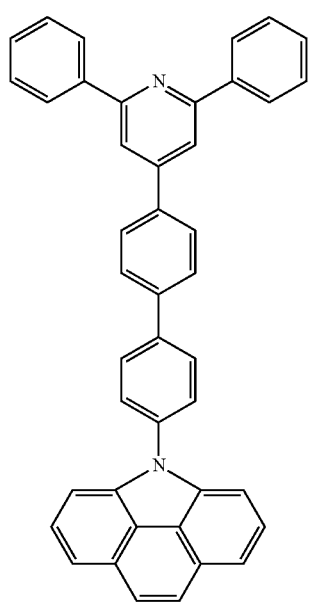
43
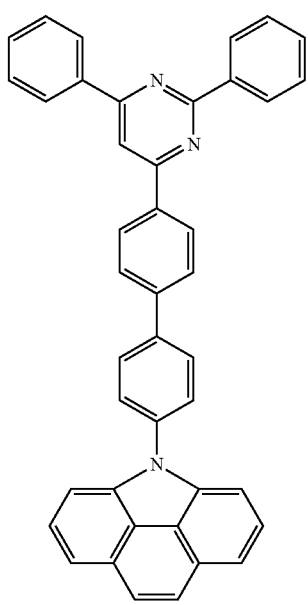

-continued
44
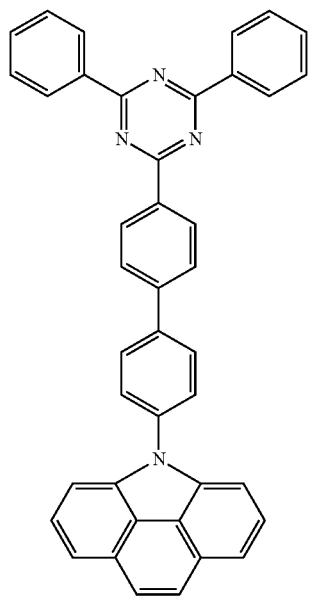
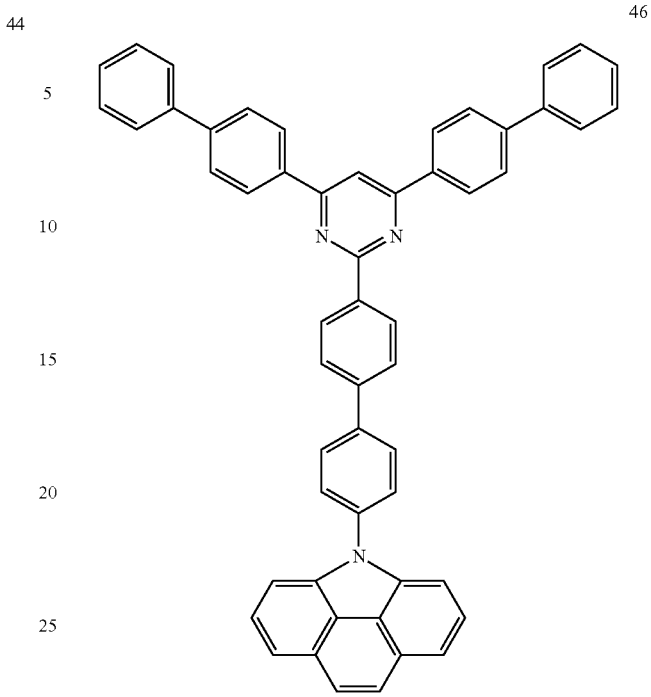
46
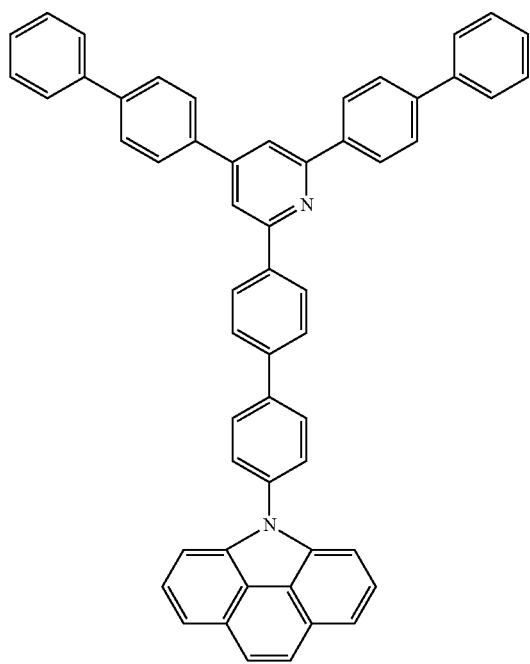
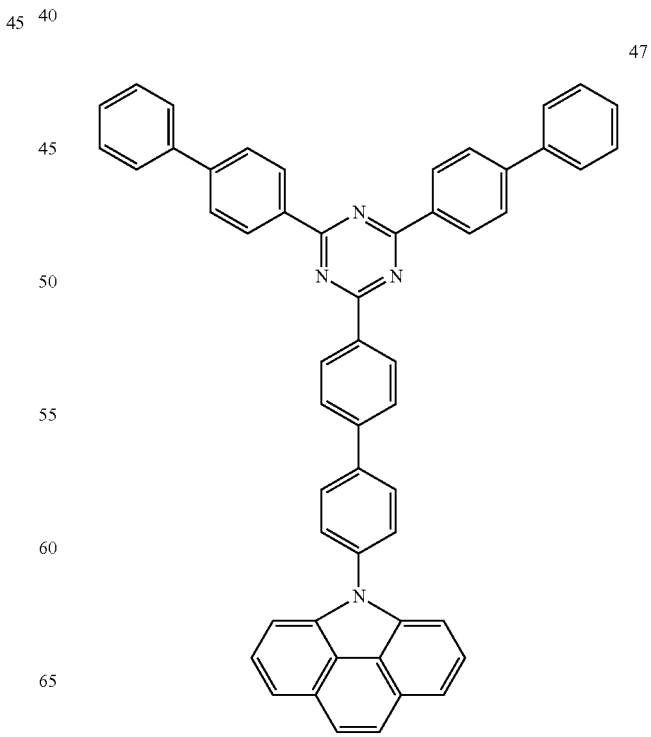
47

48
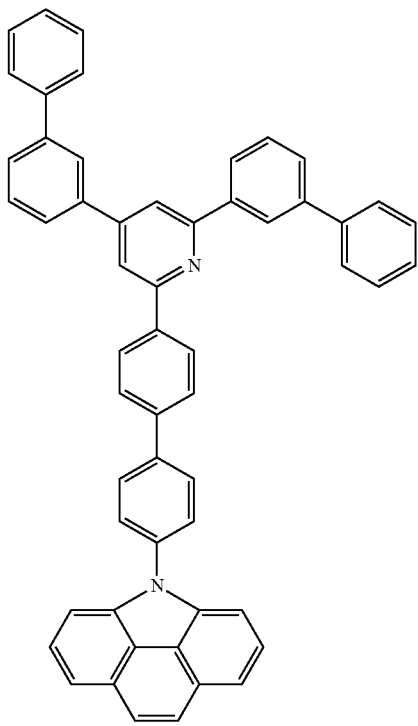
50
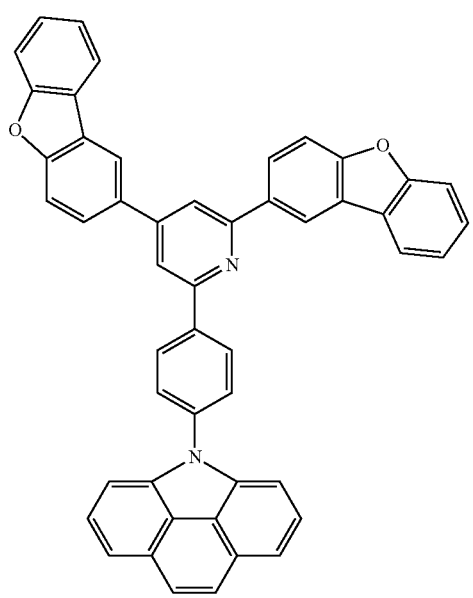
49
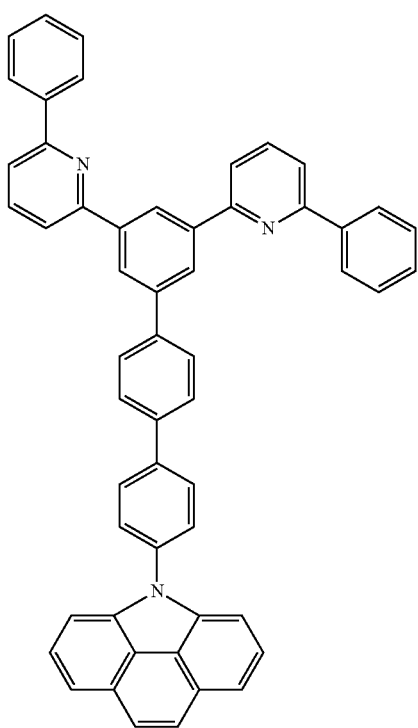
51
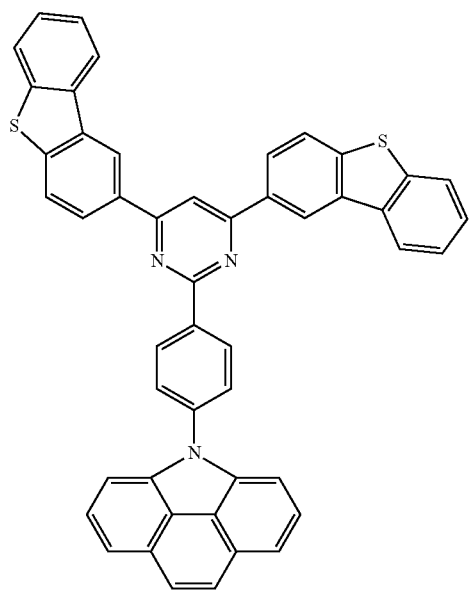

-continued
52
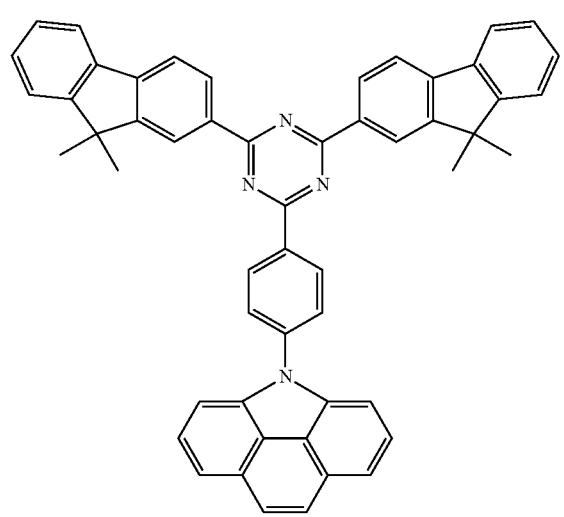
53
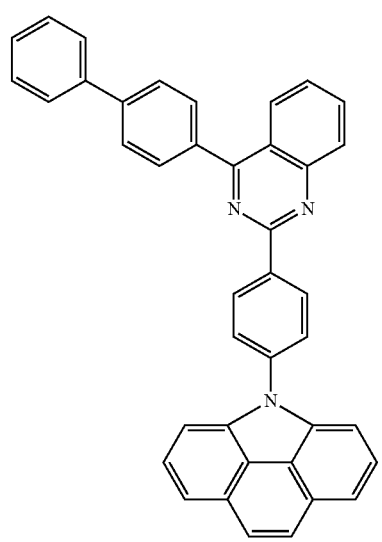
54
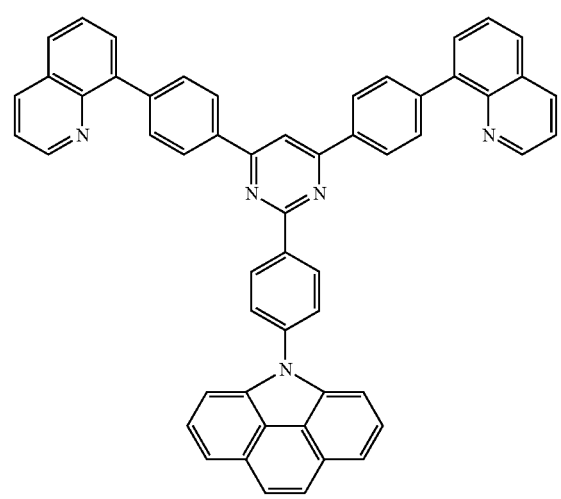
-continued
55
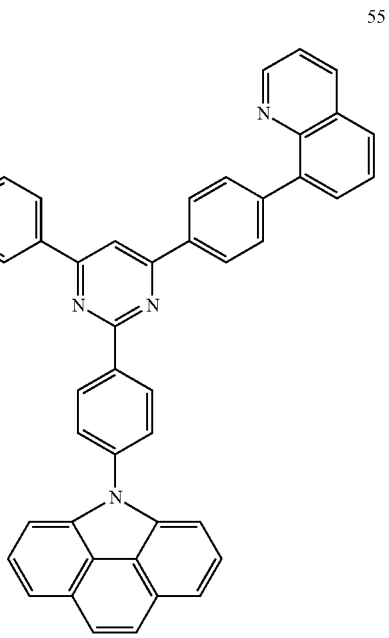
56
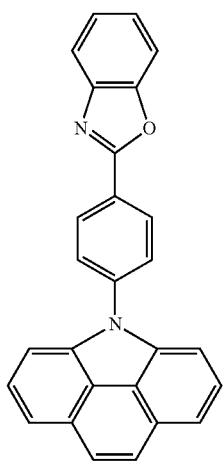
57
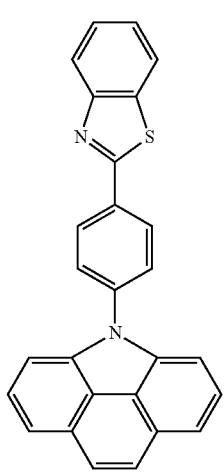

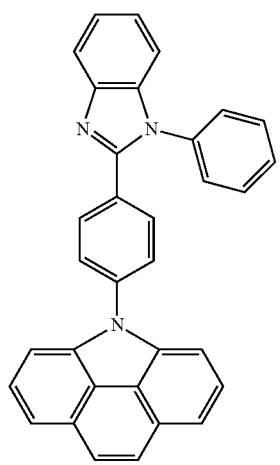
58
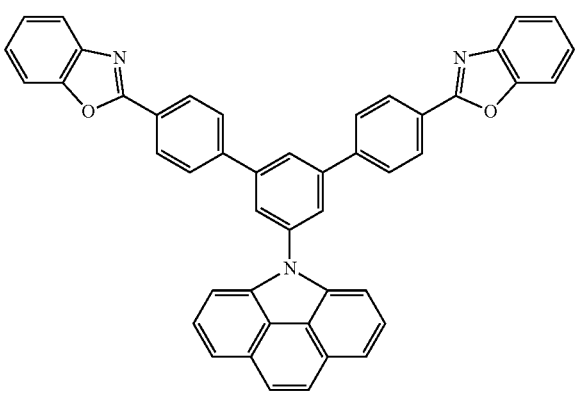
61
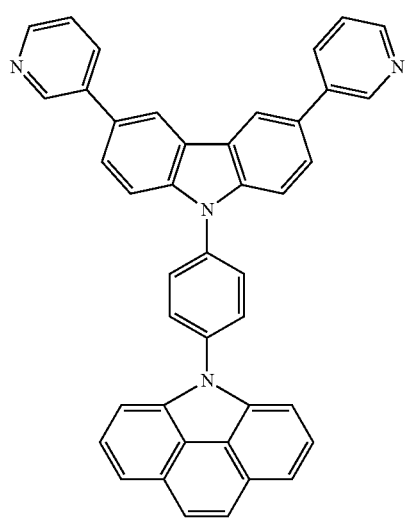
59
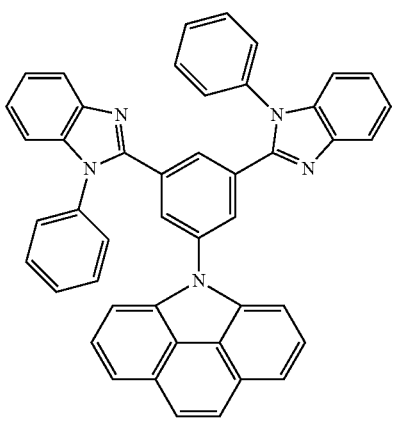
62
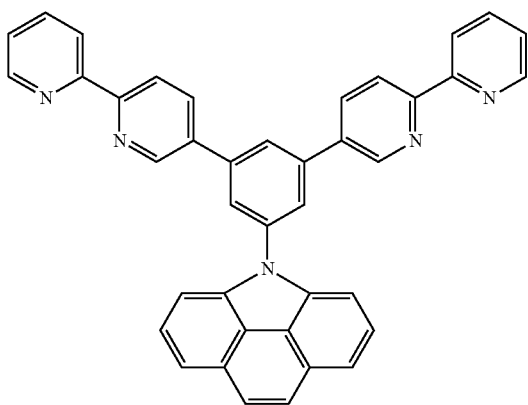
60
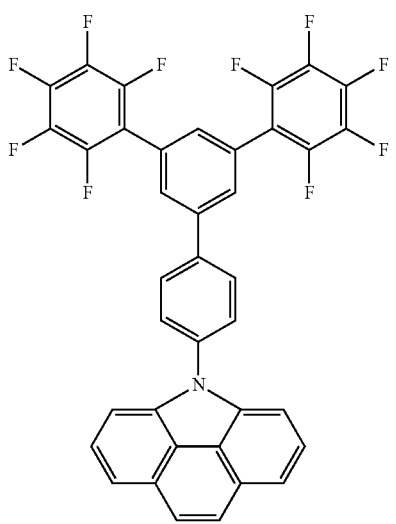
63

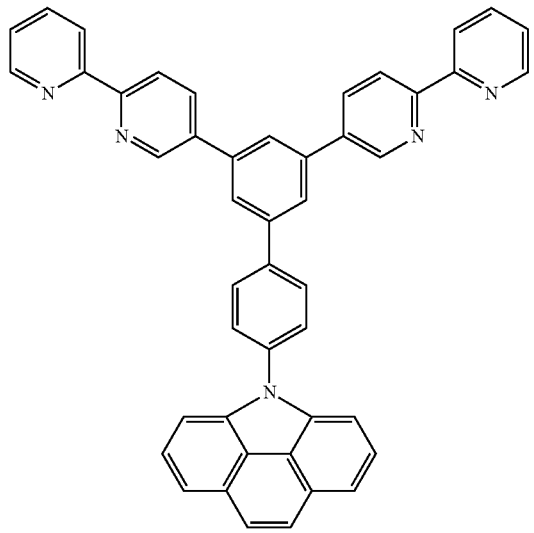

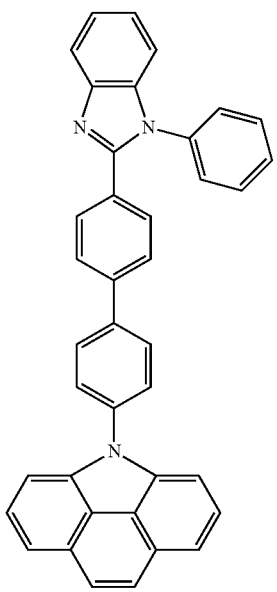

According to another example embodiment, an organic light-emitting device includes a first electrode, a second electrode, and an organic layer disposed between the first electrode and the second electrode, wherein the organic layer includes the compound of Formula 1 described above.

The organic layer may include at least one layer selected from among a hole injection layer, a hole transport layer, a functional layer having both hole injection and hole transport capabilities (hereinafter, "H-functional layer"), a buffer layer, an electron blocking layer, an emission layer, a hole blocking layer, an electron transport layer, an electron injection layer, and a functional layer having both electron injection and electron transport capabilities (hereinafter, "E-functional layer").

For example, the organic layer may be an electron transport layer.

In some example embodiments, the organic layer may include an electron injection layer, an electron transport layer, an emission layer, a hole injection layer, a hole transport layer, or a functional layer having both hole injection and transport capabilities; and the emission layer may include an anthracene-based compound, an arylamine-based compound or a styryl-based compound.

In some other embodiments, the organic layer may include an electron injection layer, an electron transport layer, an emission layer, a hole injection layer, a hole transport layer, or a functional layer having both hole injection and transport capabilities; at least one of a red emission layer, a green emission layer, a blue emission layer, and a white emission layer of the emission layer may include a phosphorescent compound; and at least one of the hole injection layer, the hole transport layer, and the functional layer having both hole injection and hole transport capabilities may include a charge-generating material. In some example embodiments, the charge-generating material may be a p-type dopant, and the p-type dopant may be a quinine derivative, a metal oxide, or a cyano group-containing compound.

In some example embodiments, the organic layer may include an electron transport layer, and the electron transport layer may include an electron-transporting organic compound and a metal complex. The metal complex may be a lithium (Li) complex.

The term "organic layer" as used herein refers to a single layer and/or a plurality of layers disposed between the first and second electrodes of the organic light-emitting device.

The organic layer may include an emission layer, and the emission layer may include the compound of Formula 1 described above. The organic layer may include at least one of a hole injection layer, a hole transport layer, and a functional layer having both hole injection and hole transport capabilities (hereinafter, "H-functional layer"); and at least one of the hole injection layer, the hole transport layer, and the functional layer having both hole injection and hole transport capabilities may include the compound of Formula 1.

FIG. 1 illustrates a schematic sectional view of an organic light-emitting device according to an example embodiment.

Hereinafter, a structure of an organic light-emitting device according to an example embodiment and a method of manufacturing the same will now be described with reference to FIG. 1.

A substrate (not shown) may be a suitable substrate for organic light emitting devices. In some example embodiments the substrate may be a glass substrate or a transparent plastic substrate with strong mechanical strength, thermal stability, transparency, surface smoothness, ease of handling, and water resistance.

The first electrode may be formed by depositing or sputtering a first electrode-forming material on the substrate. When the first electrode is an anode, a material having a high work function may be used as the first electrode-forming material to facilitate hole injection. The first electrode may be a reflective electrode or a transmission electrode.

Transparent and conductive materials such as ITO, IZO, $SnO_2$, and ZnO may be used to form the first electrode. The first electrode may be formed as a reflective electrode using magnesium (Mg), aluminum (Al), aluminum-lithium (Al—Li), calcium (Ca), magnesium-indium (Mg—In), magnesium-silver (Mg—Ag), or the like.

The first electrode may have a single-layer structure or a multi-layer structure including at least two layers. For example, the first electrode may have a three-layered structure of ITO/Ag/ITO, etc.

An organic layer(s) is disposed on the first electrode.

The organic layer may include one or more of a hole injection layer (HIL), a hole transport layer (HTL), a buffer layer (not shown), an emission layer (EML), an electron transport layer (ETL), or an electron injection layer (EIL).

The HIL may be formed on the first electrode by vacuum deposition, spin coating, casting, Langmuir-Blodgett (LB) deposition, or the like.

When the Hill is formed using vacuum deposition, vacuum deposition conditions may vary according to the compound that is used to form the HIL, and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Å/sec.

When the HIL is formed using spin coating, the coating conditions may vary according to the compound that is used to form the HIL, and the desired structure and thermal properties of the HIL to be formed. For example, the coating rate may be in the range of about 2,000 rpm to about 5,000 rpm, and a temperature at which heat treatment is performed to remove a solvent after coating may be in the range of about 80° C. to about 200° C.

The HIL may be formed of a suitable material for a HIL. Some examples of the material that may be used to form the HIL are N,N'-diphenyl-N,N'-bis-[4-(phenyl-m-tolyl-amino)-phenyl]-biphenyl-4,4'-diamine, (DNTPD), a phthalocyanine compound such as copper phthalocyanine, 4,4',4"-tris(3-methylphenylphenylamino)triphenylamine (m-MTDATA), N,N'-di(I-naphthyl)-N,N'-diphenylbenzidine (NPB), TDATA, 2T-NATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline)/poly(4-styrene-sulfonate (PANI/PSS).

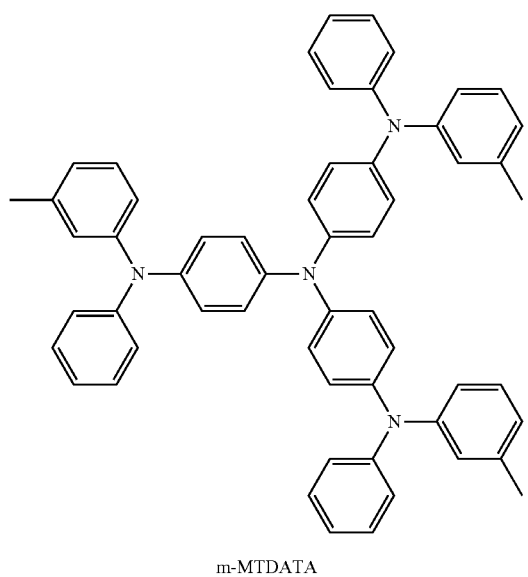

m-MTDATA

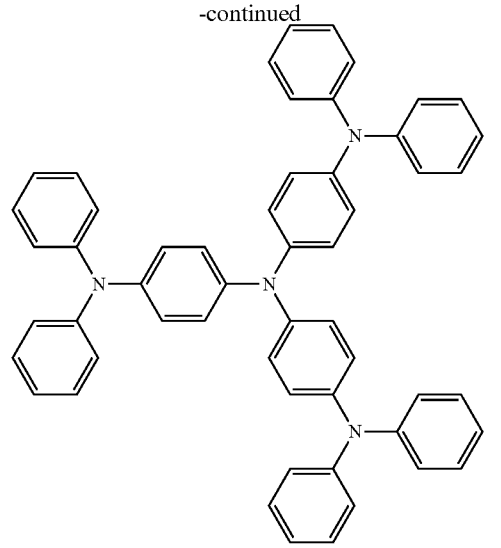

TDATA

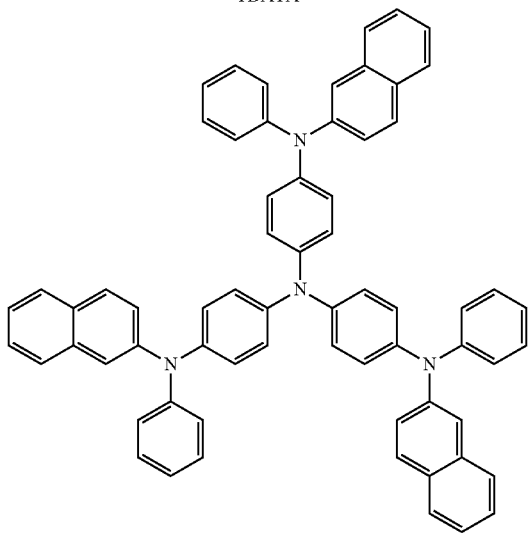

2-TNATA

The thickness of the HIL may be about 100 Å to about 10,000 Å, e.g., about 100 Å to about 1,000 Å. When the thickness of the HIL is within these ranges, the HIL may have good hole injecting ability without a substantial increase in driving voltage.

An HTL may be formed on the HIL by using vacuum deposition, spin coating, casting, Langmuir-Blodgett (LB) deposition, or the like. When the HTL is formed using vacuum deposition or spin coating, the conditions for deposition and coating may be similar to those for the formation of the HIL, though the conditions for the deposition and coating may vary according to the material that is used to form the HTL.

The HTL may be formed of suitable hole-transporting materials. Some examples of suitable HTL forming materials are carbazole derivatives, such as N-phenylcarbazole or polyvinylcarbazole, N,N'-bis(3-methylphenyl)-N,N'-diphenyl-[1,1-biphenyl]-4,4'-diamine (TPD), 4,4',4"-tris(N-carbazolyl)triphenylamine (TCTA), and N,N'-di(1-naphthyl)-N,N'-diphenylbenzidine) (NPB).

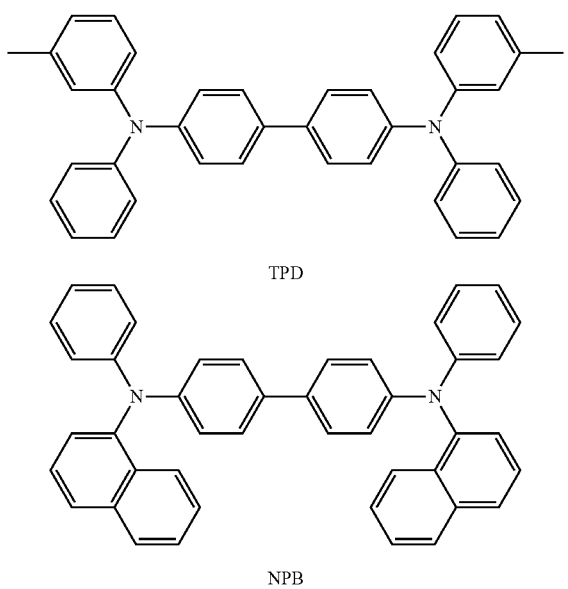

TPD

NPB

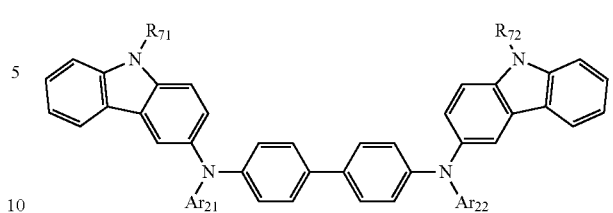

<Formula 350>

The thickness of the HTL may be from about 50 Å to about 2,000 Å, e.g., about 100 Å to about 1,500 Å. When the thickness of the HTL is within these ranges, the HTL may have good hole transporting ability without a substantial increase in driving voltage.

The H-functional layer (having both hole injection and hole transport capabilities) may contain at least one material from each group of the hole injection layer materials and hole transport layer materials. The thickness of the H-functional layer may be from about 500 Å to about 10,000 Å, e.g., about 100 Å to about 1,000 Å. When the thickness of the H-functional layer is within these ranges, the H-functional layer may have good hole injection and transport capabilities without a substantial increase in driving voltage.

In some example embodiments, at least one of the HIL, HTL, and H-functional layer may include at least one of a compound of Formula 300 below and a compound of Formula 350 below:

<Formula 300>

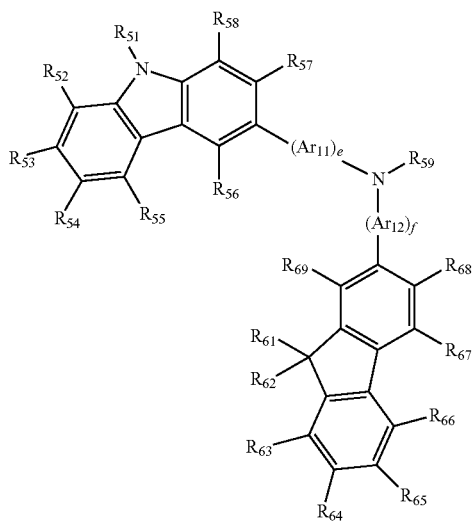

In Formulae 300 and 350, $Ar_{11}$, $Ar_{12}$, $Ar_2$, and $Ar_{22}$ may each independently be a substituted or unsubstituted $C_6$-$C_{60}$ arylene group.

In Formula 300, e and f may each independently be an integer from 0 to 5, for example, may be 0, 1, or 2. As an example, e may be 1, and f may be 0.

In Formulae 300 and 350 above, $R_{51}$ to $R_{58}$, $R_{61}$ to $R_{69}$, and $R_{71}$ and $R_{72}$ may each independently be a hydrogen atom, a deuterium atom, a halogen atom, a hydroxyl group, a cyano group, a nitro group, an amino group, an amidino group, a hydrazine group, a hydrazone, a carboxyl group or a salt thereof, a sulfonic acid group or a salt thereof, a phosphoric acid group or a salt thereof, a substituted or unsubstituted C1-C60 alkyl group, a substituted or unsubstituted C2-C60 alkenyl group, a substituted or unsubstituted C2-C60 alkynyl group, a substituted or unsubstituted C1-C60 alkoxy group, a substituted or unsubstituted C3-C60 cycloalkyl group, a substituted or unsubstituted C6-C60 aryl group, a substituted or unsubstituted C6-C60 aryloxy group, or a substituted or unsubstituted C6-C60 arylthio group. In some example embodiments, $R_{51}$ to $R_{58}$, $R_{61}$ to $R_{69}$, $R_{71}$, and $R_{72}$ may each independently be one of a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid group or a salt thereof; a C1-C10 alkyl group (for example, a methyl group, an ethyl group, a propyl group, a butyl group, a pentyl group, a hexyl group, or the like); a C1-C10 alkoxy group (for example, a methoxy group, an ethoxy group, a propoxy group, a butoxy group, a pentoxy group, or the like); a C1-C10 alkyl group and a C1-C10 alkoxy group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, and a phosphoric acid group or a salt thereof; a phenyl group; a naphthyl group; an anthryl group; a fluorenyl group; a pyrenyl group; and a phenyl group, a naphthyl group, an anthryl group, a fluorenyl group, and a pyrenyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a C1-C10 alkyl group, and a C1-C10 alkoxy group.

In Formula 300, $R_{59}$ may be one of a phenyl group, a naphthyl group, an anthryl group, a biphenyl group, a pyridyl group; and a phenyl group, a naphthyl group, an anthryl group, a biphenyl group, and a pyridyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted C1-C20 alkyl group, and a substituted or unsubstituted C1-C20 alkoxy group.

In an embodiment the compound of Formula 300 may be a compound represented by Formula 300A below:

<Formula 300A>

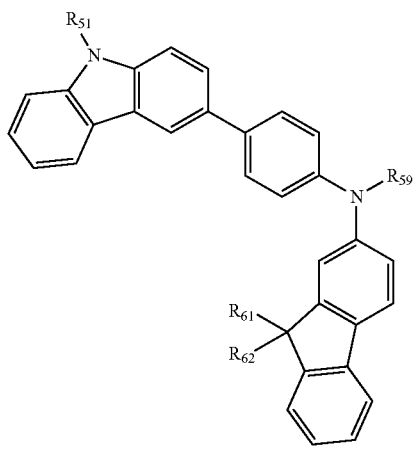

In Formula 300A, $R_{51}$, $R_{60}$, $R_{61}$, and $R_{59}$ may be as defined above.

In some example embodiments, at least one of the HIL, HTL, and H-functional layer may include at least one of compounds represented by Formulae 301 to 320 below:

301

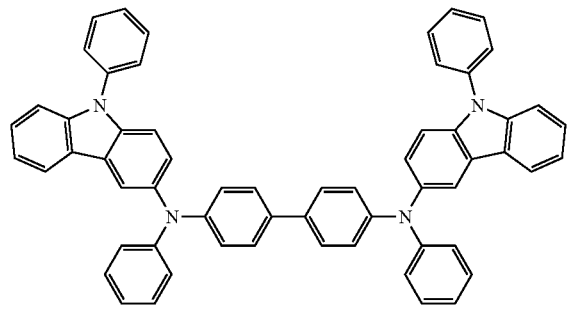

302

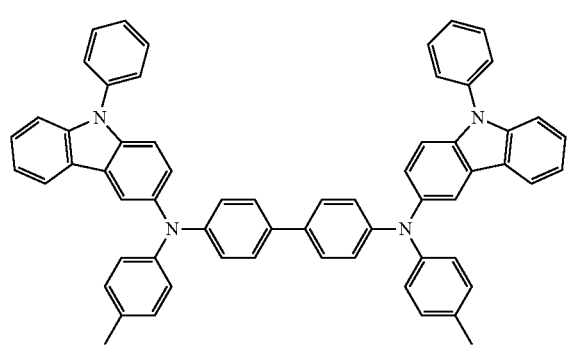

303

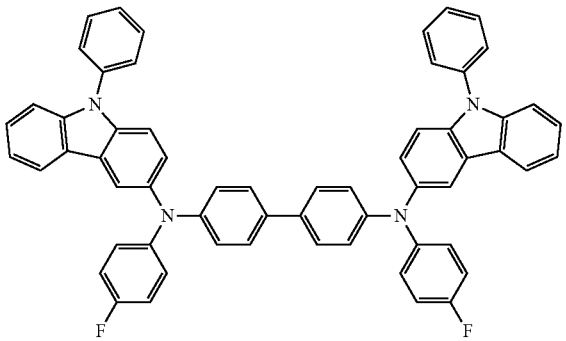

304

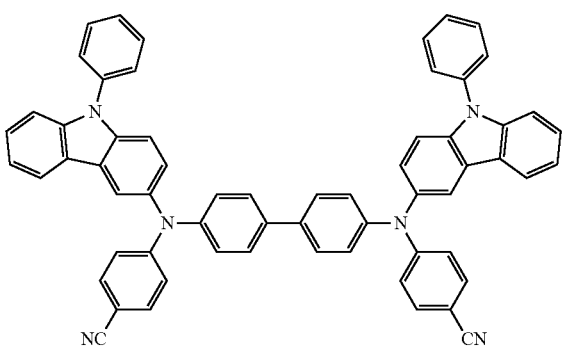

305

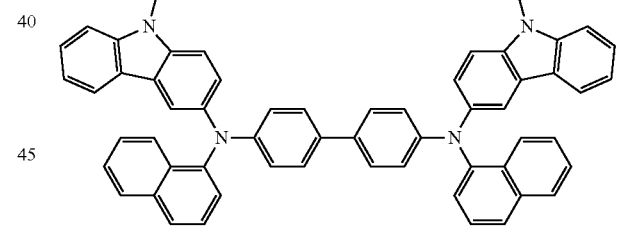

306

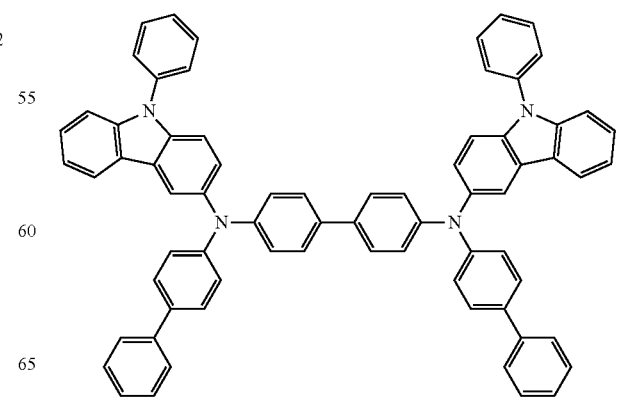

307
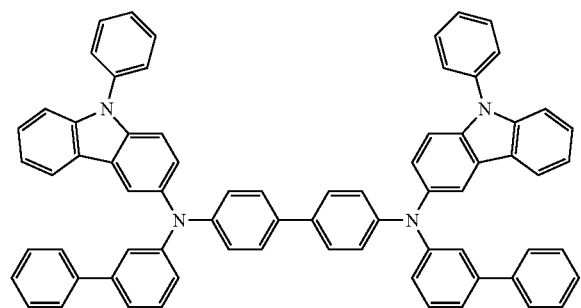
308
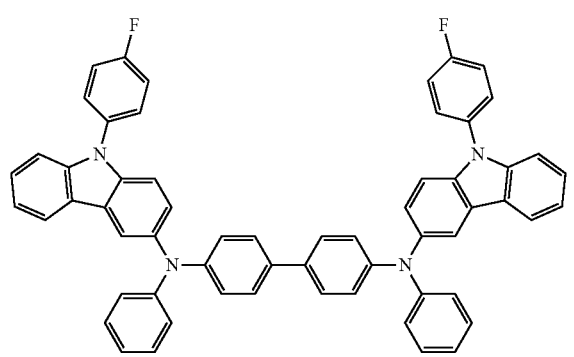
309
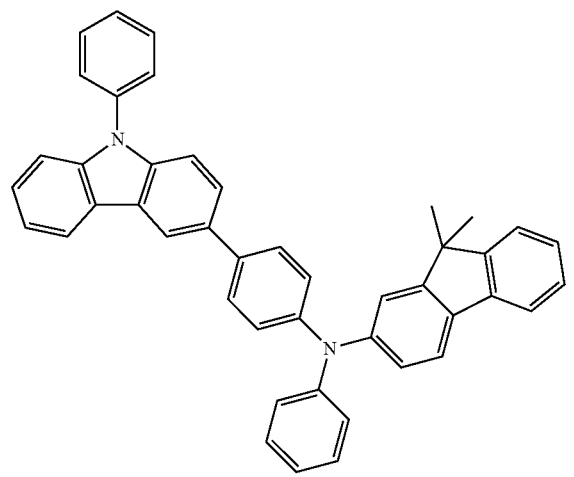
310
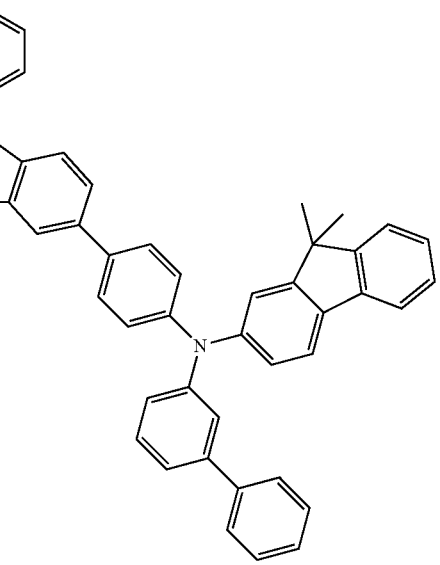
311
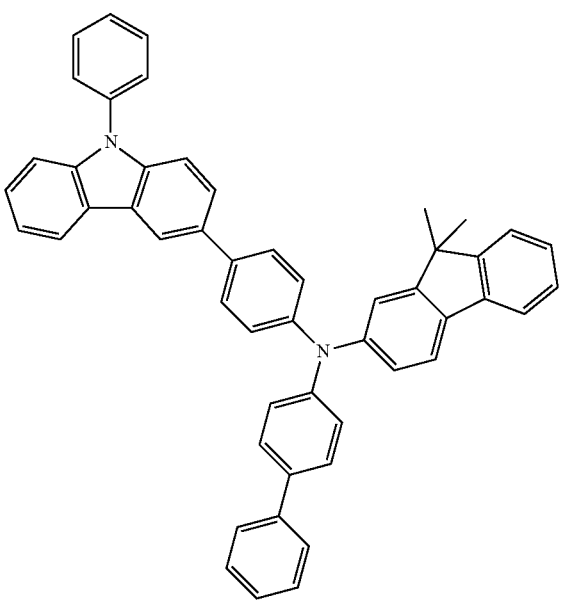

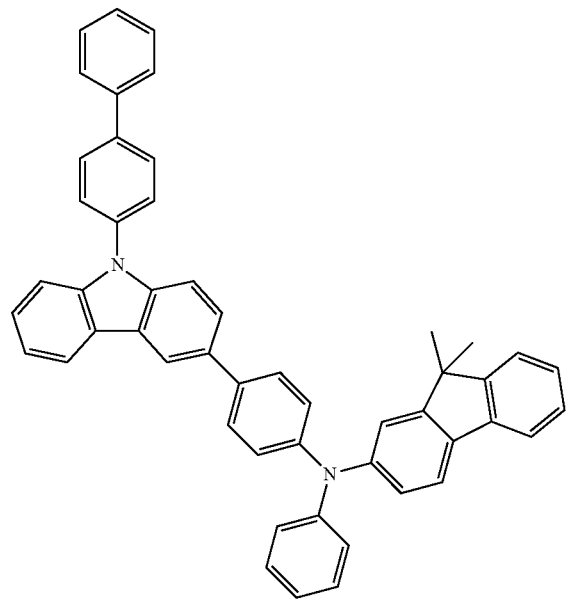
312
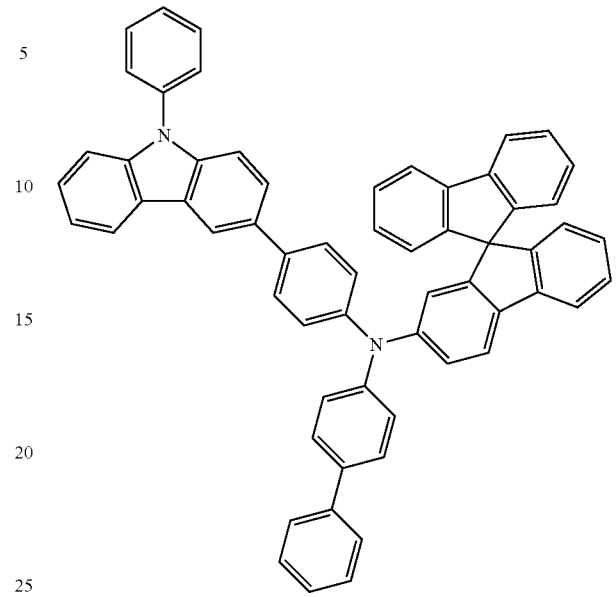
314
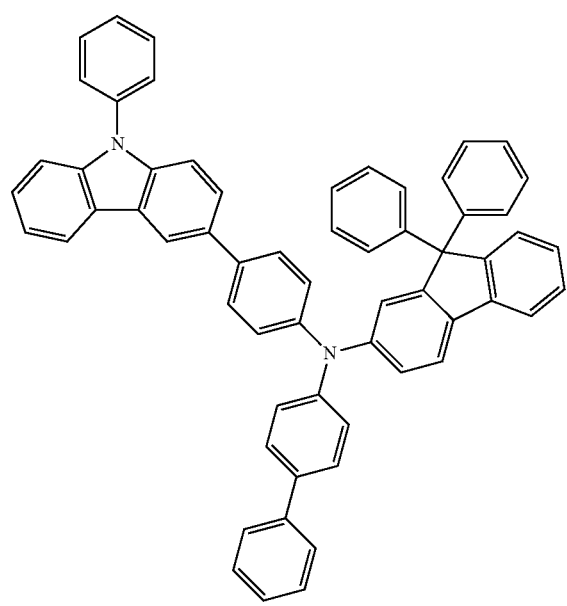
313
315

316

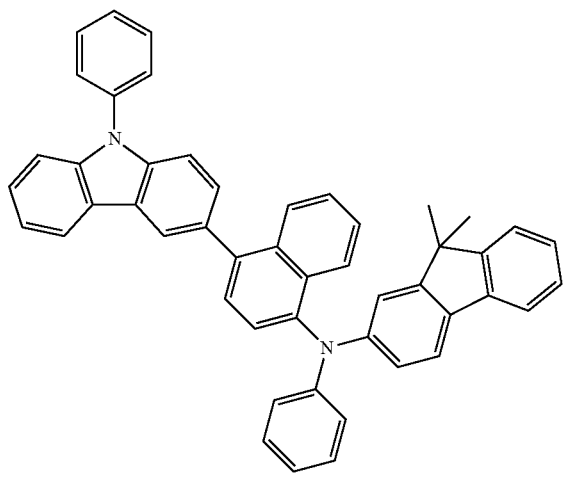

317

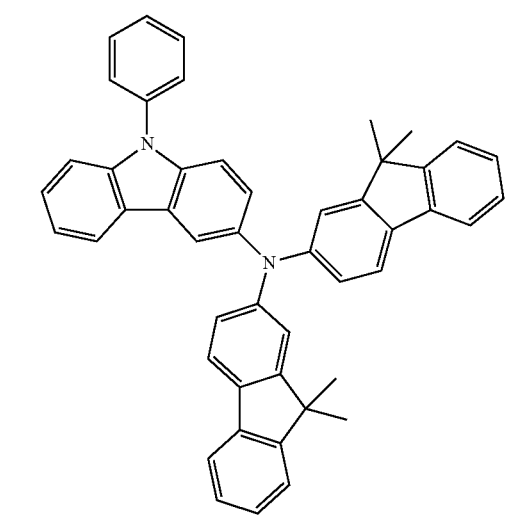

318

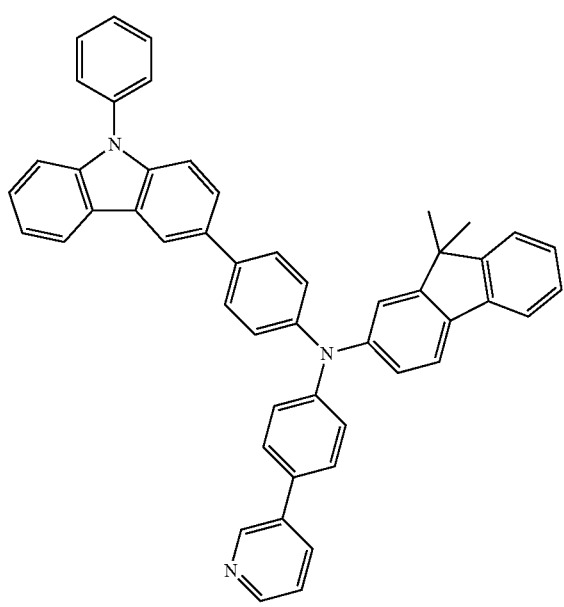

319

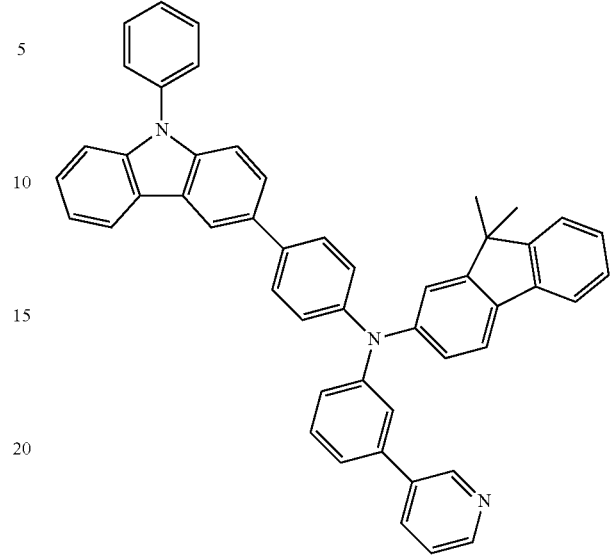

320

At least one of the HIL, HL, and H-functional layer may further include a charge-generating material for improved layer conductivity, in addition to a hole injecting material, hole transport material, and/or material having both hole injection and hole transport capabilities as described above.

The charge-generating material may be, for example, a p-dopant. The p-dopant may be one of quinine derivatives, metal oxides, compounds with a cyano group, etc. Some examples of the p-dopant are quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and cyano-containing compounds such as Compound 200 below.

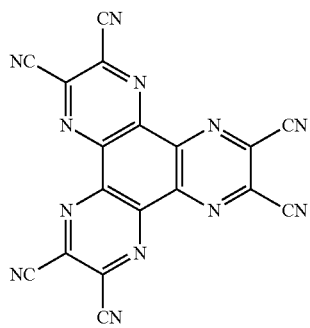

<Compound 200>

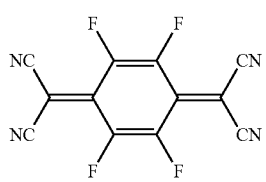

<F4-TCNQ>

When the hole injection layer, hole transport layer, or H-functional layer further includes a charge-generating material, the charge-generating material may be homogeneously dispersed or inhomogeneously distributed in the layer.

A buffer layer may be disposed between at least one of the HIL, HTL, and H-functional layer, and the EML. The buffer layer may compensate for an optical resonance distance of light according to a wavelength of the light emitted from the EML, and thus may increase efficiency. The butter layer may include a suitable hole injecting material or hole transporting material. In some other embodiments, the buffer layer may include the same material as one of the materials included in the HIL, HTL, and H-functional layer that underlie the buffer layer.

An EML may be formed on the HTL, H-functional layer, or buffer layer by vacuum deposition, spin coating, casting, Langmuir-Blodget (LB) deposition, or the like. When the EML is formed using vacuum deposition or spin coating, the deposition and coating conditions may be similar to those for the formation of the HIL, though the conditions for deposition and coating may vary according to the material that is used to form the EML.

The EML may be formed using a suitable host and dopant. Some examples of the dopant for use in the EML are a fluorescent dopant or a phosphorescent dopant.

Some examples of the host are Alq$_3$, 4,4'-N,N'-dicarbazole-biphenyl (CBP), poly(n-vinylcarbazole) (PVK), 9,10-di(naphthalene-2-yl)anthracene (DNA), TCTA, 1,3,5-tris(N-phenylbenzimidazole-2-yl)benzene (TPBI), 3-tert-butyl-9,10-di-2-naphthylanthracene (TBADN), E3, distyrylarylene (DSA), dmCBP (see formula below), and Compounds 501 to 509 below.

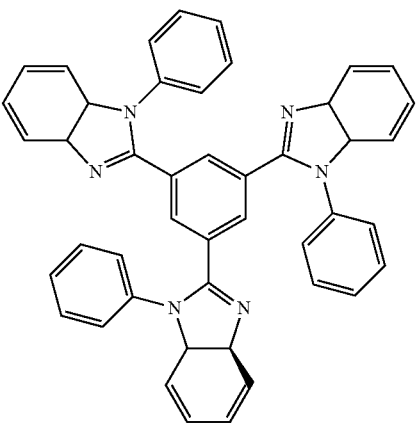

TPBI

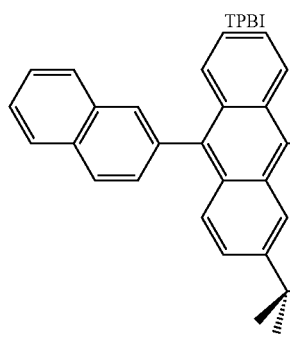

TBADN

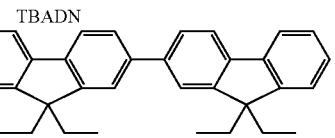

E3

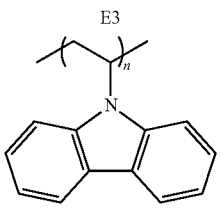

PVK

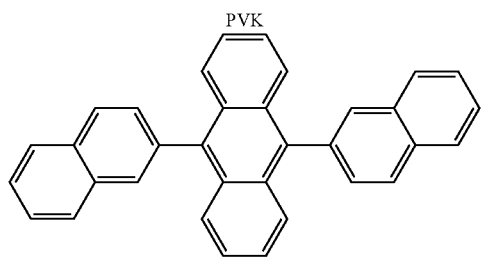

ADN

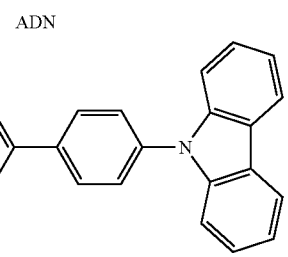

CBP

-continued
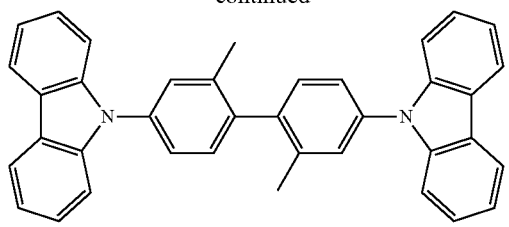
dmCBP
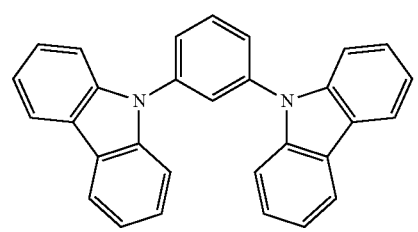
501
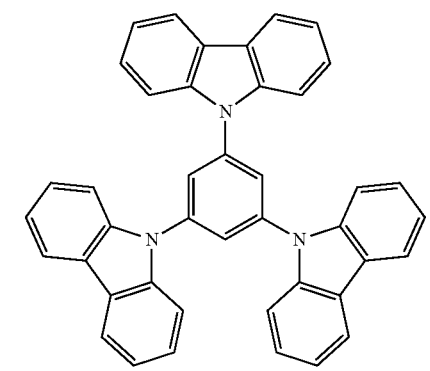
502
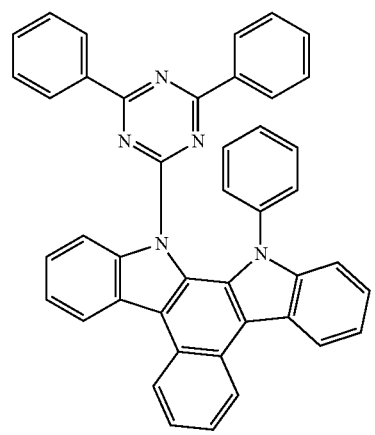
503
-continued
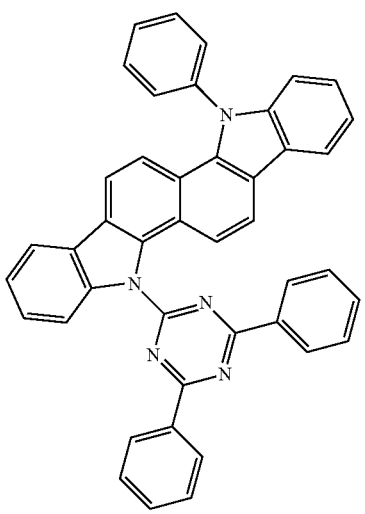
504
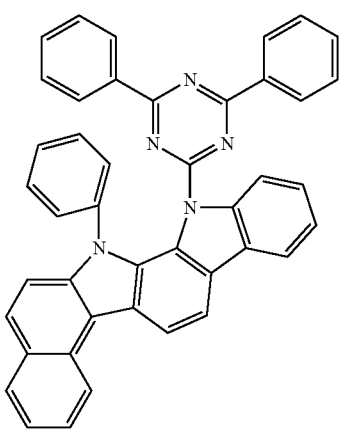
505
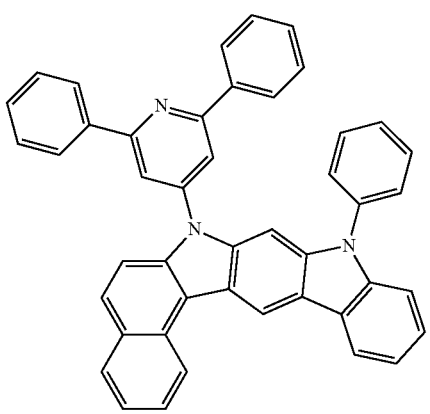
506

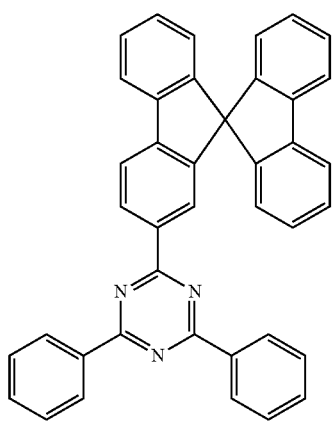

507

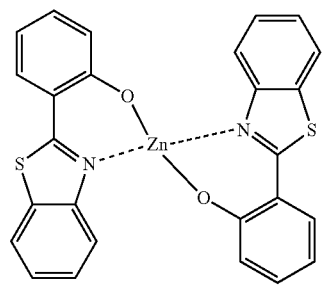

508

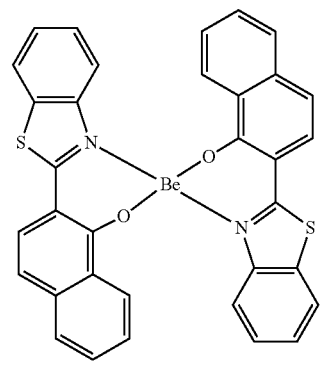

509

In some example embodiments, an anthracene-based compound represented by Formula 400 below may be used as the host.

<Formula 400>

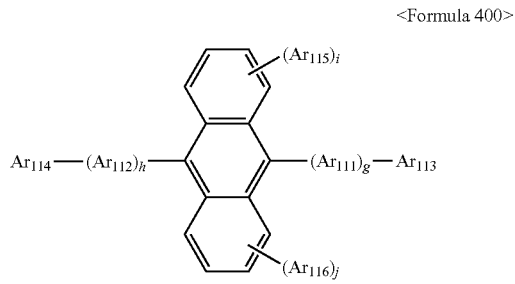

In Formula 400, $Ar_{111}$ and $Ar_{112}$ are each independently a substituted or unsubstituted C6-C60 arylene group; $Ar_{113}$ to $Ar_{116}$ are each independently a substituted or unsubstituted C1-C10 alkyl group, or a substituted or unsubstituted C6-C60 aryl group; and g, h, I, and j are each independently an integer from 0 to 4.

In some example embodiments, $Ar_{111}$ and $Ar_{112}$ in Formula 400 may each independently be a phenylene group, a naphthylene group, a phenanthrenylene group, or a pyrenylene group; or a phenylene group, a naphthylene group, a phenanthrenylene group, a fluorenyl group, or a pyrenylene group that are substituted with at least one of a phenyl group, a naphthyl group, and an anthryl group.

In Formula 400 above, g, h, I, and j may each independently be 0, 1, or 2.

In some example embodiments, $Ar_{113}$ to $Ar_{116}$ in Formula 400 may each independently be one of a C1-C10 alkyl group substituted with at least one of a phenyl group, a naphthyl group, and an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, and a fluorenyl group that are substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a C1-C60 alkyl group, a C2-C60 alkenyl group, a C2-C60 alkynyl group, a C1-C60 alkoxy group, a phenyl group, a naphthyl group, an anthryl group, a pyrenyl group, a phenanthrenyl group, a fluorenyl group, and

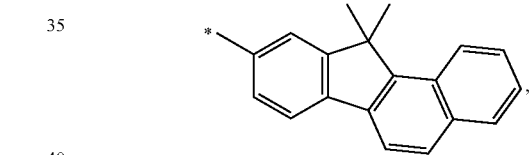

etc.

For example, the anthracene-based compound of Formula 400 above may be one of the compounds represented by the following formulae:

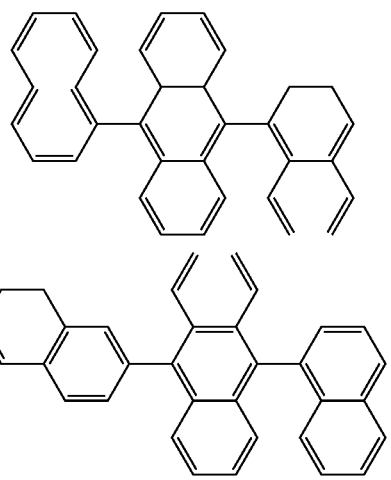

59
-continued
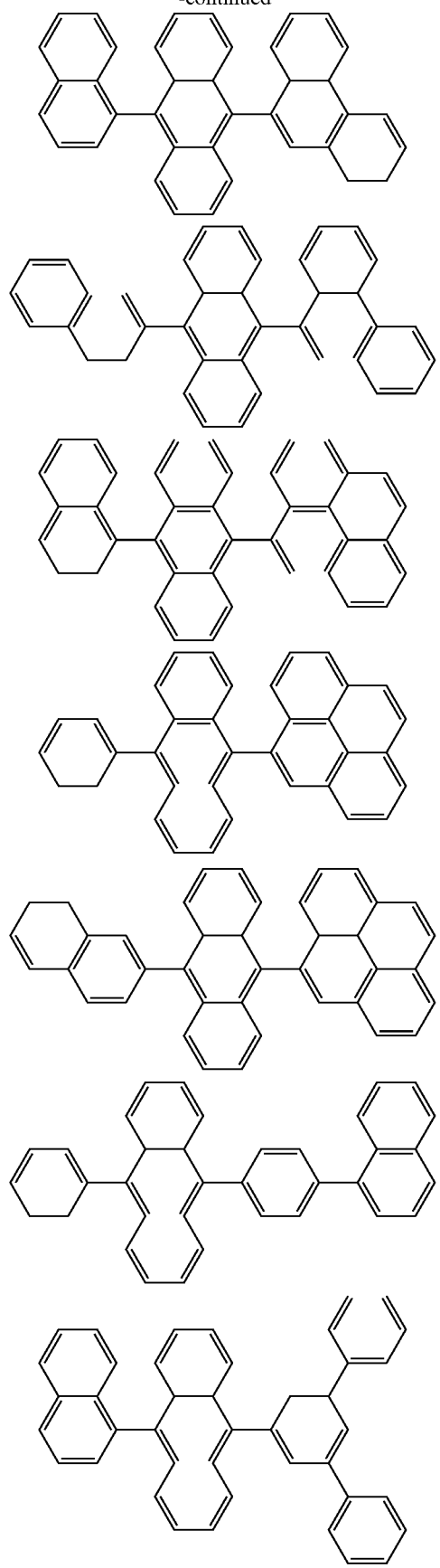
60
-continued
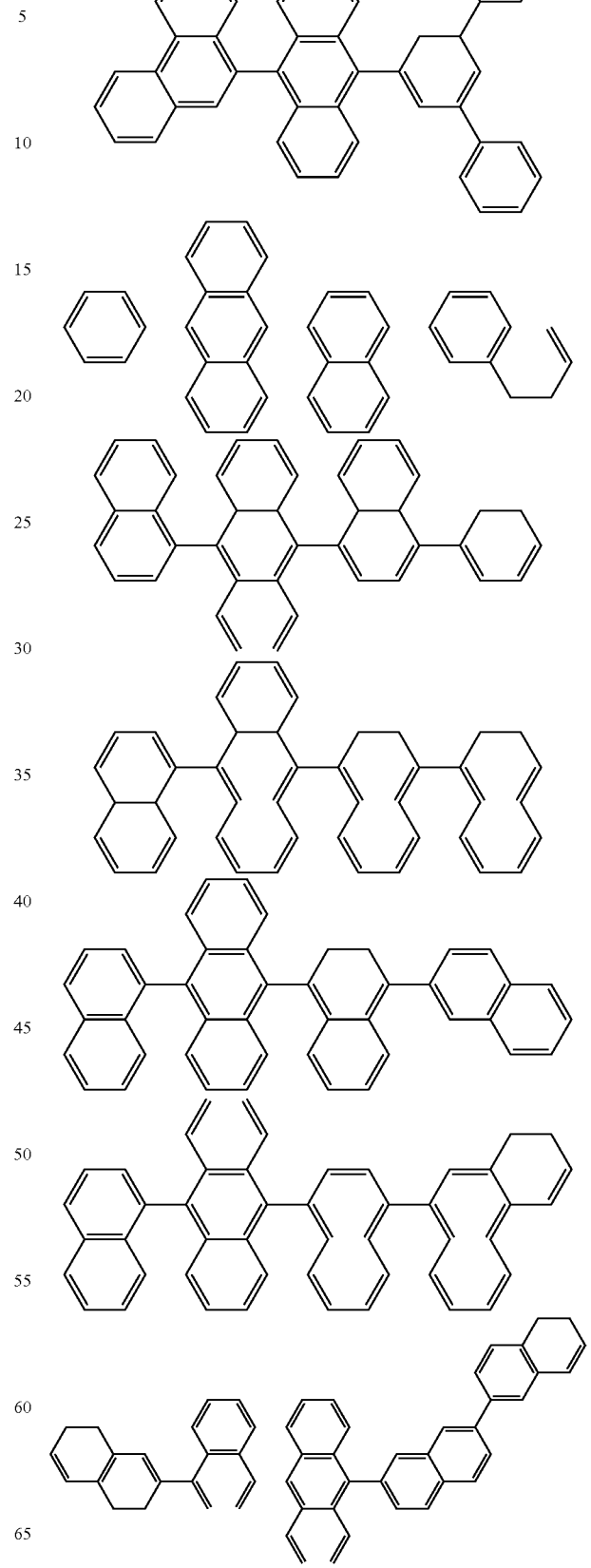

-continued
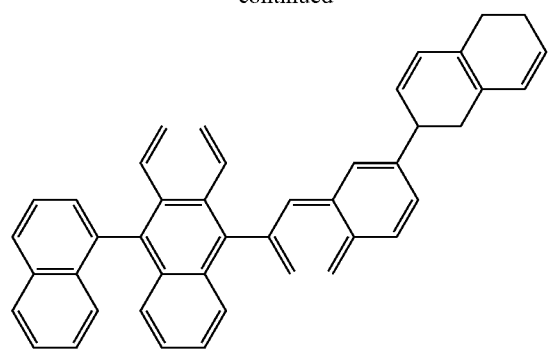
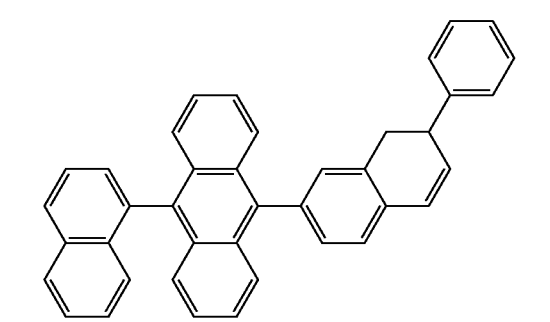
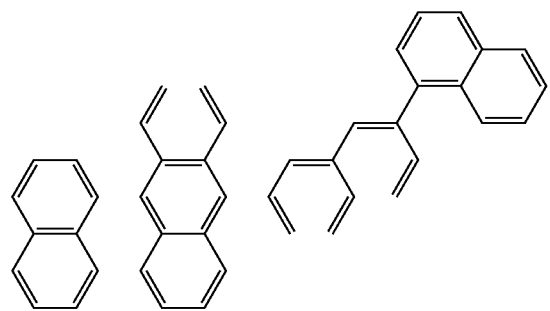
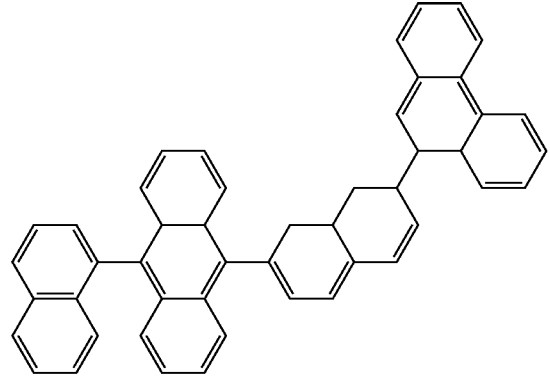
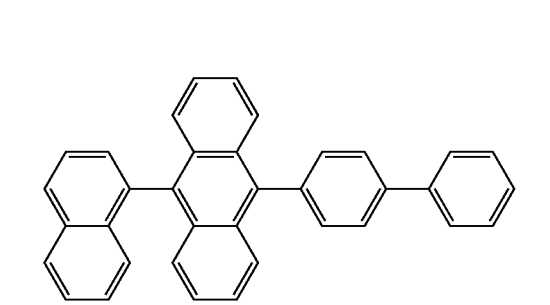
-continued
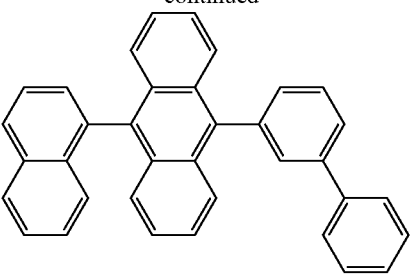
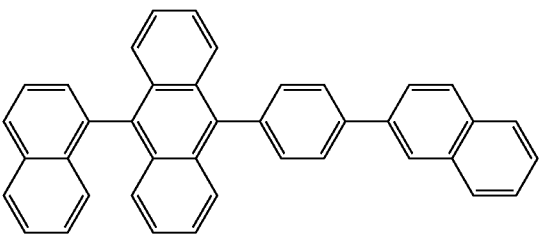
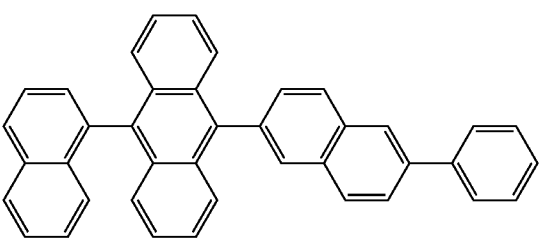
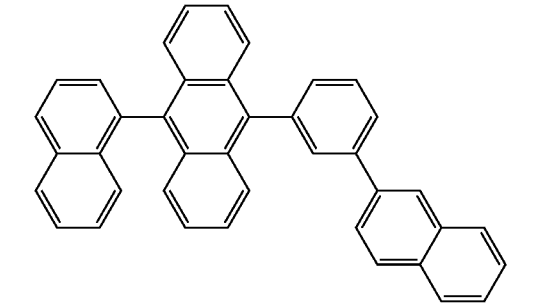
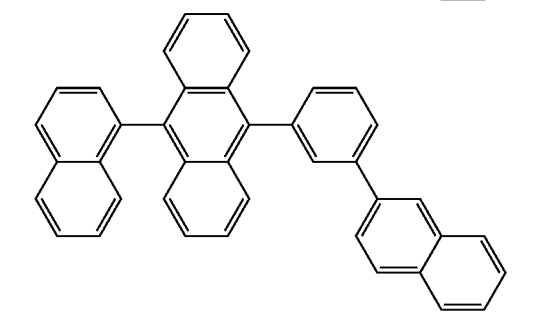
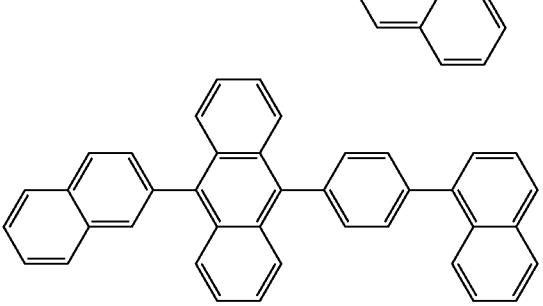

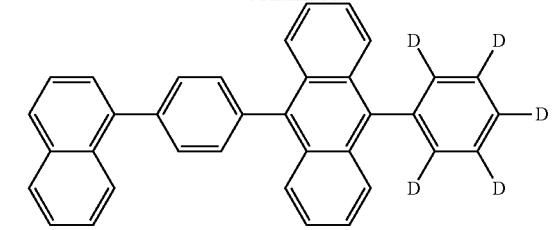
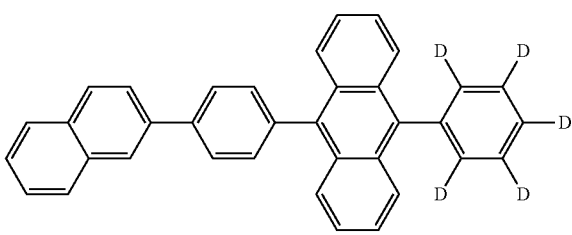
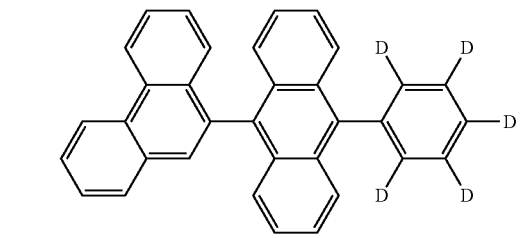
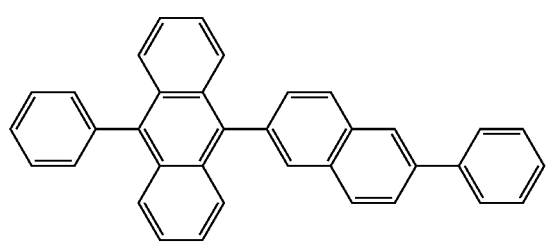
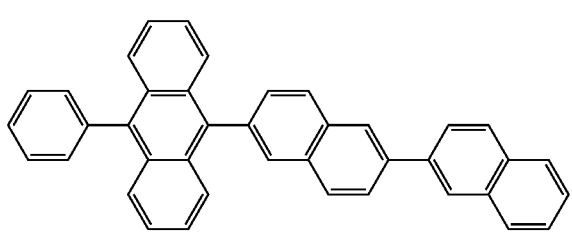
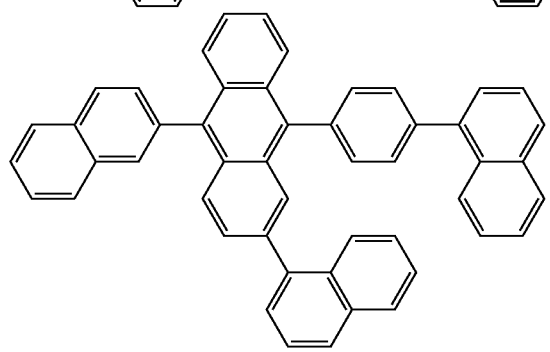
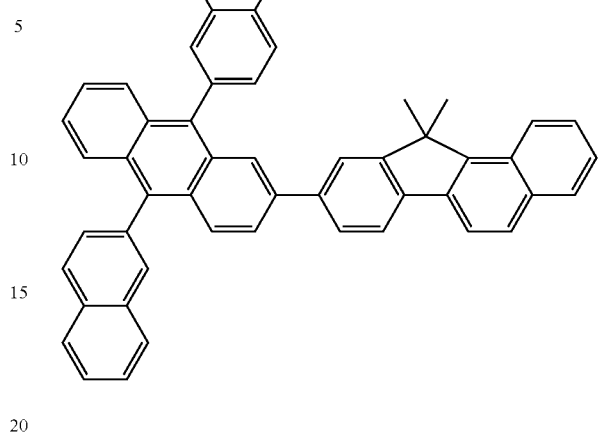
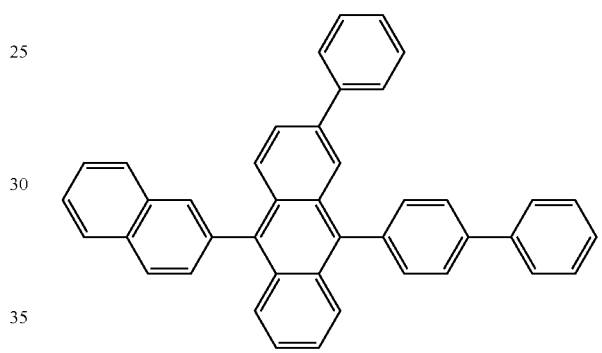
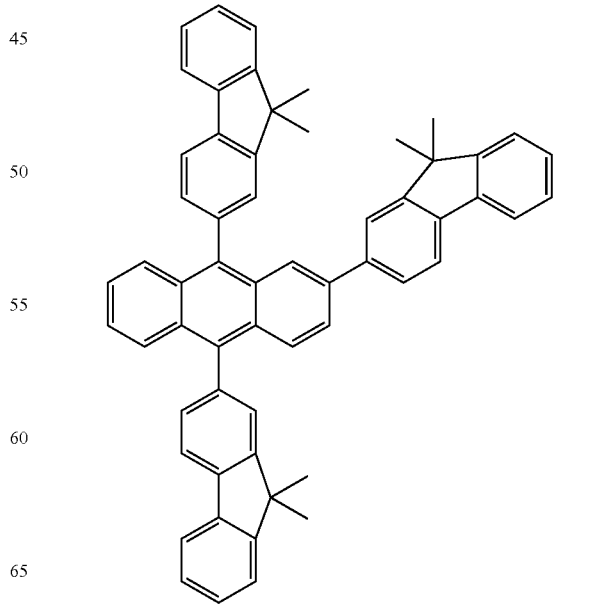

-continued

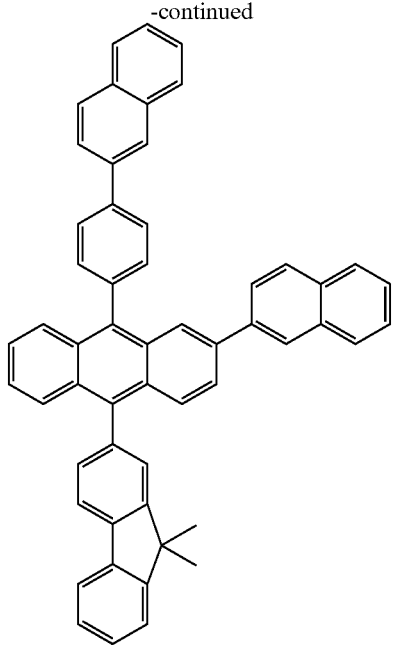

In some other embodiments, an anthracene-based compound represented by Formula 401 below may be used as the host.

<Formula 401>

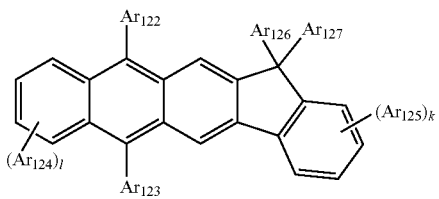

$Ar_{122}$ to $Ar_{125}$ in Formula 401 above may be defined as described above in conjunction with $Ar_{113}$ of Formula 400, and thus details thereof will not be repeated here.

$Ar_{126}$ and $Ar_{127}$ in Formula 401 above may each independently be a C1-C10 alkyl group, for example, a methyl group, an ethyl group, or a propyl group.

In Formula 401, k and l may each independently be an integer from 0 to 4, for example, 0, 1, or 2.

For example, the anthracene compound of Formula 401 above may be one of the compounds represented by the following formulae:

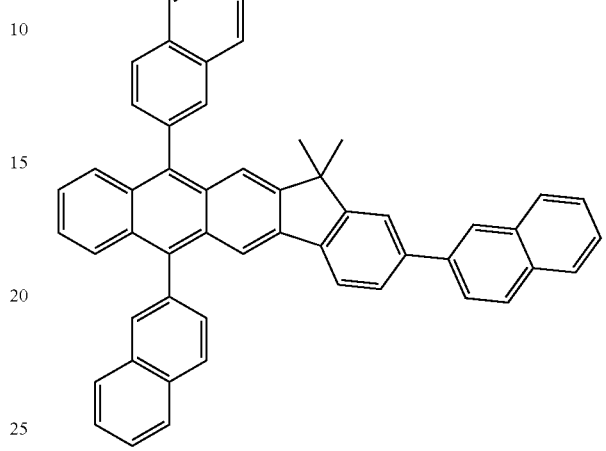

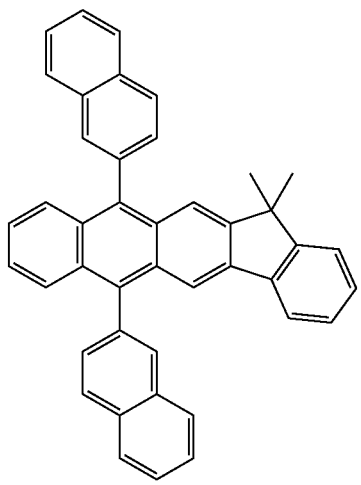

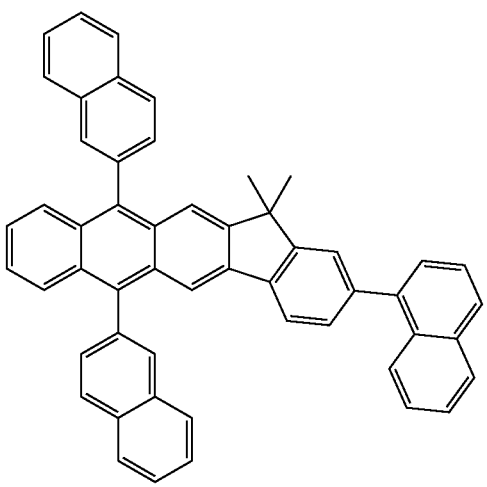

-continued

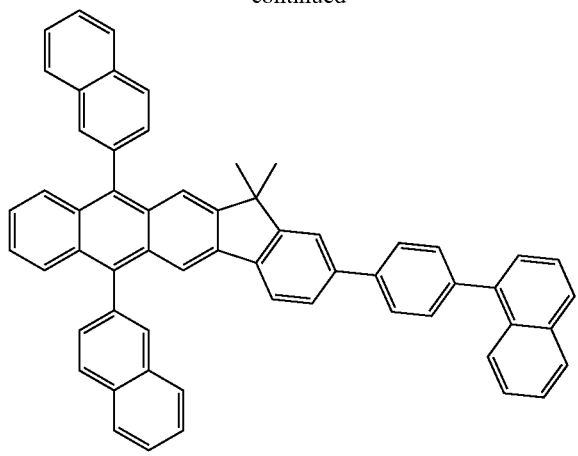

When the organic light-emitting device is a full-color organic light-emitting device, the emission layer may be patterned into a red emission layer, a green emission layer, and a blue emission layer.

At least one of the red EML, the green EML, and the blue EML may include a dopant as shown below (ppy=phenylpyridine).

Some examples of the blue dopant are compounds represented by the following formulae.

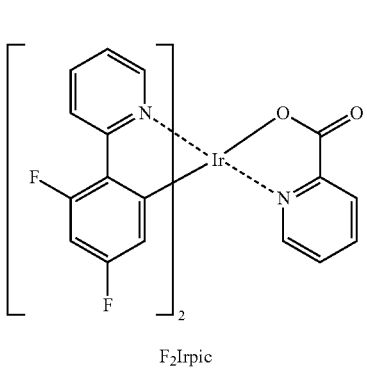
F₂Irpic

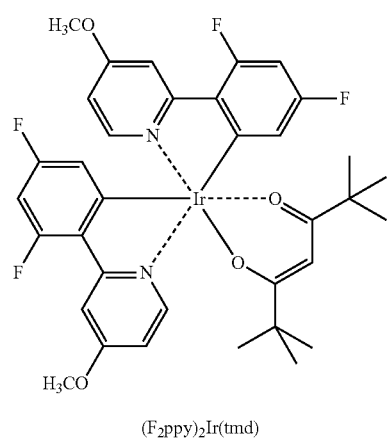
(F₂ppy)₂Ir(tmd)

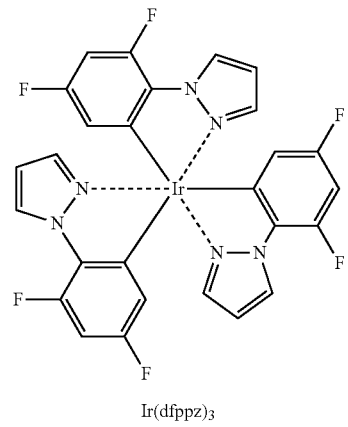
Ir(dfppz)₃

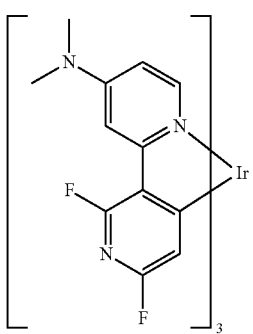

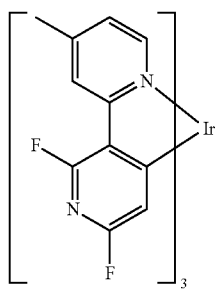

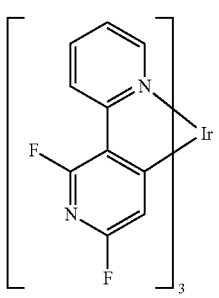

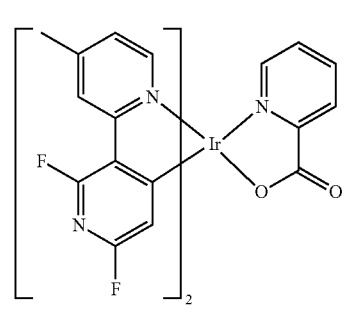

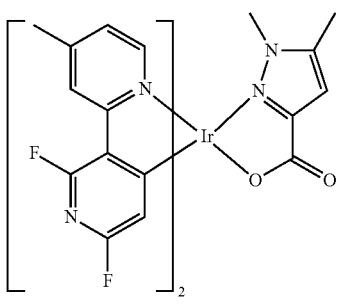

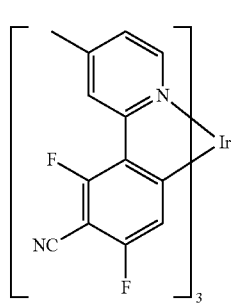

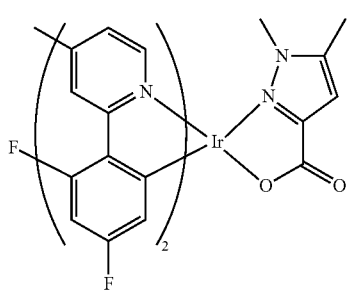

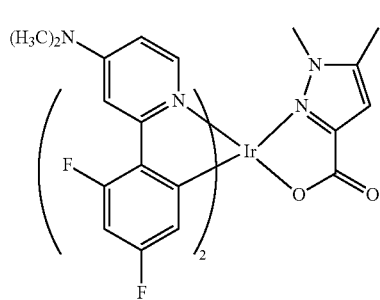
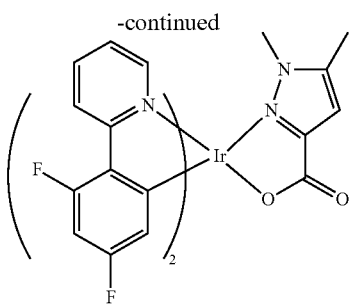
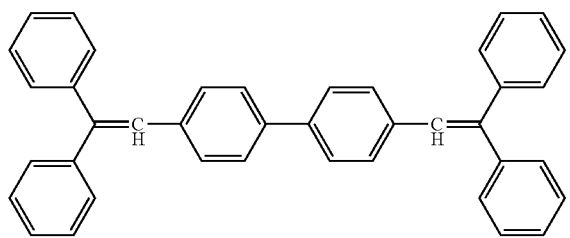
DPVBi
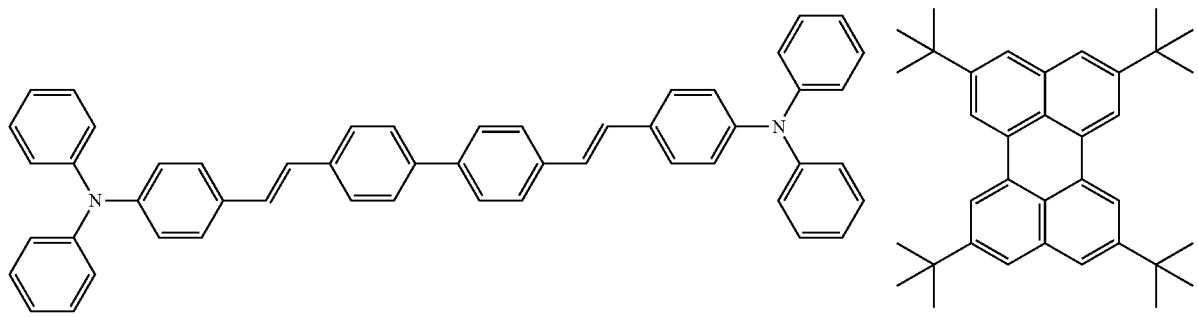
DPAVBi
TBPe
Some examples of the red dopant are compounds represented by the following formulae.
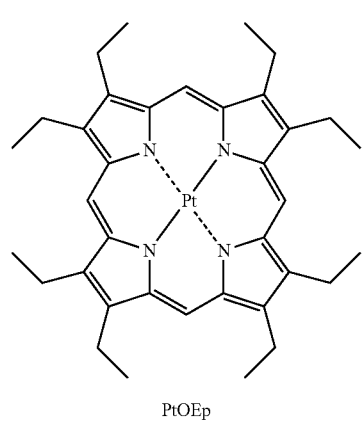
PtOEp
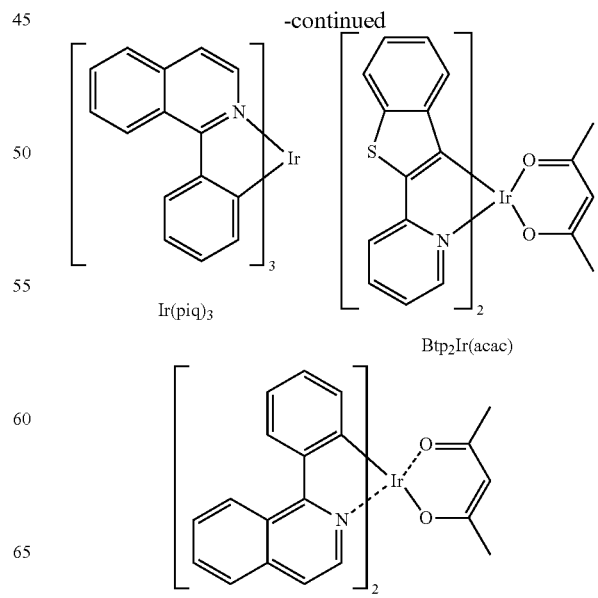
Ir(piq)₃
Btp₂Ir(acac)

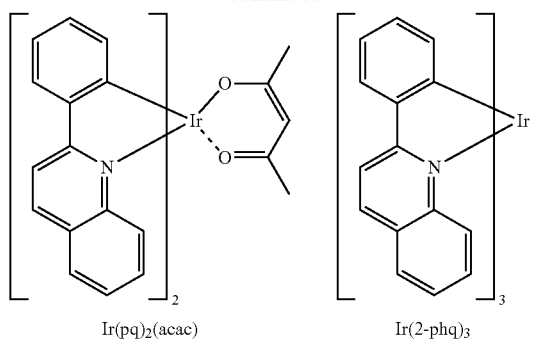
Ir(pq)₂(acac)
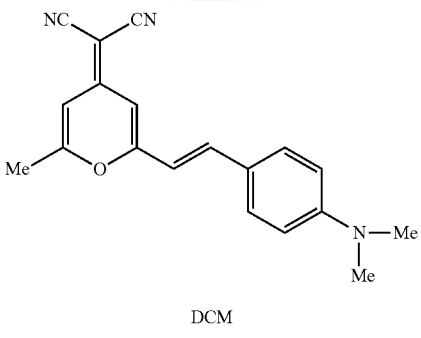
Ir(2-phq)₃
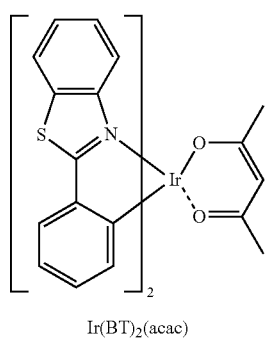
Ir(BT)₂(acac)
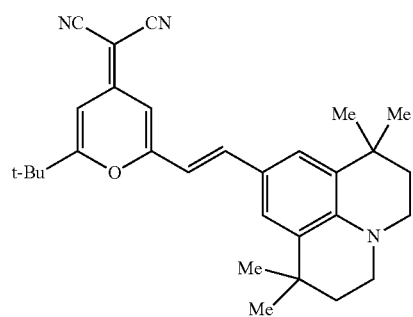
DCM
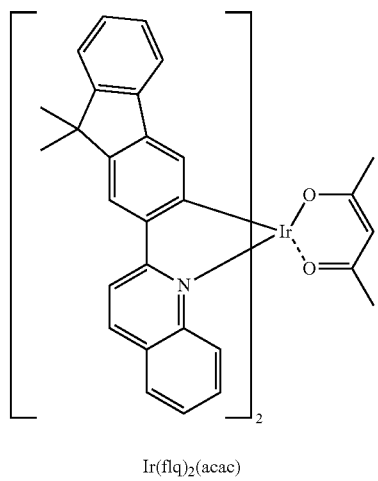
Ir(flq)₂(acac)
DCJTB
Some examples of the green dopant are compounds represented by the following formulae.
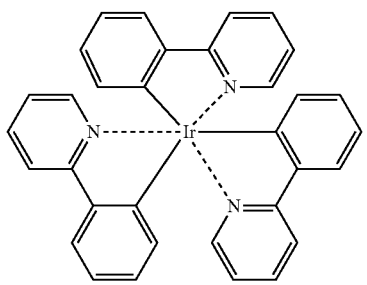
Ir(ppy)₃
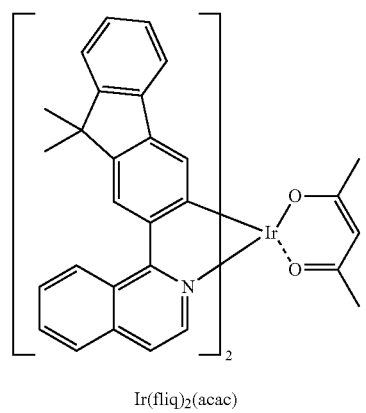
Ir(fliq)₂(acac)
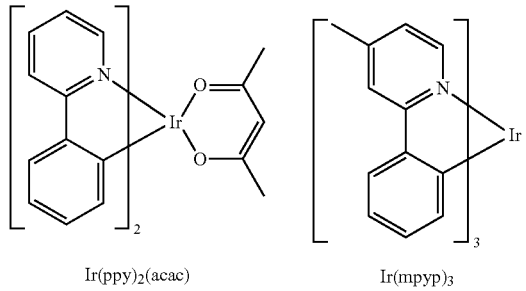
Ir(ppy)₂(acac)      Ir(mpyp)₃

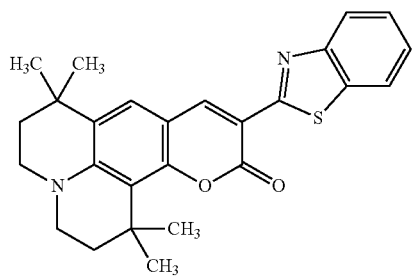
C545T
Some examples of the dopant that may be used in the EML are Pd-complex or Pt complexes represented by the following formulae.
D1
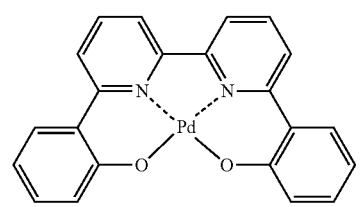
D2
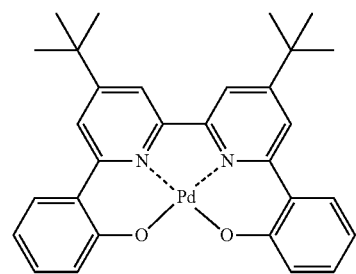
D3
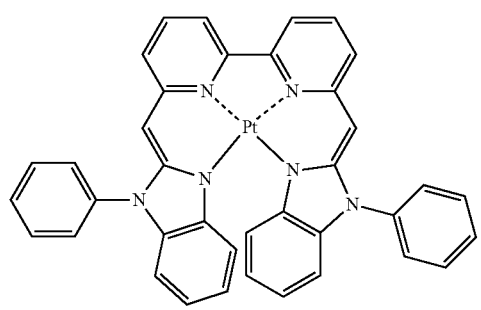
D4
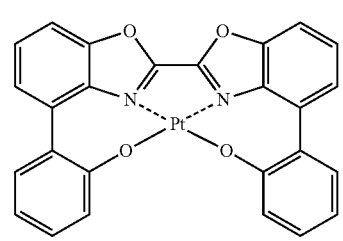
D5
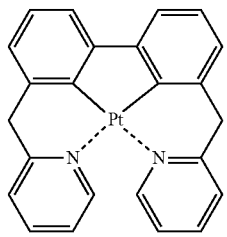
D6
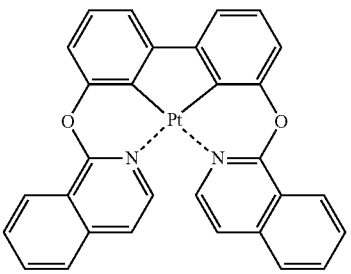
D7
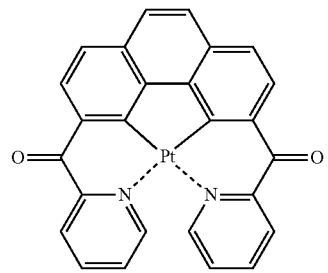
D8
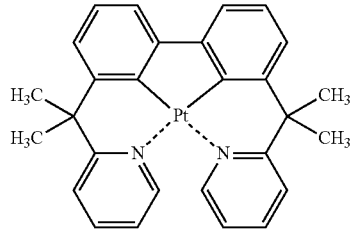
D9
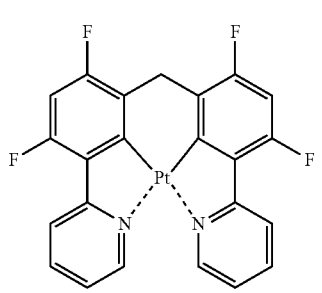
D10
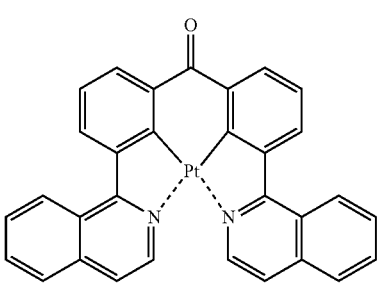

D11 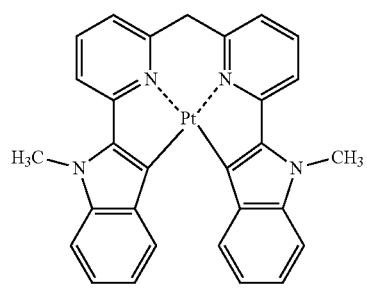
D12 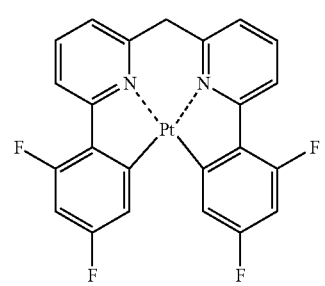
D13 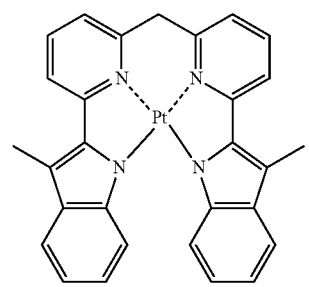
D14 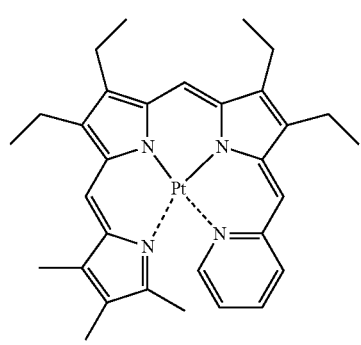
D15 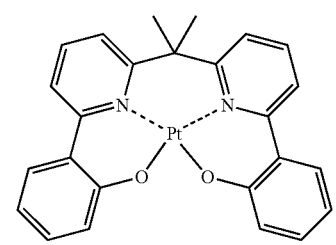
D16 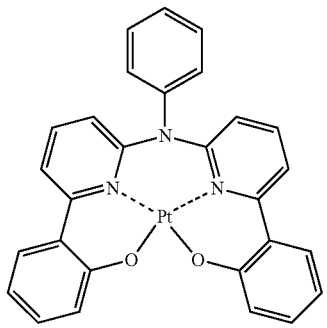
D17 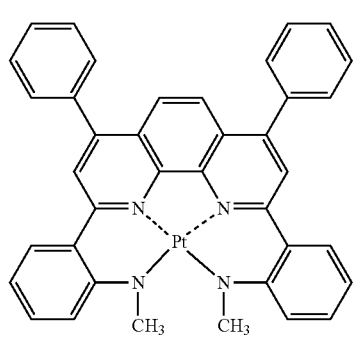
D18 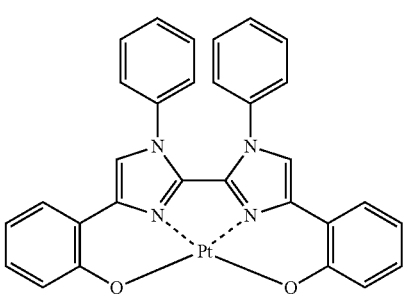
D19 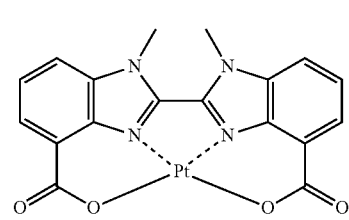
D20 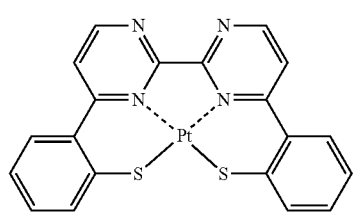

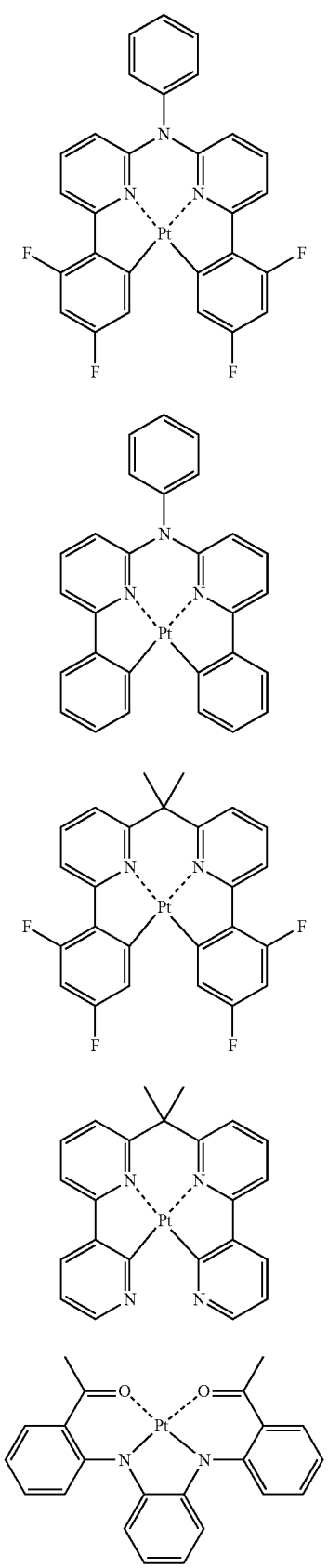

D32 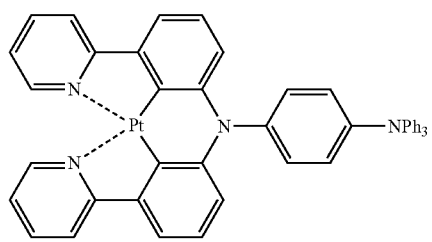
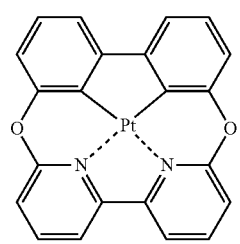
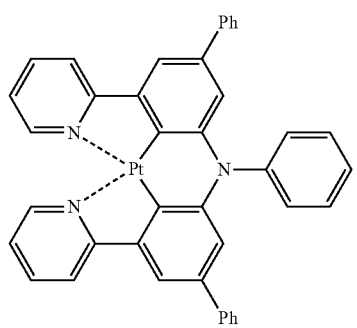
D35 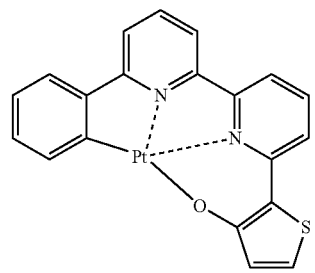
D36 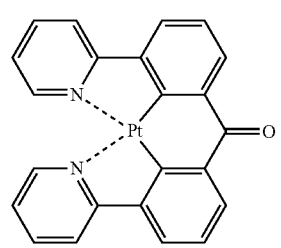
D37 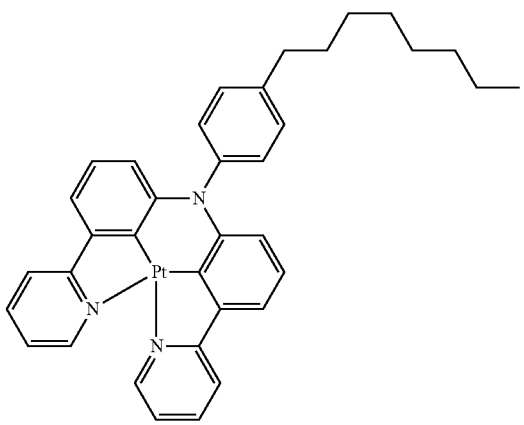
D38 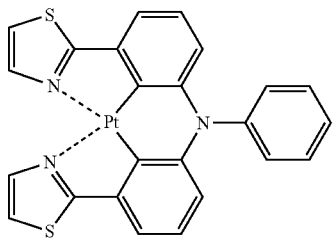
D39 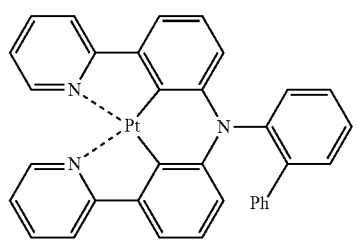
D40 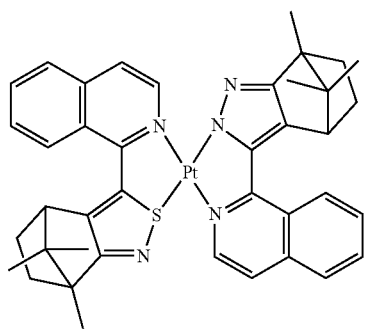
D41 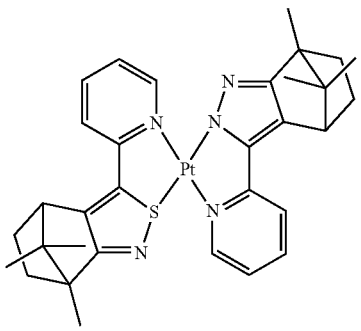

-continued
D42
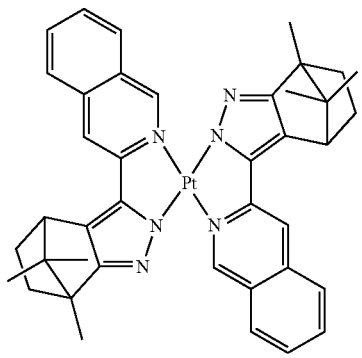
D43
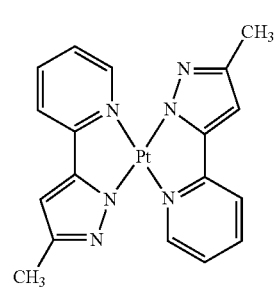
D44
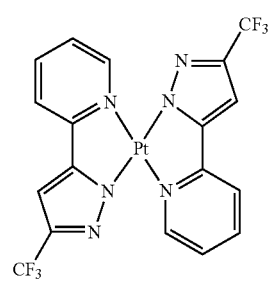
D45
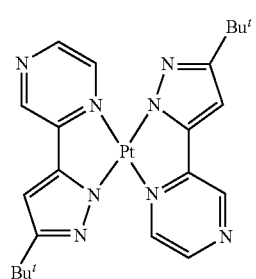
D46
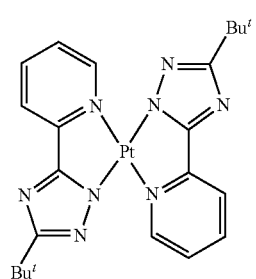
-continued
D47
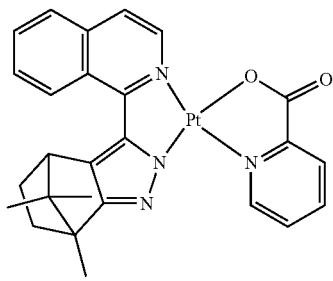
D48
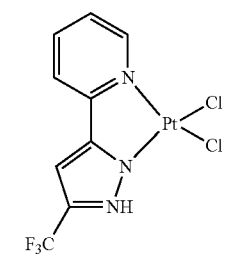
D49
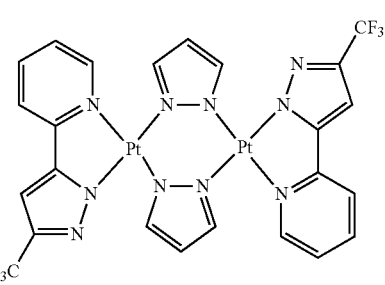
D50
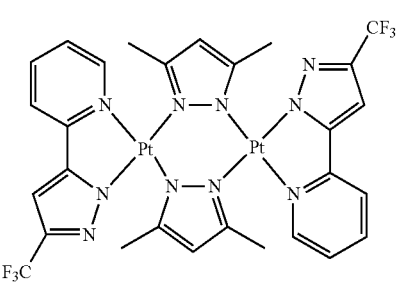
Some examples of the dopant that may be used in the EML are Os-complexes represented by the following formulae.
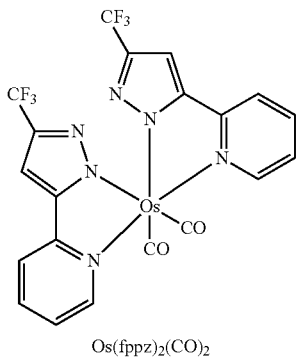
Os(fppz)$_2$(CO)$_2$ -continued

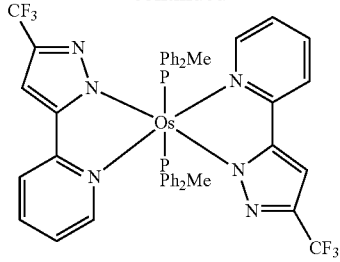
Os(fppz)₂(PPh₂Me)₂

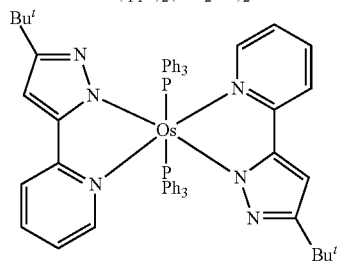
Os(bppz)₂(PPh₃)₂

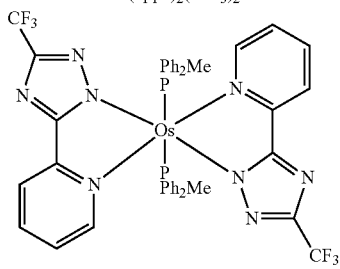
Os(fptz)₂(PPh₂Me)₂

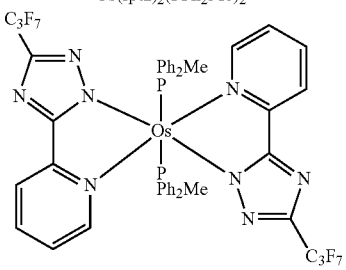
Os(hptz)₂(PPh₂Me)₂

When the EML includes both a host and a dopant, the amount of the dopant may be, e.g., from about 0.01 to about 15 parts by weight based on 100 parts by weight of the host.

The thickness of the EML may be about 100 Å to about 1,000 Å, e.g., about 200 Å to about 600 Å. When the thickness of the EML is within these ranges, the EML may have good light emitting ability without a substantial increase in driving voltage.

An ETL may be formed on the EML by vacuum deposition, spin coating, casting, or the like. When the ETL is formed using vacuum deposition or spin coating, the deposition and coating conditions may be similar to those for the formation of the HIL, though the deposition and coating conditions may vary according to a compound that is used to form the ETL.

A material for forming the ETL may be the compound of Formula 1 above or a suitable material that can stably transport electrons injected from an electron injecting electrode (cathode).

Some examples of materials for forming the ETL are a quinoline derivative, such as tris(8-quinolinolate)aluminum (Alq₃), TAZ, BAlq, beryllium bis(benzoquinolin-10-olate (Bebq₂), 9,10-di(naphthalene-2-yl)anthracene (ADN), Compound 201, and Compound 202.

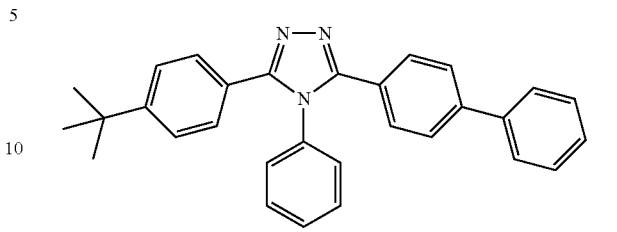

TAZ

Balq

<Compound 201>

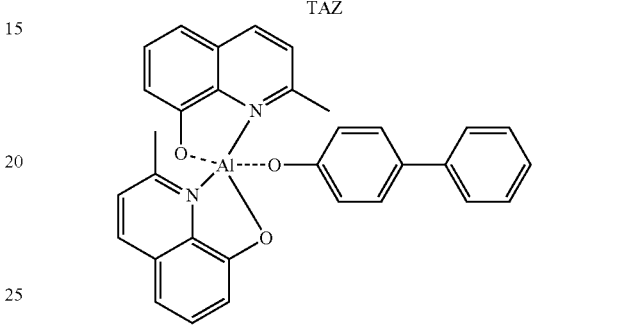

<Compound 202>

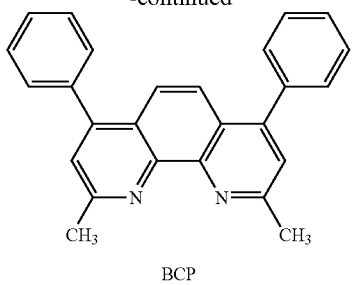

BCP

The thickness of the ETL may be from about 100 Å to about 1,000 Å, e.g., about 150 Å to about 500 Å. When the thickness of the ETL is within these ranges, the ETL may have satisfactory electron transporting ability without a substantial increase in driving voltage.

In some example embodiments the ETL may include an electron-transporting organic compound and a metal-containing material.

The metal-containing material may include a lithium (Li) complex. Some examples of the Li complex are lithium quinolate (LiQ) and Compound 203 below:

<Compound 203>

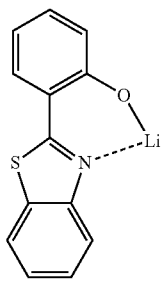

An EIL, which facilitates injection of electrons from the cathode, may be formed on the ETL. A suitable electron-injecting material may be used to form the EIL.

Some examples of materials for forming the EIL are LiF, NaCl, CsF, $Li_2O$, and BaO. The deposition and coating conditions for forming the EIL may be similar to those for the formation of the HIL, though the deposition and coating conditions may vary according to the material that is used to form the EIL.

The thickness of the EIL may be from about 1 Å to about 100 Å, e.g., about 3 Å to about 90 Å. When the thickness of the EIL is within these ranges, the EIL may have satisfactory electron injection ability without a substantial increase in driving voltage.

The second electrode is disposed on the organic layer. The second electrode may be a cathode that is an electron injection electrode. A material for forming the second electrode may be a metal, an alloy, an electro-conductive compound, which have a low work function, or a mixture thereof. In this regard, the second electrode may be formed of lithium (Li), magnesium (Mg), aluminum (Al), aluminum (Al)-lithium (Li), calcium (Ca), magnesium (Mg)-indium (In), magnesium (Mg)-silver (Ag), or the like, and may be formed as a thin film type transmission electrode. In some example embodiments, to manufacture a top-emission light-emitting device, the transmission electrode may be formed of indium tin oxide (ITO) or indium zinc oxide (IZO).

The example embodiment of the organic light-emitting device shown in FIG. 1 is merely one example.

When a phosphorescent dopant is used in the EML, a HBL may be formed between the ETL and the EML or between the E-functional layer and the EML by using vacuum deposition, spin coating, casting, Langmuir-Blodgett (LB) deposition, or the like, in order to prevent diffusion of triplet excitons or holes into the ETL. When the HBL is formed using vacuum deposition or spin coating, the conditions for deposition and coating may be similar to those for the formation of the HIL, although the conditions for deposition and coating may vary according to the material that is used to form the HBL. A suitable hole-blocking material may be used. Some examples of hole-blocking materials are oxadiazole derivatives, triazole derivatives, and phenanthroline derivatives. For example, bathocuproine (BCP) represented by the following formula may be used as a material for forming the HBL.

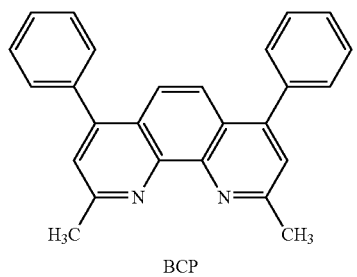

BCP

The thickness of the HBL may be from about 20 Å to about 1000 Å, e.g., about 30 Å to about 300 Å. When the thickness of the HBL is within these ranges, the HBL may have improved hole blocking ability without a substantial increase in driving voltage.

According to example embodiments, the organic light-emitting device may be included in various types of flat panel display devices, such as in a passive matrix organic light-emitting display device or in an active matrix organic light-emitting display device. When the organic light-emitting device is included in an active matrix organic light-emitting display device including a thin-film transistor, the first electrode on the substrate may function as a pixel electrode, electrically connected to a source electrode or a drain electrode of the thin-film transistor. Moreover, the organic light-emitting device may also be included in flat panel display devices having double-sided screens.

In some example embodiments, the organic layer of the organic light-emitting device may be formed of the compound of Formula 1 by using a deposition method or may be formed using a wet method of coating a solution of the compound of Formula 1.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

Synthesis Example 1

Synthesis of Compound 1

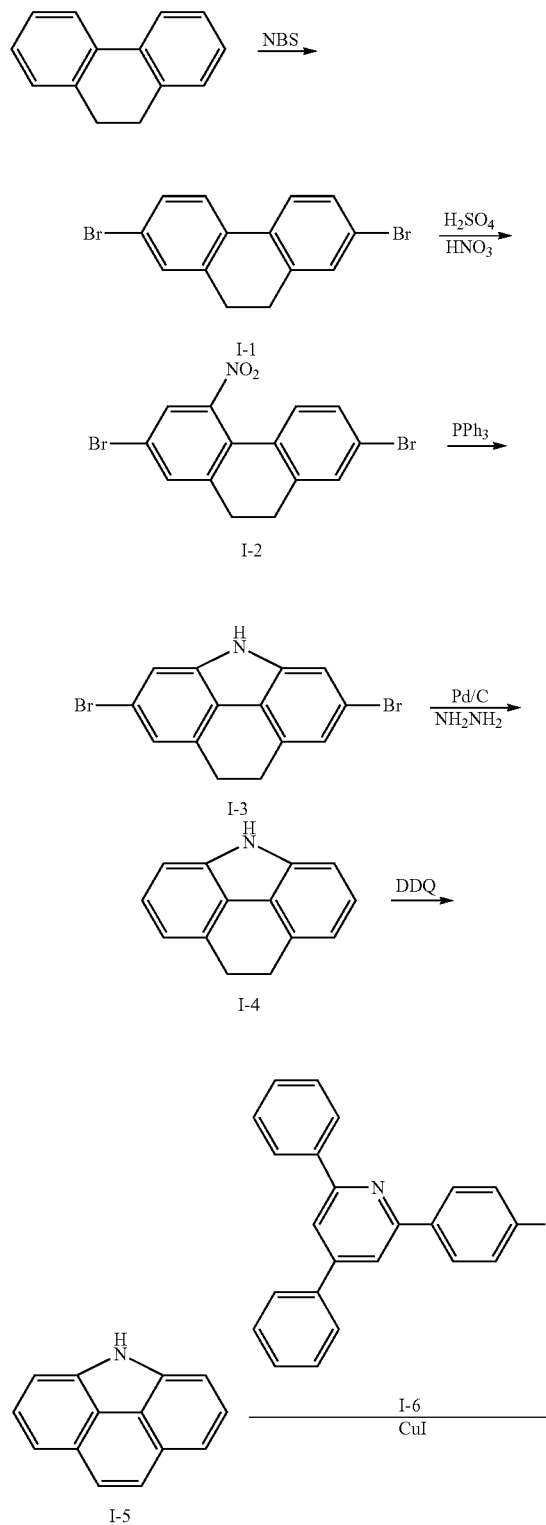

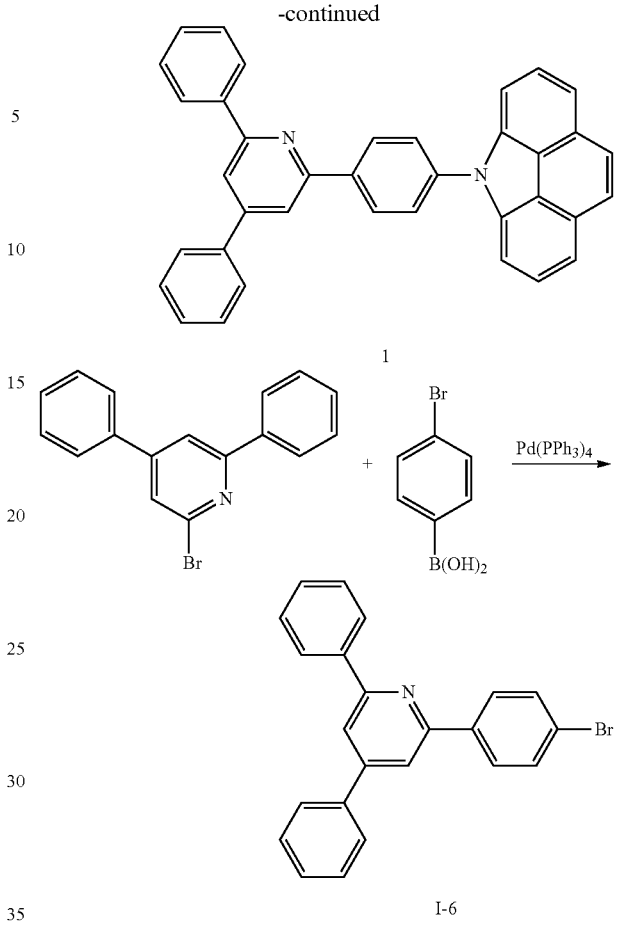

Synthesis of Intermediate I-1

10.0 g (55.4 mmol) of 9,10-dihydrophenanthrene, 21.8 g (121.0 mmol) of N-bromosuccinimide, and 0.5 g (2.7 mmol) of p-TsOH were dissolved in 30 mL of acetonitrile, and then stirred at about 50° C. for about 12 hours. The reaction solution was cooled down to room temperature, and stirred for about 30 minutes to precipitate crystals. The crystals were collected through a vacuum filter, and washed with methanol to obtain 8.42 g of Intermediate I-1 as gray crystals (Yield 45%). This compound was identified using liquid chromatography-mass spectroscopy (LC-MS). $C_{14}H_{10}Br_2$ $M^+$ 336.9

Synthesis of Intermediate I-2

After 5.0 g (15.0 mmol) of Intermediate I-1 was completely dissolved in 50 mL of dichloromethane, 1.7 g (30.0 mmol) of nitric acid was added, and 1.5 g (15.0 mmol) of sulfuric acid was slowly dropwise added thereto to obtain a solution, which was then stirred at about 30° C. for about 6 hours. After completion of the reaction, the reaction solution was cooled down to room temperature, 50 mL of methanol was added thereto and stirred for about 2 hours to precipitate crystals. The crystals were collected through a vacuum filter, and washed with methanol to obtain 5.2 g of Intermediate I-2 as yellow crystals (Yield 90%). This compound was identified using liquid chromatography-mass spectroscopy (LC-MS). $C_{14}H_{19}Br_2NO_2$ $M^+$ 381.9

Synthesis of Intermediate I-3

After 4.6 g (12.0 mmol) of Intermediate I-2 was dissolved in 30 mL of o-dichlorobenzene and heated until completely dissolved, 4.7 g (18.0 mmol) of triphenylphosphine was added thereto and stirred at about 180° C. for about 3 hours. After the reaction solution was cooled down to room temperature, the solvent was removed by evaporation to obtain a residue, which was then separated and purified using silica gel column chromatography, and washed with methanol to obtain 2.9 g of Intermediate I-3 as white crystals (Yield: 70%). This compound was identified using liquid chromatography-mass spectroscopy (LC-MS). $C_{14}H_9Br_2N$ M+ 349.9

Synthesis of Intermediate I-4

After 10 g (28.5 mmol) of Intermediate I-3 and 0.03 g (0.28 mmol) of Pd/C were dissolved in 100 mL of ethanol at room temperature, the temperature was increased up to about 50° C., and 5.48 g (171 mmol) of hydrazine was dropwise added thereto and stirred for about 24 hours. The reaction solution was cooled down to room temperature, washed with acetone, and then added with 100 mL of ice water to obtain 3.63 g of Intermediate I-4 as white crystals (Yield: 66%). This compound was identified using liquid chromatography-mass spectroscopy (LC-MS). $C_{14}H_{11}N$ M+ 194.1

Synthesis of Intermediate I-5

After 10 g (51.8 mmol) of Intermediate I-4 was dissolved in 100 mL of toluene in an oxygen atmosphere, 1.57 g (7.6 mmol) of 2,3-dichloro-5,6-dicyano-1,4-benzoquinone and 0.52 g (7.6 mmol) of $NaNO_2$ were added thereto. After being stirred at about 110° C. for about 6 hours and completion of the reaction, the reaction solution was cooled down to room temperature, and the solvent was evaporated. The residue was separated and purified using silica gel column chromatography to obtain 9.00 g of Intermediate I-5 (Yield: 90%). This compound was identified using liquid chromatography-mass spectroscopy (LC-MS). $C_{14}H_9N$ M+ 192.1

Synthesis of Intermediate I-6

3.09 g (10.0 mmol) of 2-bromo-4,6-diphenylpyridine, 2.00 g (10.0 mmol) of 4-bromophenylboronic acid, 0.58 g (0.5 mmol) of tetrakis(triphenylphosphine)palladium (Pd(PPh$_3$)$_4$), and 4.14 g (30.0 mmol) of $K_2CO_3$ were dissolved in 40 mL of a mixed solution of tetrahydrofuran (THF) and $H_2O$ (2:1 by volume), and then stirred at about 80° C. for about 10 hours. The reaction solution was cooled to room temperature, and 40 mL of water was added thereto, followed by three times of extraction with 50 mL of ethyl ether. The organic phase was collected and was dried using magnesium sulfate to evaporate the solvent. The residue was separated and purified using silica gel column chromatography to obtain 2.85 g of Intermediate I-6 (Yield: 74%). This compound was identified using liquid chromatography-mass spectroscopy (LC-MS). $C_{23}H_{16}BrN$ M+ 386.0

Synthesis of Compound 1

1.92 g (5.0 mmol) of Intermediate I-6, 0.96 g (5.0 mmol) of Intermediate I-5, 0.1 g (0.5 mmol) of 1,10-phenanthroline, 0.19 g (1.0 mmol) of CuI, and 2.07 g (15.0 mmol) of $K_2CO_3$ were dissolved in 20 mL of N,N-dimethylformamide (DMF) to obtain a solution, which was then stirred at about 80° C. for about 24 hours. The reaction solution was cooled down to room temperature, and then extracted three times with 20 mL of water and 20 mL of diethylether. The organic phase was collected and was dried using magnesium sulfate to evaporate the solvent. The residue was separated and purified using silica gel column chromatography to obtain 1.71 g of Compound 1 (Yield: 69%). This compound was identified using mass spectroscopy/fast atom bombardment (MS/FAB) and $^1H$ nuclear magnetic resonance (NMR). $C_{37}H_{24}N_2$ cal. 496.19, found 496.22

$^1H$ NMR (CDCl$_3$, 400 MHz) δ 8.10-8.05 (m, 2H), 7.94-7.91 (m, 2H), 7.80-7.75 (m, 4H), 7.72-7.70 (dd, 2H), 7.56-7.54 (m, 2H), 7.53-7.43 (m, 10H), 7.25-7.23 (m, 2H)

Synthesis Example 2

Synthesis of Compound 4

Compound 4 (1.59 g, Yield: 64%) was synthesized in the same manner as in the synthesis of Compound 1, except that 4-bromo-2,6-diphenylpyridine, instead of 2-bromo-4,6-diphenylpyridine, was used to synthesize Compound 1. This compound was identified using MS/FAB and $^1H$ NMR. $C_{36}H_{23}N_3$ cal. 497.19, found 497.21

$^1H$ NMR (CDCl$_3$, 400 MHz) δ 8.29-8.25 (m, 2H), 8.12-8.10 (m, 2H), 8.03-8.01 (m, 2H), 8.00 (s, 1H), 7.81 (d, 2H), 7.57-7.46 (m, 11H), 7.36-7.31 (m, 3H)

Synthesis Example 3

Synthesis of Compound 11

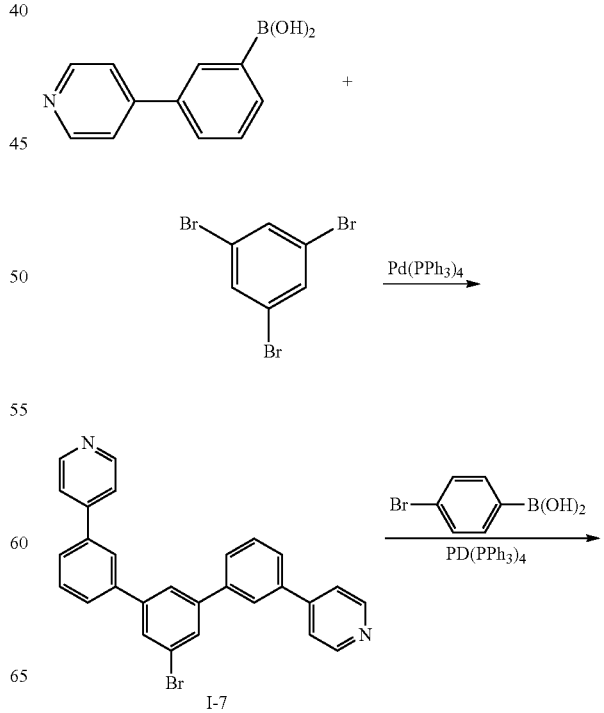

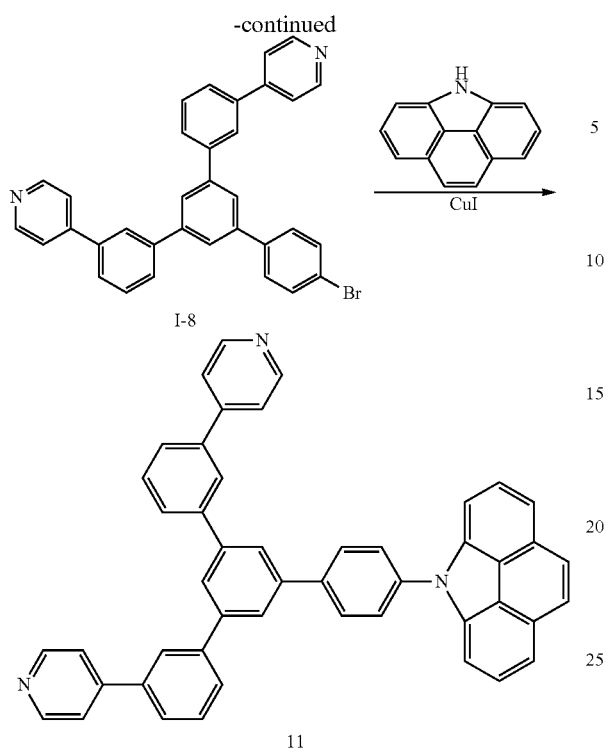

Synthesis of Intermediate I-7

7.96 g (40.0 mmol) of 3-pyridine-4-nyl-phenylboronic acid, 6.22 g (20.0 mmol) of 1,3,5-tribromobenzene, 1.16 g (1.0 mmol) of tetrakis(triphenylphosphine)palladium (Pd(PPh$_3$)$_4$), and 8.2 g (60.0 mmol) of K$_2$CO$_3$ were dissolved in 100 mL of a mixed solution of tetrahydrofuran (THF) and H$_2$O (2:1 by volume), and then stirred at about 80° C. for about 10 hours. The reaction solution was cooled to room temperature, and 80 mL of water was added thereto, followed by three times of extraction with 60 mL of ethyl ether. The organic phase was collected and was dried using magnesium sulfate to evaporate the solvent. The residue was separated and purified using silica gel column chromatography to obtain 6.64 g of Intermediate I-7 (Yield: 72%). This compound was identified using liquid chromatography-mass spectroscopy (LC-MS). C$_{28}$H$_{19}$BrN$_2$ M$^+$ 463.1

Synthesis of Intermediate I-8

4.62 g (10.0 mmol) of Intermediate I-7, 2.00 g (10.0 mmol) of 4-bromophenylboronic acid, 0.58 g (0.5 mmol) of tetrakis(triphenylphosphine)palladium (Pd(PPh$_3$)$_4$), and 4.14 g (30.0 mmol) of K$_2$CO$_3$ were dissolved in 50 mL of a mixed solution of tetrahydrofuran (THF) and H$_2$O (2:1 by volume), and then stirred at about 80° C. for about 10 hours. The reaction solution was cooled to room temperature, and 40 mL of water was added thereto, followed by three times of extraction with 50 mL of ethyl ether. The organic phase was collected and was dried using magnesium sulfate to evaporate the solvent. The residue was separated and purified using silica gel column chromatography to obtain 3.82 g of Intermediate I-8 (Yield: 71%). This compound was identified using LC-MS. C$_{34}$H$_{23}$BrN$_2$ M$^+$ 539.1

Synthesis of Compound 11

2.69 g (5.0 mmol) of Intermediate I-8, 0.96 g (5.0 mmol) of Intermediate I-5, 0.1 g (0.5 mmol) of 1,10-phenanthroline, 0.19 g (1.0 mmol) of CuI, and 2.07 g (15.0 mmol) of K$_2$CO$_3$ were dissolved in 30 mL of N,N-dimethylformamide (DMF) to obtain a solution, which was then stirred at about 80° C. for about 24 hours. The reaction solution was cooled down to room temperature, and then extracted three times with 30 mL of water and 30 mL of diethylether. The organic phase was collected and was dried using magnesium sulfate to evaporate the solvent. The residue was separated and purified using silica gel column chromatography to obtain 2.17 g of Compound 11 (Yield: 67%). This compound was identified using MS/FAB and $^1$H NMR. C$_{48}$H$_{31}$N$_3$ cal. 649.25, found 649.30

$^1$H NMR (CDCl$_3$, 400 MHz) δ 8.33-8.30 (m, 4H), 7.97 (t, 2H), 7.83 (d, 2H), 7.80-7.75 (m, 3H), 7.70 (d, 2H), 7.68 (d, 2H), 7.54 (s, 2H), 7.53-7.45 (m, 10H), 7.35-7.31 (m, 2H), 7.24-7.20 (m, 2H)

Synthesis Example 4

Synthesis of Compound 15

Compound 15 (1.83 g, Yield: 67%) was synthesized in the same manner as in the synthesis of Compound 1, except that 4-bromo-2,6-diphenylpyridine and 4-bromo-1-naphthaleneboronic acid, instead of 2-bromo-4,6-diphenylpyridine and 4-bromophenylboronic acid, respectively, were used to synthesize Compound 1. This compound was identified using MS/FAB and $^1$H NMR. C$_{41}$H$_{26}$N$_2$ cal. 546.21, found 546.24

$^1$H NMR (CDCl$_3$, 400 MHz) δ 8.25-8.13 (dd, 1H), 8.15-8.10 (m, 4H), 8.04 (s, 2H), 7.81-7.79 (dd, 2H), 7.75-7.71 (dd, 1H), 7.66-7.64 (m, 1H), 7.53-7.48 (m, 2H), 7.47-7.43 (m, 811), 7.40-7.38 (m, 4H), 7.33-7.29 (m, 1H)

Synthesis Example 5

Synthesis of Compound 59

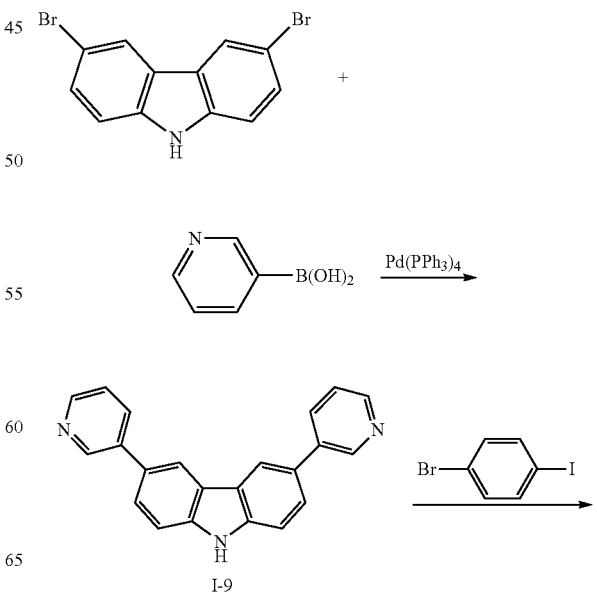

-continued

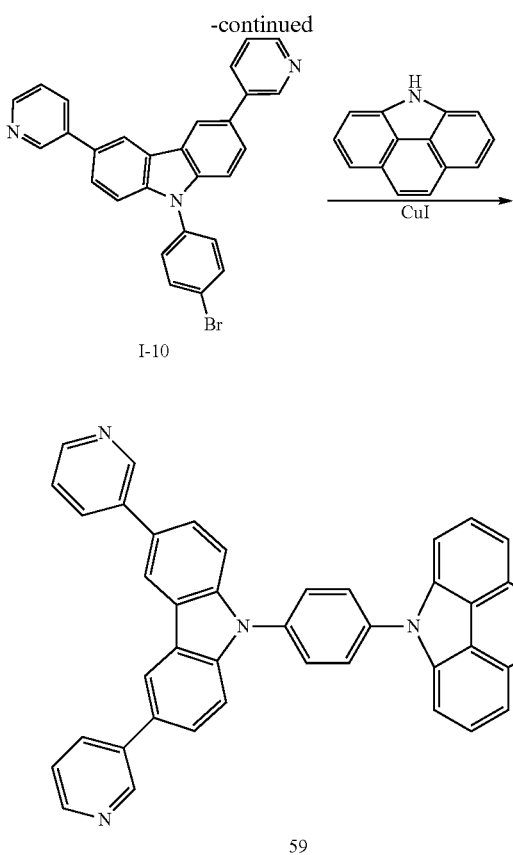

Synthesis of Intermediate I-9

4.92 g (40.0 mmol) of 3-pyridineboronic acid, 6.46 g (20.0 mmol) of 3,6-dibromo-9H-carbazole, 1.16 g (1.0 mmol) of tetrakis(triphenylphosphine)palladium (Pd (PPh$_3$)$_4$), and 8.28 g (60.0 mmol) of K$_2$CO$_3$ were dissolved in 100 mL of a mixed solution of tetrahydrofuran (THF) and H$_2$O (2:1 by volume), and then stirred at about 80° C. for about 10 hours. The reaction solution was cooled to room temperature, and 80 mL of water was added thereto, followed by three times of extraction with 60 mL of ethyl ether. The organic phase was collected and was dried using magnesium sulfate to evaporate the solvent. The residue was separated and purified using silica gel column chromatography to obtain 4.37 g of Intermediate I-9 (Yield: 68%). This compound was identified using LC-MS. C$_{22}$H$_{15}$N$_3$ M$^+$ 322.1

Synthesis of Intermediate I-10

3.85 g (12.0 mmol) of Intermediate I-9, 2.82 g (10.0 mmol) of 4-bromo-1-iodobenzene, 0.18 g (0.2 mmol) of Pd$_2$(dba)$_3$, 0.02 g (0.2 mmol) of PtBu$_3$, and 2.07 g (15.0 mmol) of KOtBu were dissolved in 60 mL of toluene to obtain a mixture, which was then stirred at about 85° C. for 4 hours. The reaction solution was cooled down to room temperature, and then extracted three times with 50 mL of water and 50 mL of diethylether. The organic phase was collected and was dried using magnesium sulfate to evaporate the solvent. The residue was separated and purified using silica gel column chromatography to obtain 3.09 g of Intermediate I-10 (Yield: 65%). This compound was identified using LC-MS. C$_{28}$H$_{18}$BrN$_3$ M$^+$ 476.1

Synthesis of Compound 59

2.38 g (5.0 mmol) of Intermediate I-10, 0.96 g (5.0 mmol) of Intermediate I-5, 0.1 g (0.5 mmol) of 1,10-phenanthroline, 0.19 g (1.0 mmol) of CuI, and 2.07 g (15.0 mmol) of K$_2$CO$_3$ were dissolved in 30 mL of N,N-dimethylformamide (DMF) to obtain a solution, which was then stirred at about 80° C. for about 24 hours. The reaction solution was cooled down to room temperature, and then extracted three times with 30 mL of water and 30 mL of diethylether. The organic phase was collected and was dried using magnesium sulfate to evaporate the solvent. The residue was separated and purified using silica gel column chromatography to obtain 1.96 g of Compound 59 (Yield: 67%). This compound was identified using MS/FAB and $^1$H NMR. C$_{42}$H$_{26}$N$_4$ cal. 586.22, found 586.23

$^1$H NMR (CDCl$_3$, 400 MHz) δ 8.51-8.49 (m, 2H), 8.35-8.33 (tt, 2H), 8.22-8.21 (m, 2H), 8.09-8.06 (tt, 2H), 7.86 (d, 2H), 7.79 (d, 2H), 7.61 (d, 1H), 7.60 (d, 1H), 7.55 (s, 2H), 7.52-7.46 (m, 6H), 7.31-7.27 (m, 2H), 7.23-7.20 (m, 2H)

Additional compounds were synthesized according to the same synthetic pathways and the same method as described above. Analysis data of these compounds by $^1$H NMR and MS/FAB are shown in Table 1 below.

Other compounds not shown in Table 1 may also be synthesized based on the above-described synthetic pathways and source materials.

TABLE 1

| Cmpd | $^1$H NMR (CDCl$_3$, 400 MHz) | MS/FAB found | MS/FAB calc. |
|---|---|---|---|
| 1 | δ = 8.10-8.05 (m, 2H), 7.94-7.91 (m, 2H), 7.80-7.75 (m, 4H), 7.72-7.70 (dd, 2H), 7.56-7.54 (m, 2H), 7.53-7.43 (m, 10H), 7.25-7.23 (m, 2H) | 496.22 | 496.19 |
| 4 | δ = 8.29-8.25 (m, 2H), 8.12-8.10 (m, 2H), 8.03-8.01 (m, 2H), 8.00 (s, 1H), 7.81 (d, 2H), 7.57-7.46 (m, 11H), 7.36-7.31 (m, 3H) | 497.21 | 497.19 |
| 7 | δ = 8.30-8.27 (m, 2H), 8.14-8.11 (m, 4H), 7.99 (s, 1H), 7.86-7.83 (m, 4H), 7.76 (d, 2H), 7.61-7.58 (m, 4H), 7.55-7.51 (m, 8H), 7.50 (m, 6H) | 649.22 | 649.25 |
| 9 | δ = 8.26 (t, 1H), 7.98 (t, 1H), 7.96-7.93 (m, 3H), 7.88-7.85 (m, 1H), 7.82 (d, 1H), 7.78-7.76 (dd, 2H), 7.73 (d, 1H), 7.70-7.66 (m, 3H), 7.64-7.61 (m, 2H), 7.55 (s, 2H), 7.53-7.48 (m, 3H), 7.45-7.39 (m, 6H), 7.37-7.31 (m, 4H), 7.24-7.21 (m, 2H) | 648.29 | 648.26 |

TABLE 1-continued

| Cmpd | ¹H NMR (CDCl₃, 400 MHz) | MS/FAB found | MS/FAB calc. |
|---|---|---|---|
| 11 | δ = 8.33-8.30 (m, 4H), 7.97 (t, 2H), 7.83 (d, 2H), 7.80-7.75 (m, 3H), 7.70 (d, 2H), 7.68 (d, 2H), 7.54 (s, 2H), 7.53-7.45 (m, 10H), 7.35-7.31 (m, 2H), 7.24-7.20 (m, 2H) | 649.30 | 649.25 |
| 15 | δ = 8.25-8.23 (dd, 1H), 8.15-8.10 (m, 4H), 8.04 (s, 2H), 7.81-7.79 (dd, 2H), 7.75-7.71 (dd, 1H), 7.66-7.64 (m, 1H), 7.53-7.48 (m, 2H), 7.47-7.43 (m, 8H), 7.40-7.38 (m, 4H), 7.33-7.29 (m, 1H) | 546.24 | 546.21 |
| 18 | δ = 8.38-8.35 (m, 4H), 8.22-8.18 (m, 1H), 8.09 (d, 1H), 7.88-7.81 (m, 3H), 7.65-7.58 (m, 6H), 7.48-7.44 (m, 3H), 7.42-7.39 (m, 6H) | 548.23 | 548.20 |
| 23 | δ = 8.36 (d, 2H), 8.24 (t, 1H), 8.09-8.05 (m, 5H), 7.83-7.78 (m, 6H), 7.76-7.73 (dd, 1H), 7.71 (d, 1H), 7.69-7.66 (m, 2H), 7.55-7.50 (m, 2H), 7.48-7.44 (m, 5H), 7.42-7.37 (m, 7H), 7.33-7.29 (m, 1H) | 699.30 | 699.27 |
| 27 | δ = 8.27-8.26 (m, 1H), 8.16-8.11 (m, 3H), 8.03-8.01 (m, 1H), 7.84-7.82 (dd, 1H), 7.79-7.74 (m, 5H), 7.67 (d, 2H), 7.57-7.50 (m, 7H), 7.49-7.43 (m, 6H) | 546.24 | 546.21 |
| 32 | δ = 8.33-8.31 (m, 1H), 8.21-8.19 (dd, 1H), 8.12-8.09 (m, 2H), 8.02-8.00 (m, 1H), 7.86-7.84 (m, 1H), 7.80-7.75 (m, 9H), 7.69-7.67 (m, 2H), 7.61-7.57 (m, 5H), 7.54-7.49 (m, 7H), 7.46-7.40 (m, 5H) | 698.31 | 698.27 |
| 38 | δ = 8.42 (d, 1H), 8.35-8.31 (m, 4H), 8.23 (t, 2H), 8.18-8.16 (dd, 1H), 8.10-8.08 (m, 1H), 8.06-8.03 (tt, 2H), 7.95 (s, 1H), 7.86-7.82 (m, 3H), 7.78-7.76 (dd, 2H), 7.67-7.64 (m, 2H), 7.60-7.58 (m, 4H), 7.55 (s, 2H), 7.52-7.44 (m, 6H) | 701.24 | 701.26 |
| 41 | δ = 8.21-8.17 (m, 4H), 7.86-7.81 (m, 4H), 7.78-7.76 (dd, 2H), 7.68 (s, 2H), 7.56 (s, 2H), 7.51-7.44 (m, 12H), 7.39-7.35 (m, 2H) | 572.25 | 572.23 |
| 44 | δ = 8.36-8.33 (m, 4H), 8.13-8.10 (m, 2H), 8.01-7.98 (m, 2H), 7.83-7.80 (m, 2H), 7.64 (t, 1H), 7.62-7.60 (m, 2H), 7.58 (t, 1H), 7.53 (s, 2H), 7.51-7.46 (m, 5H), 7.43-7.36 (m, 5H) | 574.20 | 574.22 |
| 50 | δ = 8.39 (m, 1H), 8.23-8.21 (m, 1H), 8.13-8.11 (dd, 1H), 8.08-8.06 (dd, 1H) 8.01-7.98 (m, 1H), 7.95-7.90 (m, 3H), 7.78-7.70 (m, 6H), 7.66 (d, 1H), 7.57 (d, 1H), 7.55-7.52 (m, 3H), 7.51-7.46 (m, 5H), 7.36-7.32 (m, 2H), 7.24-7.21 (m, 2H) | 676.24 | 676.22 |
| 51 | δ = 8.35-8.33 (m, 2H), 8.25-8.22 (m, 2H), 8.10-8.05 (m, 6H), 7.86 (s, 1H), 7.81-7.77 (m, 4H), 7.58-7.52 (m, 6H), 7.49-7.46 (m, 4H), 7.45-7.42 (m, 2H) | 709.14 | 709.16 |
| 53 | δ = 8.28-8.25 (tt, 2H), 8.23-8.20 (tt, 2H), 8.02-8.00 (m, 1H), 7.90-7.85 (m, 3H), 7.79-7.76 (m, 3H), 7.62-7.57 (m, 3H), 7.55-7.53 (m, 4H), 7.51-7.48 (m, 4H), 7.47-7.40 (m, 3H) | 547.18 | 547.20 |
| 55 | δ = 8.47-8.44 (tt, 2H), 8.38-8.35 (tt, 2H), 8.30 (t, 2H), 8.29-8.26 (m, 4H), 8.21-8.18 (dd, 2H), 8.13-8.11 (dd, 2H), 8.07-8.04 (m, 4H), 7.98 (s, 1H), 7.78-7.75 (m, 2H), 7.60-7.53 (m, 6H), 7.50-7.44 (m, 6H) | 751.30 | 751.27 |
| 56 | δ = 8.15-8.11 (m, 2H), 7.80-7.79 (m, 1H), 7.78-7.77 (m, 1H), 7.72-7.70 (m, 1H), 7.55 (s, 2H), 7.52-7.45 (m, 6H), 7.44-7.41 (m, 2H), 7.30-7.25 (m, 1H) | 384.10 | 384.13 |
| 59 | δ = 8.51-8.49 (m, 2H), 8.35-8.33 (tt, 2H), 8.22-8.21 (m, 2H), 8.09-8.06 (tt, 2H), 7.86 (d, 2H), 7.79 (d, 2H), 7.61 (d, 1H), 7.60 (d, 1H), 7.55 (s, 2H), 7.52-7.46 (m, 6H), 7.31-7.27 (m, 2H), 7.23-7.20 (m, 2H) | 586.23 | 586.22 |
| 61 | δ = 8.20-8.17 (m, 4H), 7.88 (t, 1H), 7.78-7.74 (m, 6H), 7.73-7.71 (m, 2H), 7.57-7.54 (m, 2H), 7.53 (s, 2H), 7.52 (s, 1H), 7.51 (s, 1H), 7.49-7.46 (m, 2H), 7.43-7.40 (m, 4H), 7.29-7.26 (m, 2H) | 653.24 | 653.21 |
| 63 | δ = 7.95-7.94 (m, 2H), 7.78-7.77 (m, 1H), 7.76-7.74 (m, 2H), 7.63-7.60 (m, 2H), 7.54 (s, 2H), 7.51-7.49 (m, 2H), 7.48-7.45 (m, 2H), 7.24-7.21 (m, 2H) | 675.13 | 675.10 |
| 65 | δ = 8.05-8.02 (m, 2H), 7.81-7.76 (m, 3H), 7.74-7.70 (m, 2H), 7.67-7.65 (dd, 1H), 7.58-7.56 (m, 2H), 7.54 (s, 2H), 7.51-7.48 (m, 5H), 7.46-7.39 (m, 3H), 7.37-7.33 (m, 3H), 7.31-7.24 (m, 2H) | 535.18 | 535.20 |

Example 1

To manufacture an anode, a coming 15 Ω/cm² (1200 Å) ITO glass substrate was cut to a size of 50 mm×50 mm×0.7 mm and then sonicated in isopropyl alcohol and pure water each for five minutes, and then cleaned by irradiation of ultraviolet rays for 30 minutes and exposure to ozone. The resulting glass substrate was loaded into a vacuum deposition device.

Then, 2-TNATA, which is a HIL material, was vacuum-deposited on the glass substrate to form a HIL having a thickness of about 600 Å. Then, 4,4'-bis[N-(1-naphthyl)-N-phenylamino]biphenyl (NPB), which is a hole transporting compound, was vacuum-deposited on the HIL to form a HTL having a thickness of about 300 Å.

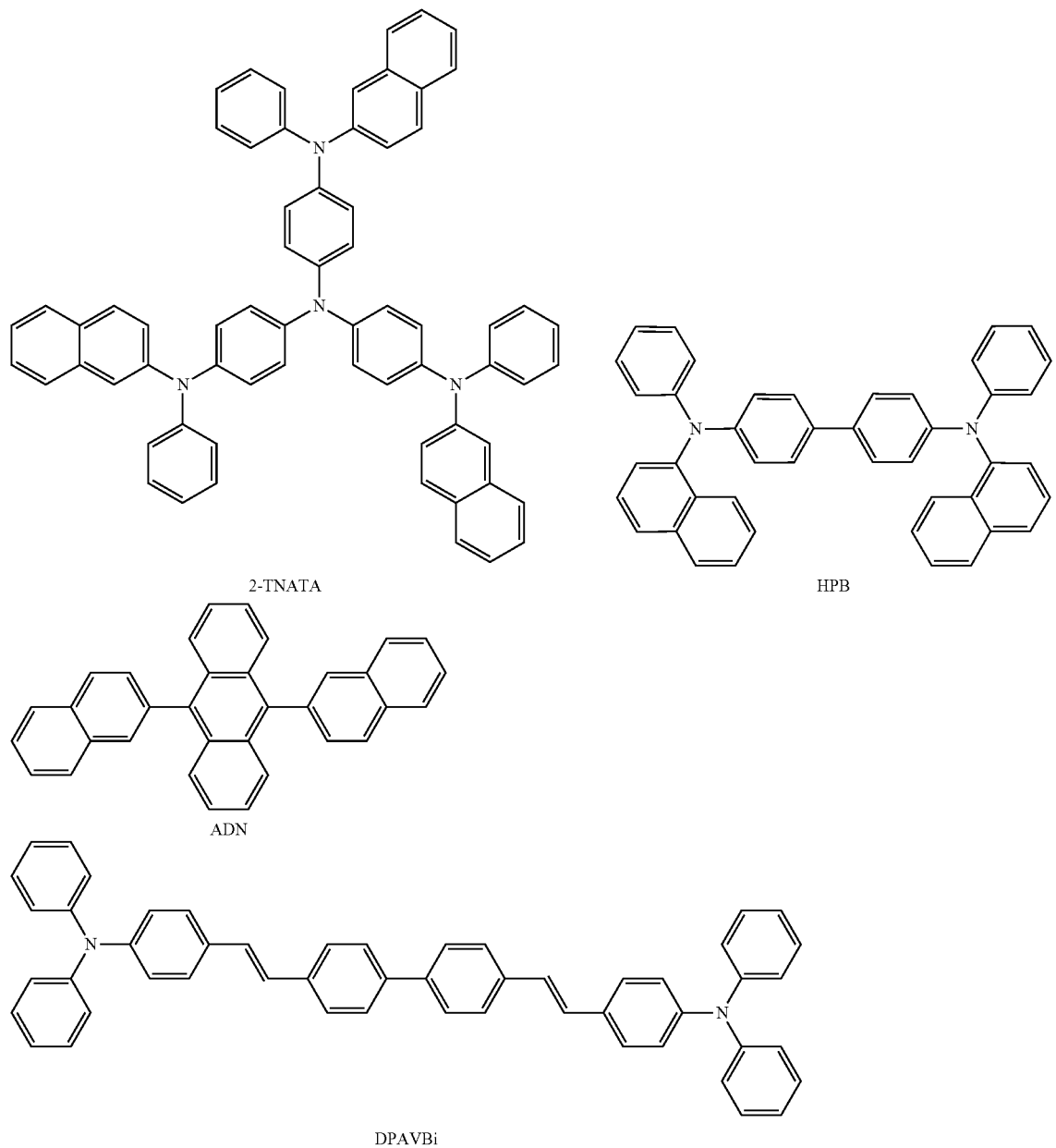

2-TNATA

HPB

ADN

DPAVBi

A blue fluorescent host 9,10-di-naphthalene-2-yl-anthracene (ADN) and a blue fluorescent dopant 4,4'-bis[2-(4-(N,N-diphenylamino)phenyl)vinyl]biphenyl (DPAVBi), were co-deposited on the HTL in a weight ratio of 98:2 to form an EML having a thickness of about 300 Å.

Then, Compound 7 was deposited on the EML to form an ETL having a thickness of 300 Å, and then LiF, which is a halogenated alkali metal, was deposited on the ETL to form an EIL having a thickness of 10 Å. Then, Al was vacuum-deposited on the EIL to form a cathode having a thickness of 3000 Å, thereby forming an LiF/Al electrode and completing the manufacture of an organic light-emitting device.

The organic light-emitting device had a driving voltage of about 5.31V at a current density of 50 mA/cm², a luminosity of 3230 cd/m², a luminescent efficiency of 6.46 cd/A, and a half life-span (hr @100 mA/cm²) of about 513 hours.

Example 2

An organic light-emitting device was manufactured in the same manner as in Example 1, except that Compound 1, instead of Compound 7, was used to form the ETL.

The organic light-emitting device had a driving voltage of about 5.22 V at a current density of 50 mA/cm², a luminosity of 3165 cd/m², a luminescent efficiency of 6.33 cd/A, and a half life-span (hr @100 mA/cm²) of about 387 hours.

Example 3

An organic light-emitting device was manufactured in the same manner as in Example 1, except that Compound 18, instead of Compound 7, was used to form the ETL.

The organic light-emitting device had a driving voltage of about 5.36 V at a current density of 50 mA/cm², a luminosity of 3380 cd/m², a luminescent efficiency of 6.76 cd/A, and a half life-span (hr @100 mA/cm²) of about 487 hours.

Example 4

An organic light-emitting device was manufactured in the same manner as in Example 1, except that Compound 23, instead of Compound 7, was used to form the ETL.
The organic light-emitting device had a driving voltage of about 5.11 V at a current density of 50 mA/cm², a luminosity of 3160 cd/m², a luminescent efficiency of 6.32 cd/A, and a half life-span (hr @100 mA/cm²) of about 338 hours.

Example 5

An organic light-emitting device was manufactured in the same manner as in Example 1, except that Compound 32, instead of Compound 7, was used to form the ETL.
The organic light-emitting device had a driving voltage of about 5.26 V at a current density of 50 mA/cm², a luminosity of 3465 cd/m², a luminescent efficiency of 6.93 cd/A, and a half life-span (hr @ 100 mA/cm²) of about 536 hours.

Example 6

An organic light-emitting device was manufactured in the same manner as in Example 1, except that Compound 44, instead of Compound 7, was used to form the ETL.
The organic light-emitting device had a driving voltage of about 5.21 V at a current density of 50 mA/cm², a luminosity of 3415 cd/m², a luminescent efficiency of 6.83 cd/A, and a half life-span (hr @100 mA/cm²) of about 564 hours.

Example 7

An organic light-emitting device was manufactured in the same manner as in Example 1, except that Compound 51, instead of Compound 7, was used to form the ETL.
The organic light-emitting device had a driving voltage of about 5.25 V at a current density of 50 mA/cm², a luminosity of 3280 cd/m², a luminescent efficiency of 6.56 cd/A, and a half life-span (hr @100 mA/cm²) of about 532 hours.

Example 8

An organic light-emitting device was manufactured in the same manner as in Example 1, except that Compound 55, instead of Compound 7, was used to form the ETL.
The organic light-emitting device had a driving voltage of about 5.29 V at a current density of 50 mA/cm², a luminosity of 3260 cd/m², a luminescent efficiency of 6.52 cd/A, and a half life-span (hr @100 mA/cm²) of about 431 hours.

Example 9

An organic light-emitting device was manufactured in the same manner as in Example 1, except that Compound 65 instead of Compound 7 was used to form the ETL.
The organic light-emitting device had a driving voltage of about 5.72 V at a current density of 50 mA/cm², a luminosity of 3810 cd/m², a luminescent efficiency of 7.62 cd/A, and a half life-span (hr @100 mA/cm²) of about 469 hours.

Comparative Example 1

An organic light-emitting device was manufactured in the same manner as in Example 1, except that $Alq_3$ instead of Compound 7 was used to form the ETL.

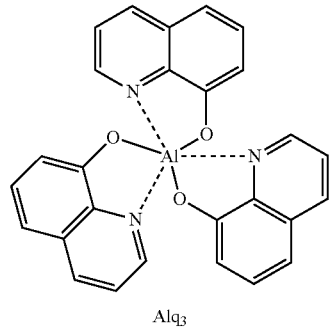

$Alq_3$

The organic light-emitting device had a driving voltage of about 7.35 V at a current density of 50 mA/cm², a luminosity of 2065 cd/m², a luminescent efficiency of 4.13 cd/A, and a half life-span (hr @100 mA/cm²) of about 145 hours.

The organic light-emitting devices manufactured using the heterocyclic compounds of Formula 1 above according to embodiments as ETL materials had significantly lower driving voltages by about 1 V or greater, and improved I-V-L characteristics, compared to those manufactured using $Alq_3$. The organic light-emitting devices using the heterocyclic compounds of Formula 1 above had markedly improved lifetimes. Characteristics, including lifetime characteristics, of the organic light-emitting devices of Examples 1 to 9 and Comparative Example 1 are shown in Table 2 below.

TABLE 2

|  | ETL material | Driving voltage (V) | Current density (mA/cm²) | Luminosity (cd/m²) | Efficiency (cd/A) | Emission color | Half-life span (hr @100 mA/cm²) |
|---|---|---|---|---|---|---|---|
| Example 1 | Compound 7 | 5.31 | 50 | 3,230 | 6.46 | Blue | 513 hr |
| Example 2 | Compound 11 | 5.22 | 50 | 3,165 | 6.33 | Blue | 387 hr |
| Example 3 | Compound 18 | 5.36 | 50 | 3,380 | 6.76 | Blue | 487 hr |
| Example 4 | Compound 23 | 5.11 | 50 | 3,160 | 6.32 | Blue | 338 hr |
| Example 5 | Compound 32 | 5.26 | 50 | 3,465 | 6.93 | Blue | 536 hr |
| Example 6 | Compound 44 | 5.21 | 50 | 3,415 | 6.83 | Blue | 564 hr |
| Example 7 | Compound 51 | 5.25 | 50 | 3,280 | 6.56 | Blue | 532 hr |
| Example 8 | Compound 55 | 5.29 | 50 | 3,260 | 6.52 | Blue | 431 hr |
| Example 9 | Compound 65 | 5.72 | 50 | 3,810 | 7.62 | Blue | 469 hr |
| Comparative Example 1 | $Alq_3$ | 7.35 | 50 | 2,065 | 4.13 | Blue | 145 hr |

Example 1

By way of summation and review, a unimolecular material having improved electrical stability, high charge-transfer or emission capability, and a high glass transition temperature may be useful.

As described above, according to an example embodiment, the heterocyclic compound of Formula 1 above may provide improved charge transporting capability and improved light-emitting capability, and may be used as an electron transporting material for fluorescent or phosphorescent devices of, e.g., red, green, blue, or white color. Therefore, an organic light-emitting device having high efficiency, low driving voltages, high luminance, and long lifetime may be manufactured using the heterocyclic compound of Formula 1 above.

Embodiments may provide a compound that affords electrical characteristics, improved charge transporting capability, improved emission capability, and/or a glass transition temperature (Tg) high enough to reduce or prevent crystallization. The compound may be used as an electron transporting or electron injecting material for fluorescent or phosphorescent devices of, e.g., red, green, blue, or white color.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A heterocyclic compound represented by Formula 1 below:

<Formula 1>

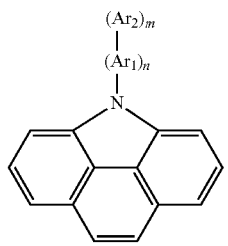

wherein, in Formula 1,
Ar$_1$ is a substituted or unsubstituted C6-60 arylene group;
Ar$_2$ is a substituted or unsubstituted C6-60 aryl group, a substituted or unsubstituted C2-60 heteroaryl group, or a substituted or unsubstituted C6-60 condensed polycyclic group;
n is an integer from 0 to 3; and
m is an integer from 1 to 3.

2. The heterocyclic compound as claimed in claim 1, wherein n is an integer from 1 to 3, and Ar$_1$ in Formula 1 is one of the groups represented by Formulae 2a and 2b below:

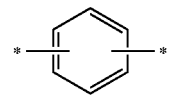

2a

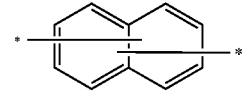

2b wherein, in Formulae 2a and 2b, * indicates a binding site.

3. The heterocyclic compound as claimed in claim 1, wherein Ar$_2$ in Formula 1 is one of the groups represented by Formulae 3a to 3f below:

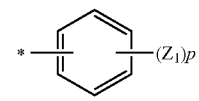

3a

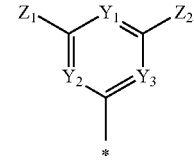

3b

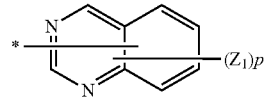

3c

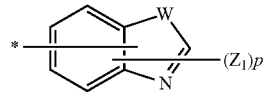

3d

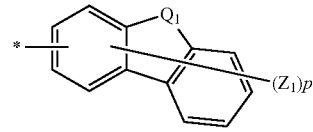

3e

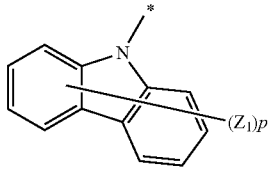

3f wherein, in Formulae 3a to 3f,
Q$_1$ is —CR$_{21}$R$_{22}$—, —S—, or —O—;
W is —O—, —S—, or —NR$_{23}$—;
Y$_1$ to Y$_3$ are each independently CH or N; and
Z$_1$, Z$_2$, R$_{21}$, R$_{22}$, and R$_{23}$ are each independently a hydrogen atom, a deuterium atom, a substituted or unsubstituted C1-C20 alkyl group, a C1-C20 alkylsilyl group, a C1-C20 arylsilyl group, a substituted or unsubstituted C6-C20 aryl group, a substituted or unsubstituted C2-C20 heteroaryl group, a substituted or unsubstituted C6-C20 condensed polycyclic group, an amino group substituted with a C6-C20 aryl group or a C2-C20 heteroaryl group, a halogen group, a cyano group, a nitro group, a hydroxyl group, or a carboxy group; and p is an integer from 1 to 5 in Formula 3a, p is an integer of 1 to 5 in Formula 3c, p is an integer of 1 to 4 in Formula 3d, p is an integer of 1 to 7 in Formula 3e, and p is an integer from 1 to 8 in Formula 3f, and

* indicates a binding site.

4. The heterocyclic compound as claimed in claim 1, wherein Ar₁ in Formula 1 is one of the groups represented by Formulae 4a to 4c below:

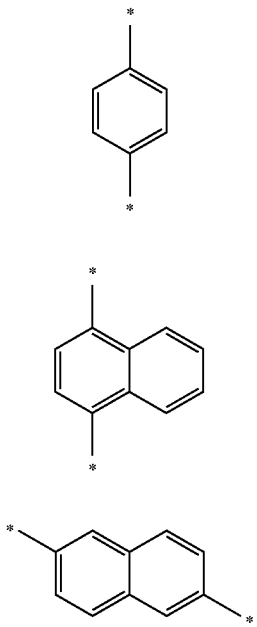

wherein, in Formulae 4a to 4c, * indicates a binding site.

5. The heterocyclic compound as claimed in claim 1, wherein the heterocyclic compound of Formula 1 is one of the compounds below:

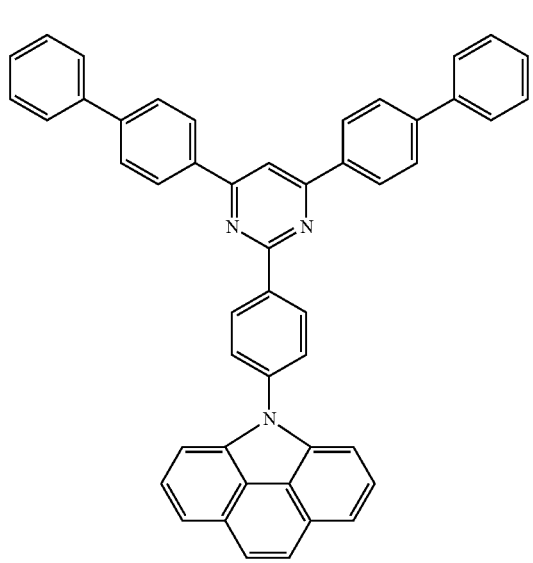

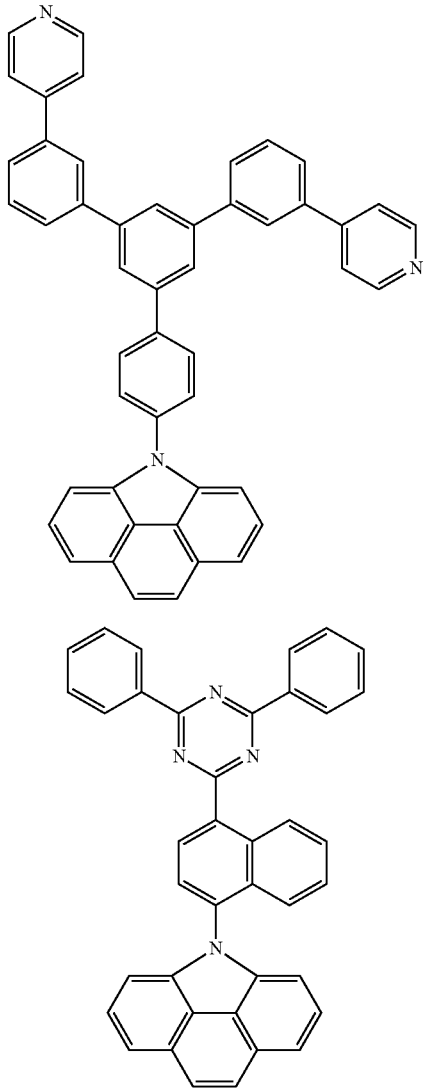

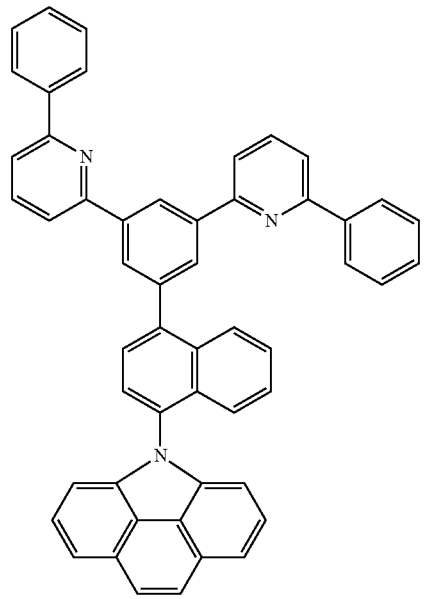

105
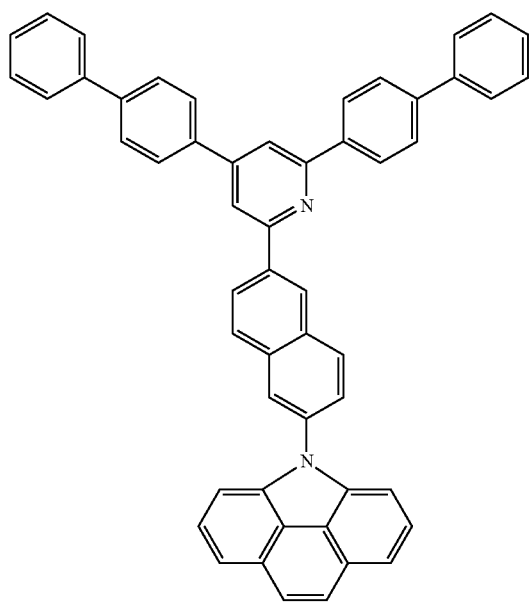
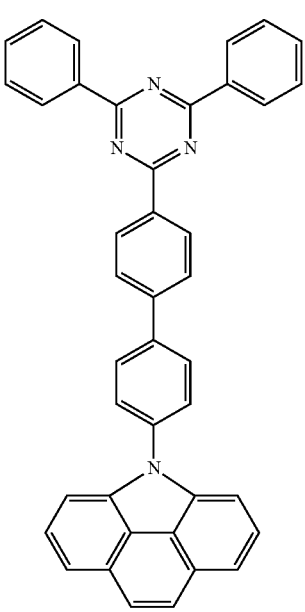
106
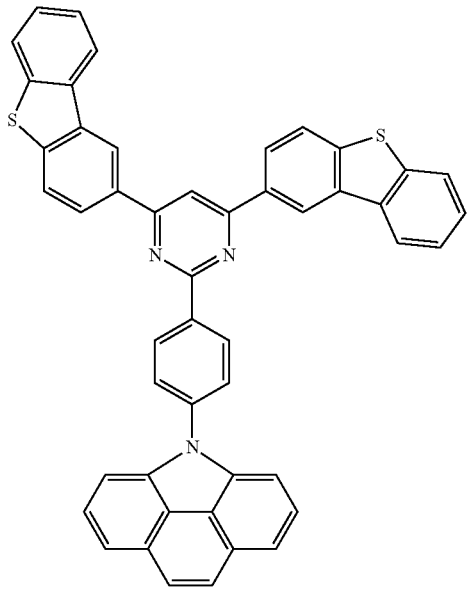
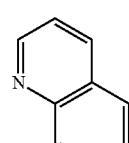

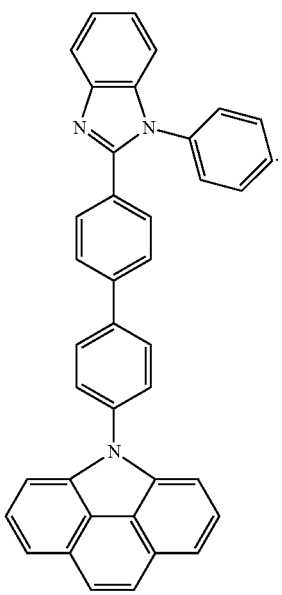

6. An organic light-emitting device, comprising:
a first electrode;
a second electrode; and
an organic layer disposed between the first electrode and the second electrode,
wherein the organic layer includes the heterocyclic compound as claimed in claim 1.

7. The organic light-emitting device as claimed in claim 6, wherein the organic layer is an electron transport layer.

8. The organic light-emitting device as claimed in claim 6, wherein:
the organic layer includes an emission layer and further includes an electron injection layer, an electron transport layer, a functional layer having both electron injection and transport capabilities, a hole injection layer, a hole transport layer, or a functional layer having both hole injection and transport capabilities, and
the emission layer includes an anthracene-based compound, an arylamine-based compound, or a styryl-based compound.

9. The organic light-emitting device as claimed in claim 6, wherein:
the organic layer includes an emission layer and further includes an electron injection layer, an electron transport layer, a functional layer having both electron injection and transport capabilities, a hole injection layer, a hole transport layer, or a functional layer having both hole injection and transport capabilities, and
the emission layer includes red, green, blue, or white emission layers one of which includes a phosphorescent compound.

10. The organic light-emitting device as claimed in claim 9, wherein at least one of the hole injection layer, the hole transport layer, and the functional layer having both hole injection and hole transport capabilities includes a charge-generating material.

11. The organic light-emitting device as claimed in claim 10, wherein the charge-generating material is a p-type dopant.

12. The organic light-emitting device as claimed in claim 11, wherein the p-type dopant is a quinone dopant.

13. The organic light-emitting device as claimed in claim 11, wherein the p-type dopant is a metal oxide.

14. The organic light-emitting device as claimed in claim 11, wherein the p-type dopant is a cyano group-containing compound.

15. The organic light-emitting device as claimed in claim 6, wherein the organic layer includes an electron transport layer, and the electron transport layer further includes a metal complex.

16. The organic light-emitting device as claimed in claim 15, wherein the metal complex is a lithium (Li) complex.

17. The organic light-emitting device as claimed in claim 15, wherein the metal complex is lithium quinolate (LiQ).

18. The organic light-emitting device as claimed in claim 15, wherein the metal complex is Compound 203 below:

<Compound 203>

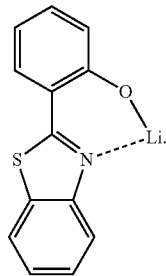

19. The organic light-emitting device as claimed in claim 6, wherein the organic layer is formed from the heterocyclic compound using a wet process.

20. A flat panel display device comprising the organic light-emitting device of claim 6, wherein the first electrode of the organic light-emitting device is electrically connected to a source electrode or a drain electrode of a thin-film transistor.

* * * * *